(12) United States Patent
Ishitsuki et al.

(10) Patent No.: US 8,523,041 B2
(45) Date of Patent: Sep. 3, 2013

(54) CLAMP MEMBER, CLAMP AND ANASTOMOTIC APPARATUS

(75) Inventors: Mitsuru Ishitsuki, Tokyo (JP); Yuji Ochiai, Tokyo (JP); Mikio Shiba, Tokyo (JP); Suekichi Sato, Tokyo (JP); Ernest Mikhajlovich Akopov, Moscow (RU); Makoto Shirakawa, Tokyo (JP)

(73) Assignee: Senko Medical Instruments Mfg. Co., Ltd., Tokyo (JP)

( * ) Notice: Subject to any disclaimer, the term of this patent is extended or adjusted under 35 U.S.C. 154(b) by 303 days.

(21) Appl. No.: 13/141,174

(22) PCT Filed: Dec. 25, 2009

(86) PCT No.: PCT/JP2009/007321
§ 371 (c)(1),
(2), (4) Date: Jun. 21, 2011

(87) PCT Pub. No.: WO2010/073734
PCT Pub. Date: Jul. 1, 2010

(65) Prior Publication Data
US 2011/0257679 A1    Oct. 20, 2011

(30) Foreign Application Priority Data

Dec. 25, 2008 (JP) .................................. 2008-329866
Dec. 25, 2008 (JP) .................................. 2008-329867

(51) Int. Cl.
*A61B 17/28* (2006.01)
(52) U.S. Cl.
USPC ........................................ 227/179.1; 227/19
(58) Field of Classification Search
USPC ..................... 227/175.1–182.1, 19
See application file for complete search history.

(56) References Cited

U.S. PATENT DOCUMENTS

| 4,216,890 | A | | 8/1980 | Akopov et al. |
| 5,431,323 | A | * | 7/1995 | Smith et al. ................. 227/177.1 |
| 5,465,894 | A | * | 11/1995 | Clark et al. ................. 227/175.1 |
| 5,478,003 | A | * | 12/1995 | Green et al. ................. 227/176.1 |
| 5,484,451 | A | * | 1/1996 | Akopov et al. ............... 606/139 |
| 5,573,543 | A | * | 11/1996 | Akopov et al. ............... 606/144 |
| 2008/0308607 | A1 | * | 12/2008 | Timm et al. ................. 227/176.1 |
| 2008/0319442 | A1 | * | 12/2008 | Unger et al. ................... 606/48 |
| 2011/0257679 | A1 | * | 10/2011 | Ishitsuki et al. ............. 606/205 |

FOREIGN PATENT DOCUMENTS

| JP | 53004758 | 2/1978 |
| JP | 53016634 | 6/1978 |
| JP | 55038154 | 3/1980 |
| JP | 58001939 | 1/1983 |
| JP | 02111352 | 4/1990 |

* cited by examiner

*Primary Examiner* — Brian D Nash
(74) *Attorney, Agent, or Firm* — Hoffmann & Baron, LLP

(57) ABSTRACT

The anastomotic apparatus is equipped, in a fork which extends in the stapling direction, with an organ gripping mechanism which has a first gripping teeth plate member, a second gripping teeth plate member, a housing, and a clamping teeth drive section connected to at least the aforementioned first gripping teeth plate member or the second gripping teeth plate member to move the first gripping teeth plate member and the second gripping teeth plate member relative to each other by one unit space in the longitudinal direction, and is configured to clamp near a section of an organ to be stapled; an extroverting mechanism configured to move the aforementioned organ gripping mechanism within a turn-out movement range; and a grip controlling mechanism. With the anastomotic apparatus, the burden on the organ tissue can be reduced.

16 Claims, 63 Drawing Sheets

SECTION A-A

SECTION B-B

SECTION F-F

SECTION E-E

SECTION H-H

SECTION G-G

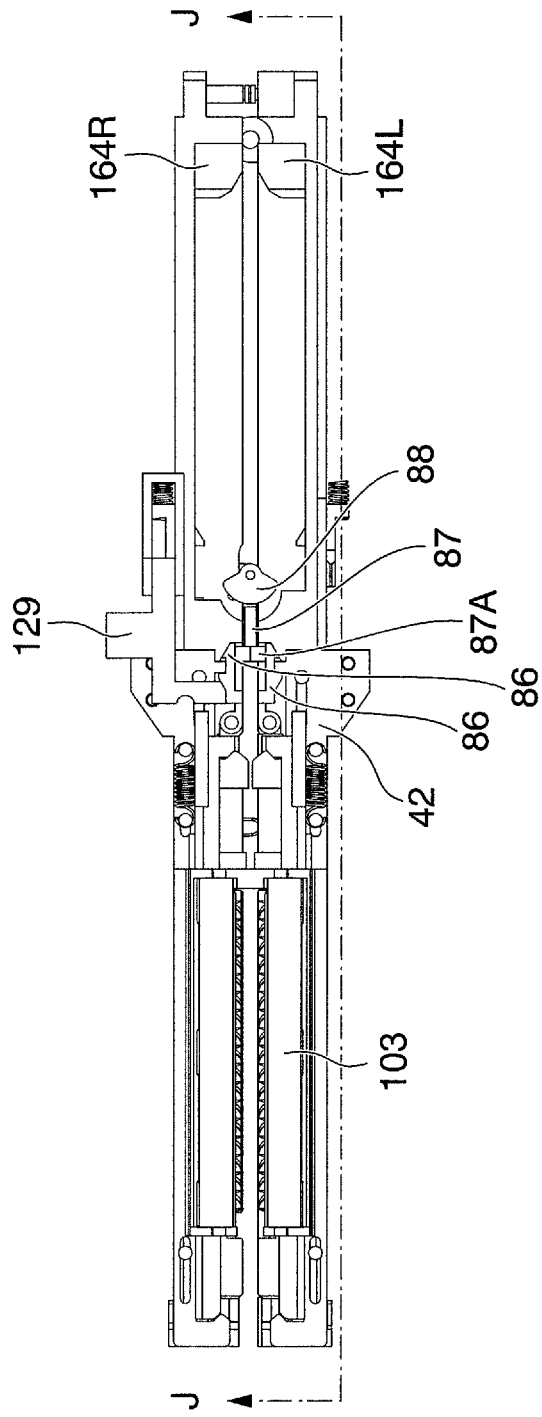

CLAMP MEMBER, CLAMP AND ANASTOMOTIC APPARATUS

TECHNICAL FIELD

The present invention relates to a clamp member, clamp and anastomotic apparatus for gripping organ tissue in order to perform stapling and anastomosis of a digestive organ or the like during a surgical procedure.

Priority is claimed on Japanese Patent Application Nos. 2008-329866 and 2008-329867, filed Dec. 25, 2008, the content of which is incorporated herein by reference.

BACKGROUND ART

When there is diseased tissue present in a hollow viscera (organ tissue, etc.) such as the intestine or stomach in the field of gastroenterological surgery, it is well understood that a restorative procedure is necessary following resection of that diseased site, in order to recreate a continuous digestive tract through end-to-end (end-to-end anastomosis), end-to-side (end-to-side anastomosis), or side-to-side (side-to-side anastomosis) stapling and anastomosis of the remaining normal regions of the hollow viscera.

With regard to anastomotic techniques from among the restorative procedures for the aforementioned tubular biological tissue, the techniques of inverting anastomosis, in which the cut ends of the tubular biological tissue are inverted and stapled intralumenally, and everting anastomosis, in which the cut ends of the tubular biological tissue are everted and stapled extralumenally, are conventionally known. Conventionally, inverting anastomosis has more typically been carried out from the perspective of sanitation and prevention of adhesions. Further, in the case of an inverting anastomosis of the digestive tract, encircling automatic anastomotic apparatuses, in which the staples, i.e. the stapling members, are arrayed in an encircling disposition, are the first choice (see Patent Reference Document No. 1, for example).

However, when employing the automatic anastomotic apparatus disclosed in Patent Reference Document No. 1, it is necessary to insert the main body of the automatic anastomotic apparatus into the lumen of the digestive organ and to insert the anvil head into the digestive organ on the opposite side to be anastomosed. Because the main body is inserted into a non-sterile area and the cut ends of the digestive organ are in an open state, there is a possibility of contamination of the surgical field as a result. Further, not only may surgical time be prolonged because the procedure sequence is complicated and requires considerable time, but there is also the possibility of post-surgical stricture, a well known complication when employing an encircling automatic anastomotic apparatus.

There has been a demand for everting anastomosis techniques in order to resolve the contamination and post-surgical stricture issues that may occur when using the aforementioned encircling automatic anastomotic apparatus. This has resulted in the disclosure of anastomotic apparatuses as a means for efficiently carrying out everting anastomosis in a short time period (see Patent Reference Document No. 2, for example).

PRIOR ART REFERENCES

Patent References

[Patent Reference Document No. 1]
Japanese Patent Application, Laid Open No. 2-111352

[Patent Reference Document No. 2]
Japanese Patent Application, Laid Open No. 55-38154

DISCLOSURE OF THE INVENTION

Problems to be Resolved by the Invention

However, when employing the anastomotic apparatus disclosed in Japanese Patent Reference Document No. 2, the following perspectives apply:

1) The gripping teeth, consisting of pointed teeth and rake teeth, are exposed from the housing. As a result, it is possible for the gripping teeth to cause damage by coming into contract with an object or to cause injury by coming into contact with the operator.
2) Although there are levers for carrying out a variety of operations, the execution sequences are complicated, such that the operator requires suitable proficiency in the various operations.
3) There is a possibility of injury to the biological tissue in the case where an error is made in the operation sequence during anastomosis.

Thus, there has been a desire for a technique for surgical equipment such as stapling devices and anastomotic apparatuses that can easily and stably grip the biological tissue, easily and efficiently carry out stapling and anastomosis, and prevent errors in operation.

The present invention was conceived in view of the above-described circumstances and has as its objective the resolution of at least one of the subjects disclosed below.

1) To provide a clamp member that limits damage of the pointed teeth and rake teeth and prevents injury to the operator by the pointed teeth and rake teeth, and which enables a biological tissue to be easily and efficiently gripped
2) To provide a clamp that can easily and stably grip and evert a biological tissue.
3) To provide an anastomotic apparatus that can be easily operated to efficiently perform an anastomosis.
4) To provide an anastomotic apparatus that can prevent injury to a biological tissue arising from errors in operation during the anastomosis.

Means to Resolve the Problem

The present invention proposes the following means to resolve the above-described problems.

A first aspect of the present invention is a clamp member characterized in having clamping surfaces for gripping organ tissue and stapling surfaces which are on the side for stapling the organ wall, and a fork which is formed extending in the stapling direction, wherein there is provided to the fork:

an organ gripping mechanism composed so as to grip the organ tissue in the vicinity of a site to be stapled, the organ gripping mechanism provided with a first gripping teeth plate member in which a plurality of pointed teeth are disposed at equal pitch in the longitudinal direction of the fork, a second gripping teeth plate member which is disposed along the first gripping teeth plate member and has a plurality of rake teeth corresponding with the various pointed teeth, the rake teeth being disposed with the same pitch as that of the corresponding pointed teeth and being formed so that the distal end side thereof is directed toward the corresponding pointed teeth side, wherein the tips of the rake teeth and the tips of the pointed teeth coincide as a result of relative movement with the first gripping teeth plate member, a housing for housing the first gripping teeth plate member and the second gripping teeth plate member so as to enable relative movement there between, and a gripping teeth drive which is connected to at least one of either the first gripping teeth plate member and the second gripping teeth plate member, and is for relative movement of the first gripping teeth plate member and the second gripping teeth plate member by one pitch increments in the longitudinal direction;

an everting mechanism which is connected to the organ gripping mechanism and moves the organ gripping mechanism within an eversion movement range that transects the longitudinal direction of the fork and extends from a pre-eversion position at which the pointed teeth pierce the vicinity of the stapling site on the organ tissue, to a post-eversion site at which the stapling site on the organ tissue is positioned on the stapling surface; and a grip controlling mechanism which is disposed to the fork and defines the eversion movement range for the organ gripping mechanism, the grip controlling mechanism holding the organ gripping mechanism at the pre-eversion position or the post-eversion position respectively, and controlling the first gripping teeth plate member and the second gripping teeth plate member when the organ gripping mechanism is moved to the post-eversion position side.

The first gripping teeth plate member and the second gripping teeth plate member undergo relative movement in the clamp member according to the present invention. As a result, the pointed teeth pierce the vicinity of the stapling site on the outside of the organ tissue, and the organ tissue is gripped due to coinciding of the tips of the rake teeth with the tips of the pointed teeth. The everting mechanism everts the organ tissue, thereby forming the organ wall, as a result of movement of the organ gripping mechanism in a direction that transects the longitudinal direction of the clamp member. In this specification, phrases referring to "coinciding of the tips of the rake teeth with the tips of the pointed teeth" mean that these distal ends roughly match, with the objective of gripping the organ tissue.

Further, a grip controlling mechanism is provided. When the organ gripping mechanism is maintained at the pre-eversion or post-eversion position, or is moved to the post-eversion position side, the first gripping teeth plate member and the second gripping teeth plate member are suitably controlled so as to not perform any unintentional movement. As a result, the organ tissue is prevented from slipping free from the pointed teeth and rake teeth during eversion, so that holding of the gripped organ tissue can be carried out stably.

The second aspect of the present invention is a clamp member according to the preceding first aspect, characterized in that the organ gripping mechanism is designed so that the pointed teeth advance in the piercing direction when gripping the organ tissue by means of relative movement of the first gripping teeth plate member and the second gripping teeth plate member, and is provided with a gripping teeth protective wall for preventing contact between the tips of the pointed teeth and the rake teeth with the outside by housing the tips of the pointed teeth and the rake teeth when the pointed teeth are at the retracted position in the piercing direction.

In the clamp member according to the present invention, the gripping teeth protective wall houses the tips of the pointed teeth and the rake teeth when they are at the retracted position in the piercing direction. As a result, the tips of the pointed teeth and the rake teeth are prevented from coming into contact with and damaging an external object, and, moreover, injury to the organ tissue from damaged pointed teeth or rake teeth is prevented. The phrase "piercing direction" in this specification indicates the direction in which the pointed teeth are pressed against the outside of the organ tissue (i.e., in the direction of movement of the pointed teeth).

Further, because contact between the surgical assistant or other such operator and the rake teeth is prevented, the operator is able to easily, stably and efficiently utilize the organ gripping mechanism.

The third aspect of the present invention is a clamp member according to the preceding first or second aspect, characterized in that the pointed teeth are formed extending in the piercing direction and inclined toward the rake teeth side.

In the clamp member according to the present invention, the pointed teeth are formed extending in the piercing direction and inclined toward the rake teeth side. As a result, the pointed teeth can easily carry out piercing and, together with the rake teeth, are capable of sufficiently gripping the organ tissue.

A fourth aspect of the present invention is a clamp member according to the preceding first or second aspect, characterized in that the tip end side of the pointed teeth is formed so as to gradually displace toward the rake teeth side.

In the clamp member according to the present invention, the tip end side of the pointed teeth is formed so as to gradually displace toward the rake teeth side. As a result, injury to the organ tissue is prevented, and the organ tissue can be gripped with certainty.

A fifth aspect of the present invention is a clamp member according to one of the first through fourth aspects of the present invention, characterized in that the organ gripping mechanism is provided with:

first engaging cutouts which are formed to the first gripping teeth plate member and have a first slanted cutout, which is inclined toward the side removed from the pointed teeth and in the direction of the gripping action in which the second gripping teeth plate member moves relative to the first gripping teeth plate member when gripping the organ tissue, and an escape, which extends from the edge on the gripping action direction side of the first slanted cutout toward the gripping action direction;

second engaging cutouts which are formed to the second gripping teeth plate member and are inclined toward the side removed from the rake teeth and toward the gripping action direction; and a gripping teeth actuating member which is formed to the gripping teeth drive and engages with the first engaging cutouts and the second engaging cutouts; wherein the gripping teeth actuating member moves in the gripping action direction causing the tips of the rake teeth and the pointed teeth to advance in the piercing direction, while at the same time the rake teeth move toward the corresponding pointed teeth.

In the organ gripping mechanism according to the present invention, the gripping teeth drive is operated to engage the gripping teeth actuating member with the first slanted cutout of the first engaging cutout and with the second engaging cutout, and is moved in the gripping action direction. As a result, the pointed teeth and the rake teeth advance in the piercing direction and pierce the organ tissue.

Further, the gripping teeth actuating member comes into contact with the end on the gripping action direction side of the second engaging cutout and moves through the escape of the first engaging cutout. As a result, the second gripping teeth plate member moves with respect to the first gripping teeth plate member in the direction of the gripping action, causing the rake teeth to move by one pitch only toward the corresponding pointed teeth side so that the tips of the rake teeth coincide with the tips of the pointed teeth.

As a result, movement of the rake teeth and the pointed teeth in a piercing direction, and in the direction in which the respective tips of the rake teeth and the pointed teeth coincide can be carried out through a single manipulation of the gripping teeth drive, so that the organ tissue can be gripped efficiently and with certainty.

The sixth aspect of the present invention is a clamp member according to one of the preceding first through fifth aspects of the present invention, characterized in that the organ gripping mechanism has a guide formed to the stapling surface side of the housing and is able to cut and separate the organ tissue disposed to the clamping surface at the stapling site or at suitable interval from the position corresponding to the stapling site by moving a cutting blade through the guide.

In the clamp member according to the present invention, the cutting blade is guided by a guide that is formed on the stapling surface side. As a result, by moving the cutting blade along the guide, a transected area (cut end) located at the stapling site or at position located at a specific interval from the stapling site is formed.

As a result, the organ tissue disposed to the clamping surface can be easily cut and separated at a suitable site, and the anastomosis of the organ tissue can be carried out stably and efficiently by preventing an excess or insufficiency of organ tissue near the stapling site.

The seventh aspect of the present invention is a clamp member according to one of the preceding first through sixth aspects of the present invention, characterized in that the everting mechanism is provided with an everting operator which is disposed to the respective forks and is connected to the respective organ gripping mechanisms, and which moves the tips of the pointed teeth and the rake teeth through a specific eversion trajectory corresponding to the eversion movement range by means of rotation, sliding and compound actions.

In the clamp member according to the present invention, the everting operator, in which an eversion mechanism is connected to an organ gripping mechanism on each of the forks, carries out rotation, sliding and compound actions. As a result, the tips of the pointed teeth and the rake teeth move through a specific eversion trajectory corresponding to the eversion movement range. Accordingly, it is possible to design an everting operator suitable to the profile, etc. of the everting mechanism and the organ gripping mechanism.

The eighth aspect of the present invention is a clamp member according to one of the preceding first through seventh aspects of the present invention, characterized in that the everting mechanism is capable of everting the organ gripping mechanism using remote manipulation via the everting operator, and is designed to enable holding of the organ gripping mechanism at the pre-eversion position or the post-eversion position.

In the clamp member according to the present invention, remote operation is possible using the everting operator and the organ gripping mechanism can be held at the pre-eversion position or the post-eversion position. As a result, it is possible to easily manipulate the everting operator and hold the organ gripping mechanism at the pre-eversion position or the post-eversion position with certainty so that a stable everting operation can be carried out.

The ninth aspect of the present invention is a clamp member according to one of the preceding first through eighth aspects of the present invention, characterized in that the everting mechanism is provided with a link mechanism consisting of at least four links, and is designed so that the tips of the pointed teeth and the rake teeth move along a specific eversion trajectory corresponding to the eversion movement range due to changes in the arrangement of the link mechanism at the plane which intersects with the stapling direction.

In the clamp member according to the present invention, a link mechanism consisting of at least four links changes its arrangement at the surface which intersects with the stapling direction. As a result, the tips of the pointed teeth and the rake teeth move along a specific eversion trajectory so that the gripped organ tissue can be smoothly everted without being pulled or stretched. As a result, the application of excessive force during eversion of the gripped organ tissue is prevented and the stress on the tissue can be reduced.

The tenth aspect of the present invention is a clamp member according to the preceding ninth aspect of the present invention, characterized in that, in the organ gripping mechanism, the gripping teeth drive and the first gripping teeth plate member and the second gripping teeth plate member are connected to permit relative movement in the direction which intersects with the longitudinal direction of the fork.

In the clamp member according to the present invention, the gripping teeth drive and the first gripping teeth plate member and the second gripping teeth plate member are connected to permit relative movement in the direction which intersects with the longitudinal direction of the fork. As a result, once the everting manipulation has been performed, the tips of the pointed teeth and the rake teeth can be everted while maintaining the position of the gripping teeth drive in the direction that intersects with the longitudinal direction of the fork. Thus, operation of the gripping teeth drive and the everting operator can be easily carried out.

The eleventh aspect of the present invention is a clamp member according to one of the preceding first through eighth aspects of the present invention, characterized in that the everting mechanism is provided with an eversion rotating support for supporting the organ gripping mechanism so that the tips of the pointed teeth and the rake teeth travel on a specific eversion trajectory corresponding to the eversion movement range, by means of rotation about the everting axis which is formed along the stapling direction.

In the clamp member according to the present invention, the everting mechanism rotates about the everting axis which is formed along the stapling direction. As a result, the tips of the pointed teeth and the rake teeth travel on a specific eversion trajectory so that the everting mechanism can be realized through a simple structure.

The twelfth aspect of the present invention is a clamp member according to the preceding eleventh aspect of the present invention, characterized in that the everting mechanism is provided with an everting position engaging member for selectively engaging with the organ gripping mechanism at one of either the pre-eversion position or the post-eversion position, wherein the everting position engaging member engages with the organ gripping mechanism at the pre-eversion position until the gripping teeth drive moves the pointed teeth and the rake teeth to the gripping position, enables eversion of the organ gripping mechanism when the pointed teeth and the rake teeth are in the gripping state and engages with the organ gripping mechanism at the post-eversion position after the everting manipulation has been performed.

In the clamp member according to the present invention, the everting position engaging member engages with the organ gripping mechanism at the pre-eversion position until the gripping teeth drive moves the pointed teeth and the rake teeth to the gripping position, and enables eversion of the organ gripping mechanism when the pointed teeth and the rake teeth are in the gripping state.

Further, because the everting position engaging member engages with the organ gripping mechanism at the post-eversion position after the everting manipulation has been performed, it is possible to hold the organ gripping mechanism at the post-eversion position.

As a result, the organ gripping mechanism and the everting mechanism can be held stably until the anastomosis is complete.

The thirteenth aspect of the present invention is a clamp member according to the preceding twelfth aspect of the present invention, characterized in that the eversion position engaging member is capable of moving together with the organ gripping mechanism and is capable of relative movement with the organ gripping mechanism when the pointed teeth and the rake teeth have moved to the gripping position. Further, the eversion position engaging member is provided with a pre-eversion position engaging part for engaging with the organ gripping mechanism at the pre-eversion position until the pointed teeth and the rake teeth have moved to the gripping position, and a post-eversion position engaging part for engaging with the organ gripping mechanism at the post-eversion position after the organ gripping mechanism has been everted, wherein when the organ gripping mechanism is everted, the eversion position engaging member undergoes movement relative to the organ gripping mechanism, so that the engagement with the organ gripping mechanism changes from the pre-eversion position engaging part to the post-eversion position engaging part.

In the clamp member according to the present invention, an eversion position engaging member is provided which is capable of moving together with the organ gripping mechanism, and the pre-eversion position engaging part and the post-eversion position engaging part which are formed to the eversion position engaging member are designed to hold the organ gripping mechanism at the pre-eversion position or the post-eversion position. Further, when the organ gripping mechanism is everted, the eversion position engaging member moves relative to the organ gripping mechanism and the engagement with the organ gripping mechanism alternates between the pre-eversion position engaging part and the post-eversion position engaging part.

As a result, it is possible to hold the organ gripping mechanism at the pre-eversion position and the post-eversion position with certainty, using a simple design.

The fourteenth aspect of the present invention is a clamp, characterized in being formed by disposing as a pair two of the clamp members according to one of the preceding first through thirteenth aspects of the present invention, wherein the clamping surfaces are able to approach or move away from one another, and, when made to approach one another, the clamping surfaces face one another.

In the clamp according to the present invention, the clamp is formed by disposing two clamp members as a pair so that the clamping surfaces face one another. As a result, the organ tissue gripped by the clamp can be easily and efficiently gripped and everted using the organ gripping mechanism and everting mechanism of the respective clamp members.

The fifteenth aspect of the present invention is a clamp according to the fourteenth aspect of the present invention, characterized in the provision of a gripping action synchronizing means for synchronizing and carrying out relative movement of the organ gripping mechanism disposed to each of the clamp members.

In the clamp according to the present invention, a gripping action synchronizing means is provided for synchronizing and operating the respective organ gripping mechanisms. As a result, the pointed teeth and the rake teeth can simultaneously grip the organ tissue at positions on either side of the hollow portion of the organ. Thus, the organ tissue can be stably gripped, making it possible to carry out stable stapling and anastomosis.

The sixteenth aspect of the present invention is an anastomotic apparatus characterized in that clamps according to the preceding fourteenth or fifteenth aspect of the present invention are disposed as a pair so that their mutual stapling surfaces are able to approach or move away from one another, and so that the stapling surfaces face one another when brought closer together, and in that there is formed in the clamp set a stapling mechanism which is disposed to either one of the clamp members in the two clamp member pairs, a clamp member pair being comprised of the two clamp members which face each other about the stapling surface, wherein the stapling mechanism is provided with:

a staple housing for housing the staples, in which a hole is formed on the stapling surface side through which the staples pass, an ejector for pushing out the staples from the staple housing, and an anvil member which is disposed to the other clamp member of the clamp member pair and which is formed with a profile for shaping the staples on the stapling surface side.

A stapling mechanism is formed respectively to each of the two clamp member pairs in the anastomotic apparatus according to the present invention. The sites to be stapled on the organ wall, which are formed by everting the tissue, are brought into apposition and closed using staples. As a result, the anastomosis of the organ tissue can be carried out efficiently and stably.

Effects of the Invention

The clamp members according to the present invention prevent the unintentional release of the organ tissue from the pointed teeth and the rake teeth when the organ tissue is being everted, so that the organ tissue gripped by the clamp members can be stably held.

The clamp according to the present invention enables easy and efficient gripping and everting of the clamped organ tissue by means of the organ gripping mechanism and the everting mechanism of the respective clamp members composing the clamp.

The anastomotic apparatus according to the present invention enables efficient and stable anastomosis of the organ tissue.

BRIEF DESCRIPTION OF THE DRAWINGS

FIG. 55A is a planar view for explaining the lock releasing mechanism in the anastomotic apparatus according to a second embodiment of the present invention.

BEST MODE FOR CARRYING OUT THE INVENTION

The first embodiment of the present invention will now be explained with reference to the accompanying figures.

Figure 1:
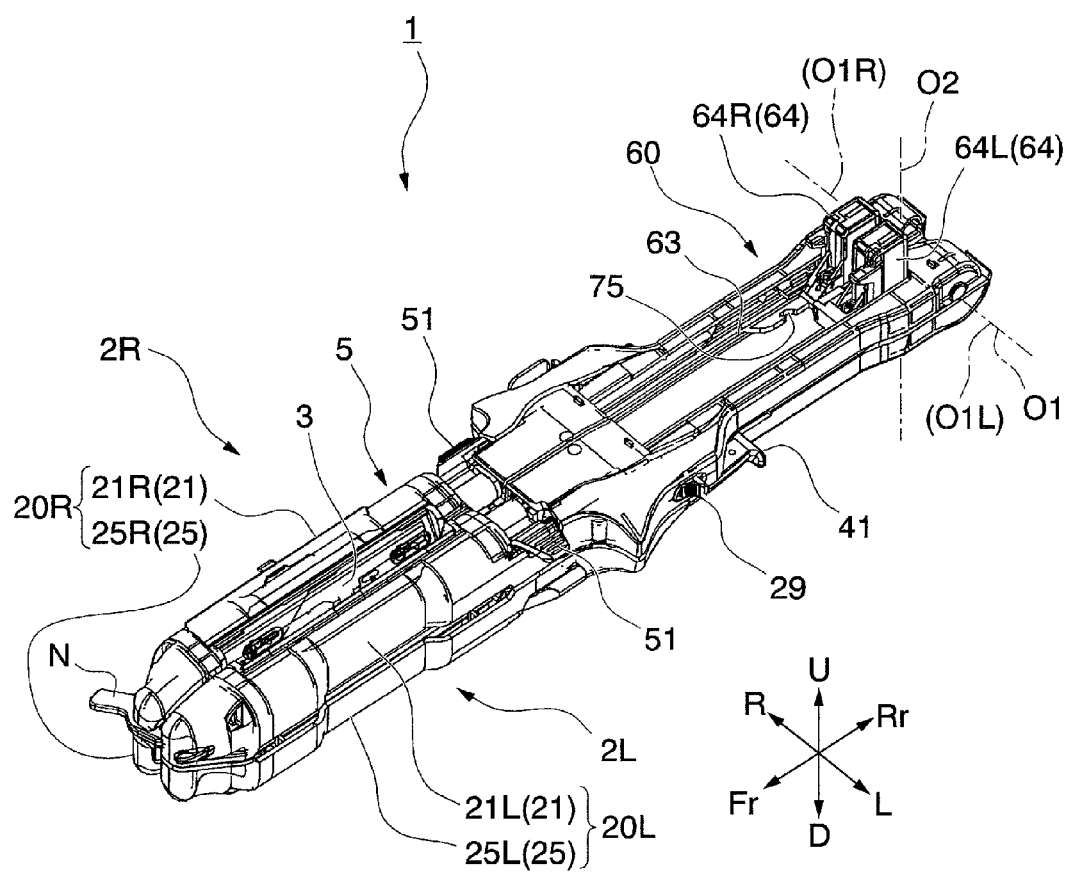
FIG. 1 is a perspective view showing a first embodiment of the anastomotic apparatus according to the present invention, with the view showing the two sets of clamps in the closed state.
Figure 2:
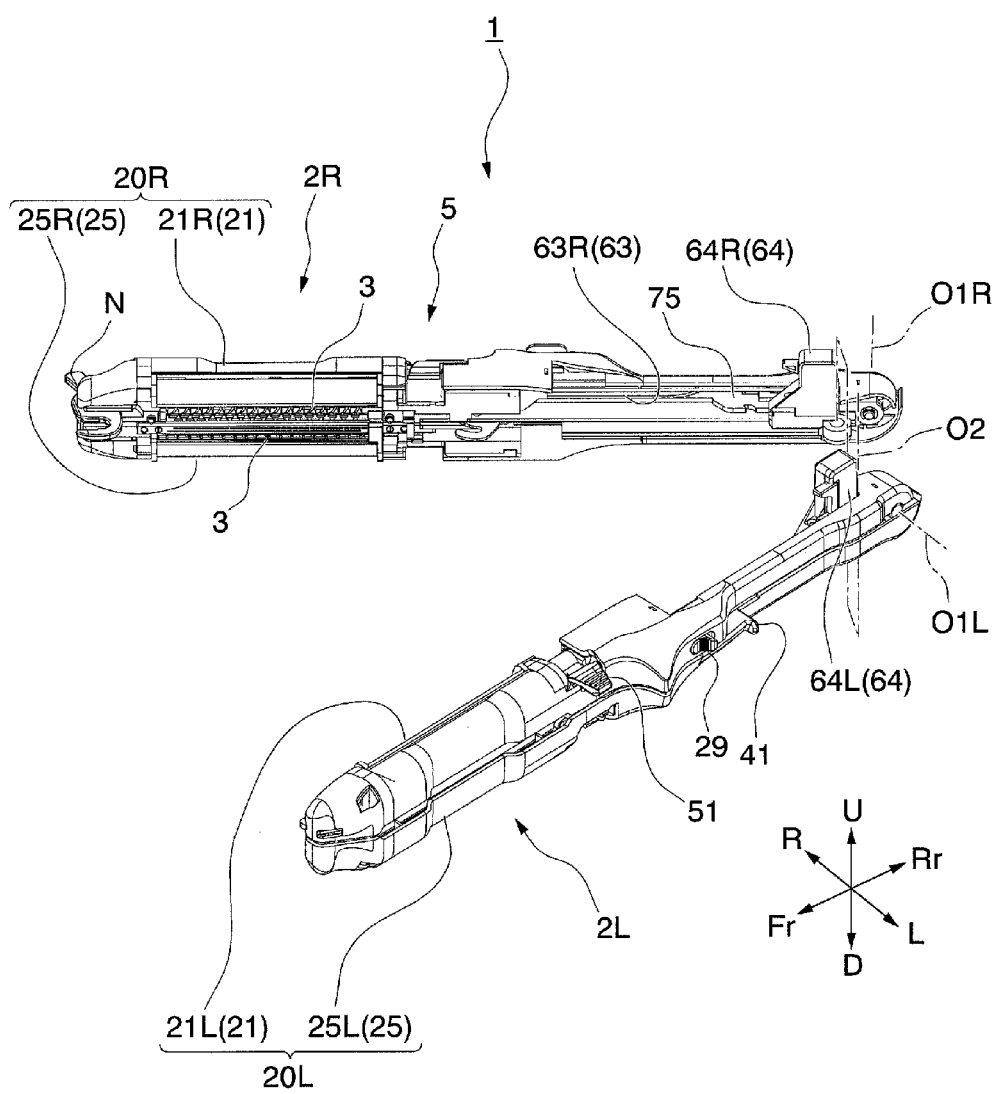
FIG. 2 is a perspective view showing a first embodiment of the anastomotic apparatus according to the present invention, with the view showing the two sets of clamps in the spread open state.
Figure 3:
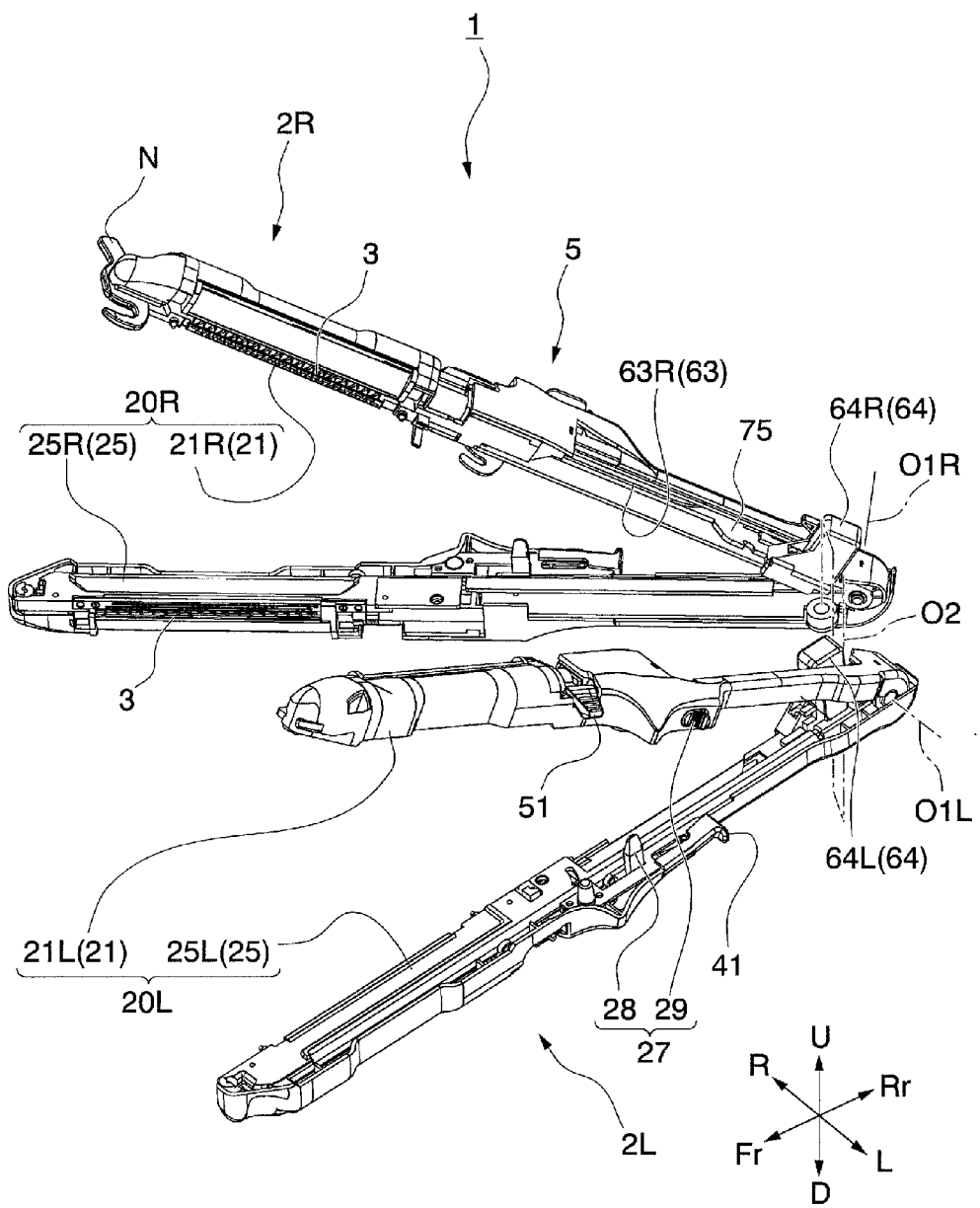
FIG. 3 is a perspective view showing a first embodiment of the anastomotic apparatus according to the present invention, with the view showing the two pairs of clamps in the separated state.

FIGS. 1 through 3 are views showing the anastomotic apparatus according to the present invention. The numeric symbol 1 indicates the anastomotic apparatus while numeric symbols 2R and 2L indicate the clamps.

Figure 4:
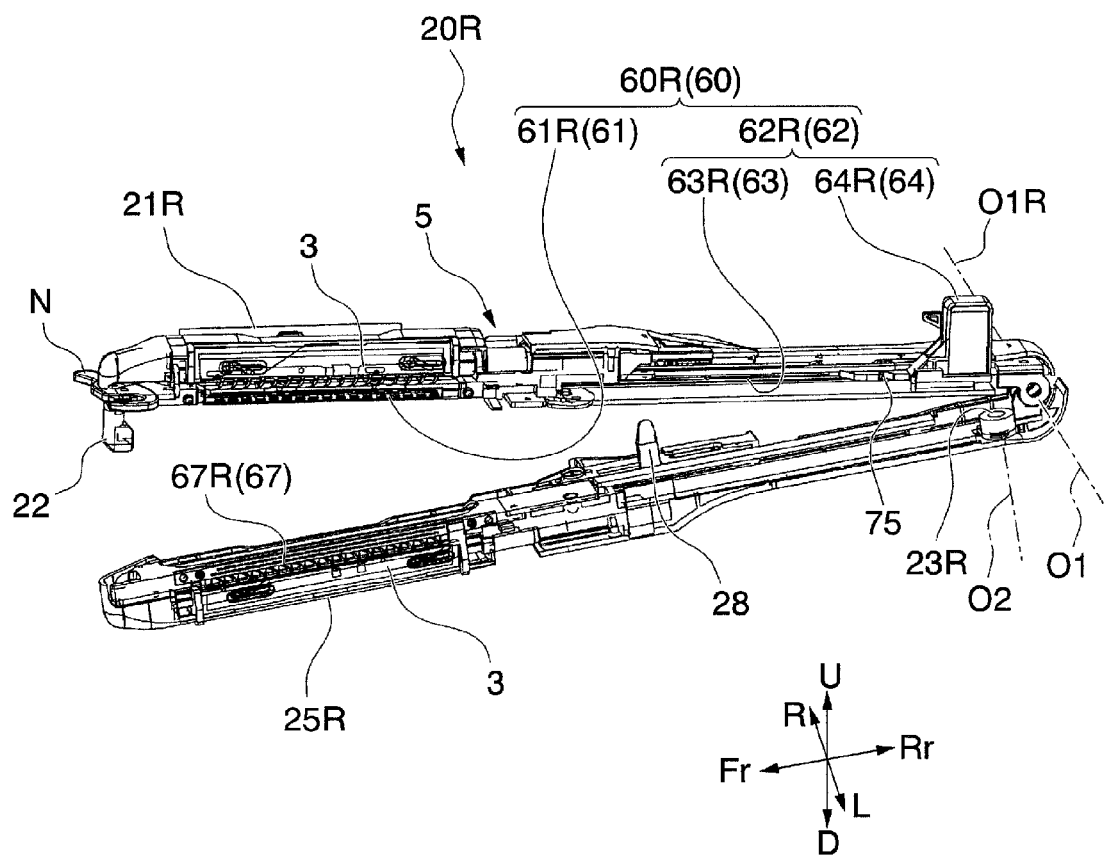
FIG. 4 is a perspective view showing the right-sided clamp in the anastomotic apparatus according to a first embodiment of the present invention.
Figure 5:
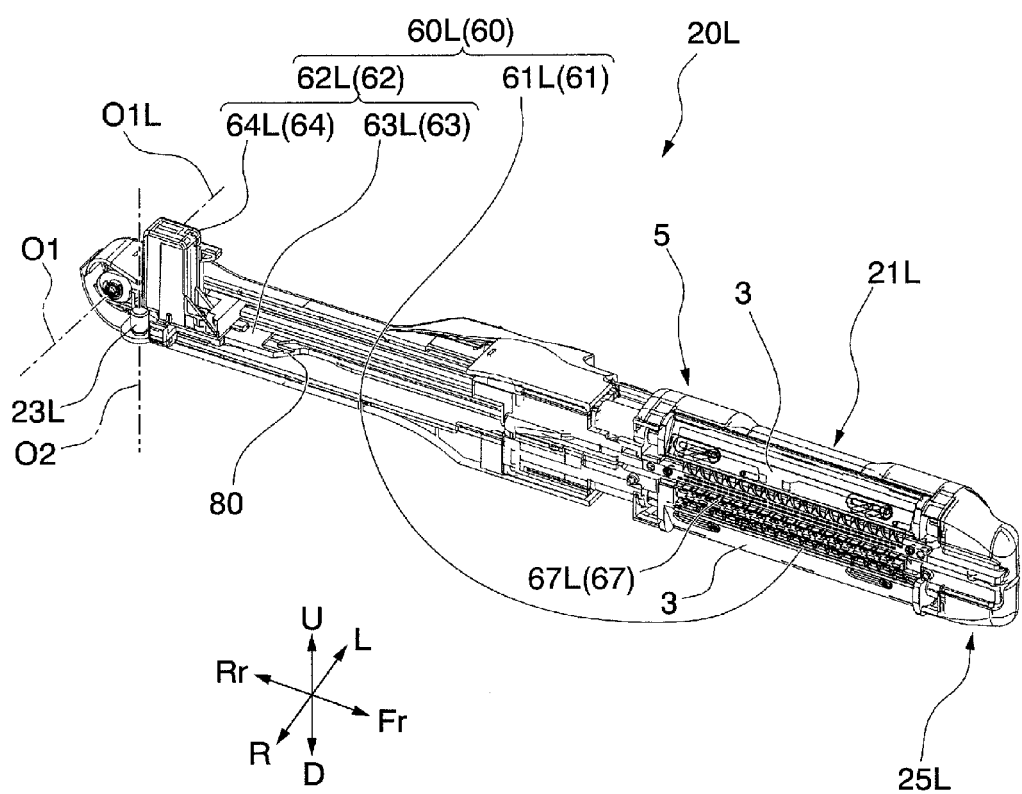
FIG. 5 is a perspective view showing the left-sided clamp in the anastomotic apparatus according to a first embodiment of the present invention.
Figure 6:
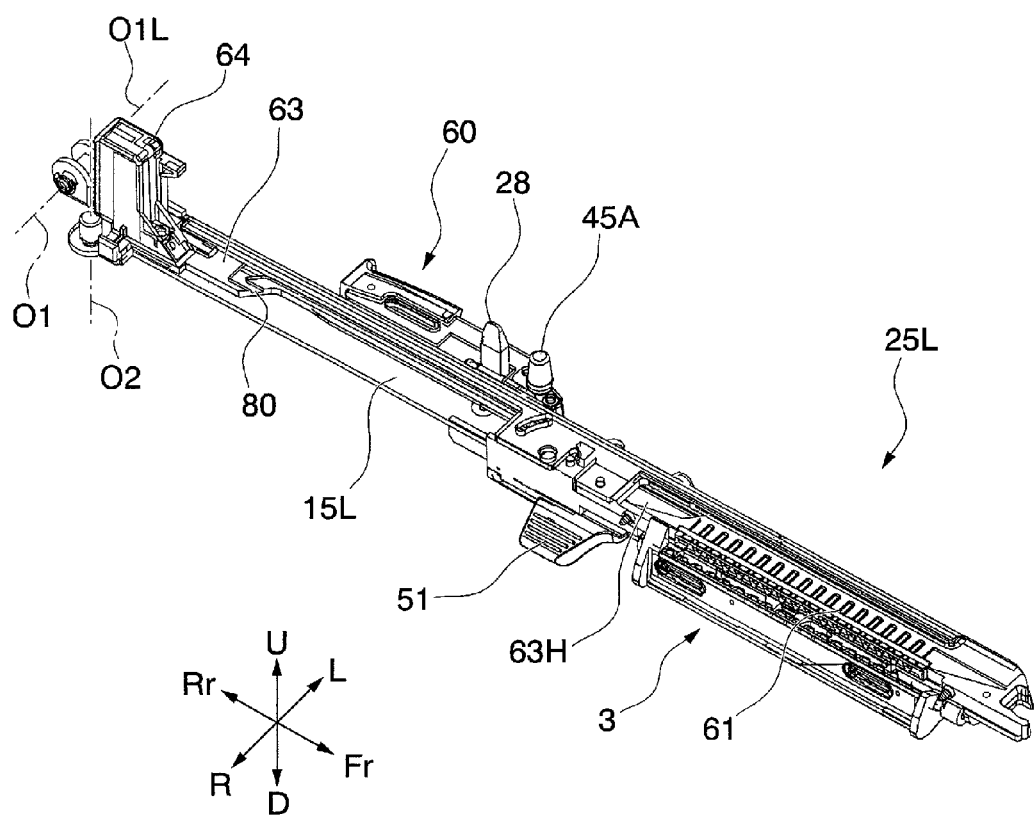
FIG. 6 is a perspective view showing one part of the left-sided clamp member in the anastomotic apparatus according to a first embodiment of the present invention.

FIGS. 4 and 5 show paired clamp members 20R (composed of clamp member 21R and clamp member 25R) which form clamp 2R, and paired clamp members 20L (composed of clamp member 21L and clamp member 25L) which form clamp 2L. FIG. 6 shows clamp member 25L.

The numeric symbols R, L, Fr, Rr, U and D on the coordinate axes shown in FIGS. 1 through 6 indicate direction associated with the anastomotic apparatus 1 and its composing members, with right (R), left (L), Fr (distal end side), up (U) and down (D) indicated for the case when the rear side Rr (referred to as the "handheld side" hereinafter) of the anastomotic apparatus 1 is held in the hand.

As shown in FIGS. 1 through 3, the anastomotic apparatus 1 is provided with a clamp 2R which can rotate around the axis O1R and a clamp 2L which can rotate around the axis O1L.

The clamps 2R and 2L can rotate around the axes O1R, O1L, respectively.

The clamp 2R and clamp 2L can be joined by inserting a connecting pin 23L, which is formed on the same axis as axis O2 which is perpendicular to the axis O1L, formed to clamp 2L, into a connecting hole 23R, which is formed to the same axis as axis O2 which is perpendicular to the axis O1R formed to clamp 2R. Clamp 2R and clamp 2L can mutually rotate around the axis O2.

When the clamp 2R and the clamp 2L are connected and are closed by rotating around the axis O2, then the axis O1R of clamp 2R and the axis OIL of the clamp 2L are designed to be disposed along the one axis O1. Note that the axis O1 and the axis O2 do not signify absolute coordinates in space. Rather they are axes standardized to anastomotic apparatus 1 when it is formed with the clamps 2R,2L closed.

As shown in FIG. 4, the clamp 2R is provided with a clamp member 21R and a clamp member 25R. These clamp members 21R and 25R are respectively provided with a fork which is formed extending in the stapling direction when the device is employed as anastomotic apparatus 1; an organ gripping mechanism 3 which is disposed to the longitudinal direction of clamp members 21R,25R; an everting mechanism 5 which varies the arrangement of the organ gripping mechanism 3 in cross-section perpendicular to the longitudinal direction of the clamp members 21R,25R, and everts the edges of the organ tissue gripped by the organ gripping mechanism 3; a firing mechanism 60 and an anvil member 67; and a grip controlling mechanism.

Further, the clamping surface of the clamp member 21R and the clamping surface of the clamp member 25R are formed to enable opposition of the surfaces, and to enable holding of the organ tissue by closing the clamp member 21R and the clamp member 25R.

As shown in FIG. 5, the clamp 20L is provided with a clamp member 21L and a clamp member 25L. Clamp members 21L and 25L are respectively provided with a fork which is formed extending in the stapling direction when the device is employed as anastomotic apparatus 1; an organ gripping mechanism 3 which is disposed to the longitudinal direction of clamp members 21L,25L; an everting mechanism 5 which varies the arrangement of the organ gripping mechanism 3 in cross-section perpendicular to the longitudinal direction of the clamp members 21L,25L, and everts the edges of the organ tissue gripped by the organ gripping mechanism 3; a firing mechanism 60 and an anvil member 67; and a grip controlling mechanism.

Further, the clamping surface of the clamp member 21L and the clamping surface of the clamp member 25L are formed to enable opposition of the surfaces, and to enable holding of the organ tissue by closing the clamp member 21L and the clamp member 25L.

Note that the clamp 2R and the clamp 2L are designed to be able to close about the axis O2 when an everting operation has been performed for each of the everting mechanisms 5 provided respectively to the clamp members 21R, 25R, 21L, 25L.

Further, the clamps 2R and 2L are designed to form two groups of mutually opposing clamp member pairs, clamp member pair 21 and clamp member pair 25, when the anastomotic apparatus 1 is closed about the axis O2.

The surface which faces the space between the clamp member 21R and the clamp member 21L, which form clamp member pair 21, and the space between clamp member 25R and clamp member 25L, which form the clamp member pair 25, forms the staple facing surface (stapling surface).

Once the anastomotic apparatus 1 is formed, a stapling mechanism provided with a firing mechanism 60 and an anvil member 67 is formed respectively between the mutually opposing clamp member 21R and clamp member 21L, and clamp member 21L 25L and clamp member 25R, with the firing mechanism 60 being disposed to the clamp member 21R and the clamp member 25L, and the anvil member 67 being disposed to the clamp members 21L and 25R.

FIG. 6 shows the abbreviated structure of the firing mechanism 60 that is disposed to the clamp member 25L of the clamp 2L. The firing mechanism 60 is provided with a staple housing 61 for housing the staples S, and an ejector 62.

The clamp members 21R,25R of the clamp 2R and the clamp members 21L, 25L of the clamp 2L are each covered by an externally visible cover of lightweight plastic resin which does not react with the organ tissue.

Figure 7:
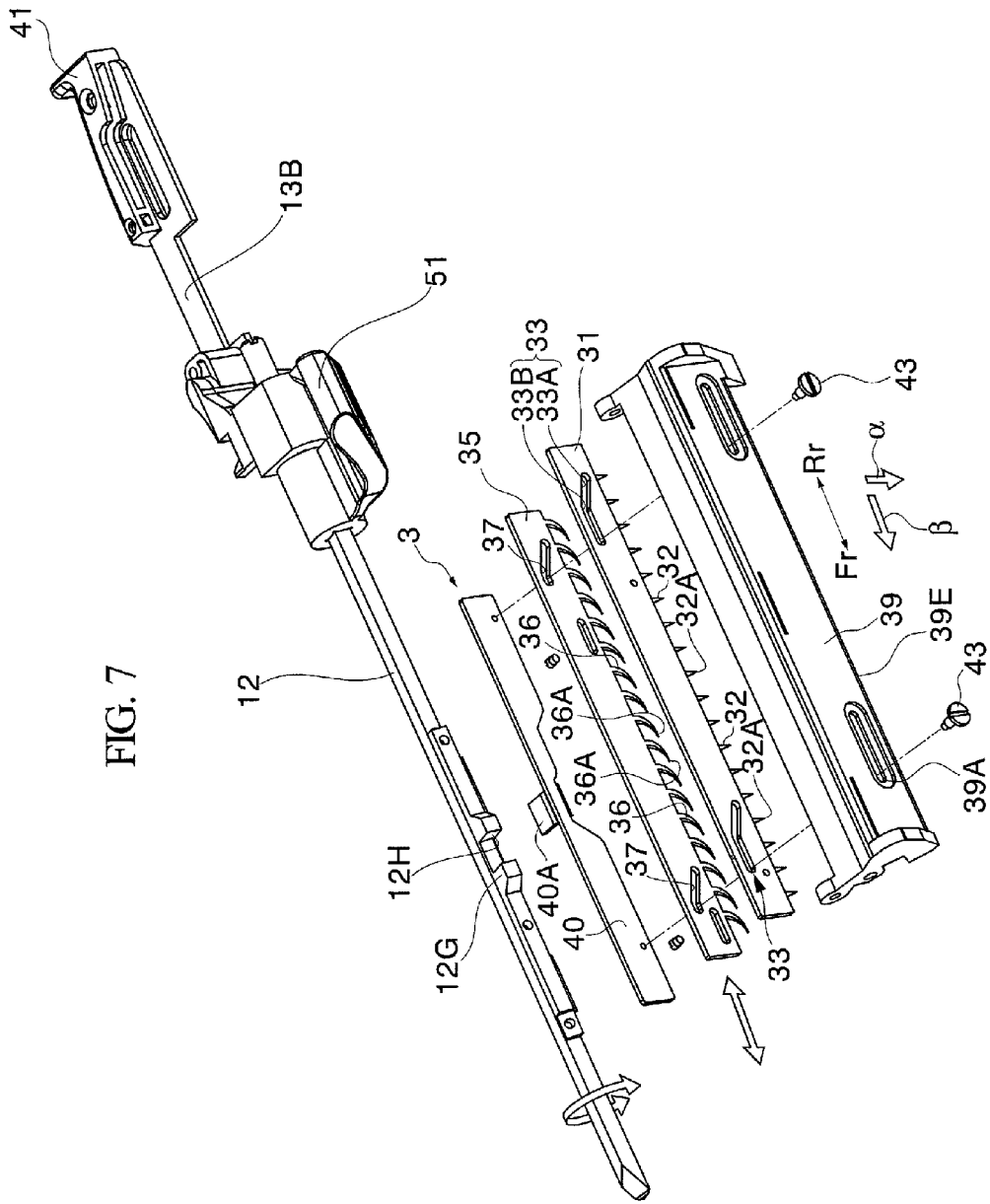
FIG. 7 is a perspective view showing the organ gripping mechanism in the anastomotic apparatus according to a first embodiment of the present invention.

As shown in FIG. 7, the organ gripping mechanism 3 is provided with a pointed teeth member (first gripping teeth plate member) 31, a rake teeth member (second gripping teeth plate member) 35, a housing 39, a gripping teeth operating member (gripping teeth actuating member) 40, and an engaging pin (first engaging member, second engaging member) 43. Housing 39, pointed teeth member 31, rake teeth member 35, and gripping teeth operating member 40, are disposed from the front surface (stapling surface side) in this order overlying one another, and are designed to grip about the stapling site on the organ tissue. Further, the housing 39 is capable of holding the pointed teeth member 31 and the rake teeth member 35, including the tips 32A of the pointed teeth 32 and the tips 36A of the rake teeth 36, so that exposure of the tip side of the pointed teeth 32 and the rake teeth 36 is prevented.

Note that in this embodiment, the term "piercing direction" refers to the direction in which the pointed teeth are pressed against the outside of the organ tissue (i.e., the direction in which the pointed teeth move).

The pointed teeth member 31 and the rake teeth 36 are disposed in an arrangement in which the rake teeth 36 are retracted by one pitch (i.e., the space interval between pointed teeth 32) toward the hand-held side with respect to the pointed teeth 32. When the rake teeth 36 are advanced by one pitch, the tip 36A of a rake tooth 36 is designed to roughly coincide (match) with the tip 32A of the pointed tooth 32 which is one pitch ahead.

The pointed teeth member 31 consists of a plate-shaped member, wherein, for example, a plurality of straight needle-shaped pointed teeth 32 are disposed at equal pitch in a comb-like form, and first engaging cutouts 33 are formed to the pointed teeth member 31. Further, in the first engaging cutout 33 there is formed a first slanted cutout 33A, which, when progressing from the hand-held side (one side) to the distal end side (other side) along the direction of the pointed teeth 32 array, is slanted toward the side of the pointed teeth member 31 which is separated from the pointed teeth 32, and an escape 33B, which extends along the direction of the array from the first slanted cutout 33A toward the distal end side.

Rake teeth member 35 consists of a plate-shaped member which is disposed parallel to the pointed teeth member 31, wherein, for example, a plurality of hooked needle-shaped rake teeth 36 are formed corresponding to the various pointed teeth 32 and disposed at equal pitch to corresponding pointed teeth 32. Further, second engaging cutouts 37 are formed which, when progressing from one side to the other side of the rake teeth member 35, slant toward the side of rake teeth member 35 which is away from the rake teeth 36. In this embodiment, a design is provided in which the rake teeth 36 are formed so that the distal end side thereof is directed toward the distal end side of the clamp members 20R,20L, and the organ tissue P is gripped by advancing the rake teeth 36 by one pitch with respect to the pointed teeth 32, so that the rake teeth 36 are caught on the organ tissue P which is pierced by the pointed teeth 32.

The housing 39 is disposed to the front surface side of the pointed teeth member 31 and the rake teeth member 35, and is designed to prevent damage to the pointed teeth 32 and the rake teeth 36 and to prevent contact with the operator by preventing exposure of the tips of the pointed teeth 32 and the rake teeth 36. Further, two long holes 39A are formed aligned in the direction of the pointed teeth 32 array. The engaging pins 43 can move along the long holes 39A.

Two engaging pins 43 are disposed to the gripping teeth operating member 40. By manipulating the operating knob 41, the engaging pins 43 undergo relative displacement with respect to the housing 39, the rake teeth member 35 and the pointed teeth member 31, moving from the handheld side to the distal end side of the clamp members 20R,20L.

The first slated cutout 33A, second engaging cutout 37, and engaging pins 43 form a first drive mechanism. By moving the engaging pins 43 from the handheld side to the distal end side, the pointed teeth 32 and the rake teeth 36 are moved in the direction of arrow α, and become exposed at the edge 39E of the housing 39.

The escape 33B, second engaging cutout 37, and engaging pins 43 form a second drive mechanism. The engaging pins 43 move from the handheld side to the distal end side and are introduced into the escape 33B, engage with the second engaging cutout 37, and move the wall portion on the distal end side of the second engaging cutout 37 from the hand held side to the distal end side. As a result, the rake teeth member 35 and the pointed teeth member 31 undergo relative displacement in the direction of the pointed teeth 32 array, moving the rake teeth 36 in the direction of arrow β. The phase of rake teeth 36 and the pointed teeth 32 is thus changed by one pitch.

Note that in this embodiment, the first drive mechanism and the second drive mechanism are both connected to the operating knob 41 and manipulate operating knob 41. As a result, the rake teeth 36 move one pitch in the longitudinal direction with respect to the pointed teeth 32 and are exposed from the edge 39E of the housing 39.

Figure 8A:
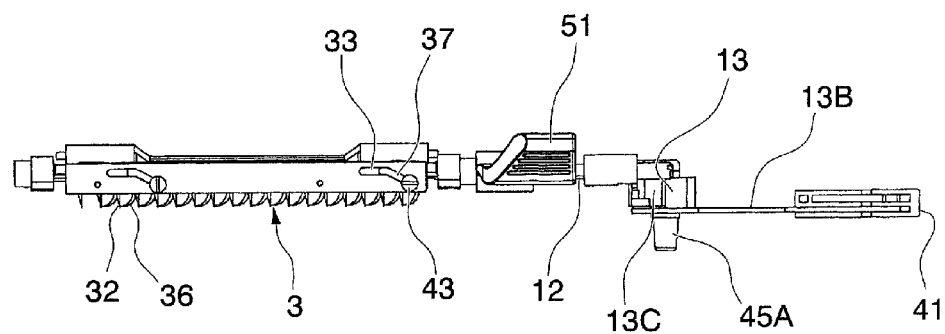
FIG. 8A is a lateral view showing the organ gripping mechanism in the anastomotic apparatus according to a first embodiment of the present invention.
Figure 8B:
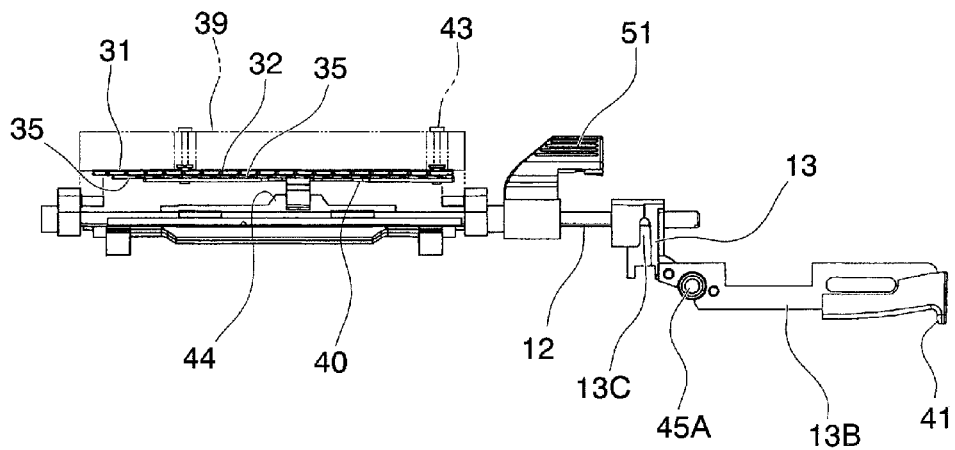
FIG. 8B is a planar view showing the organ gripping mechanism in the anastomotic apparatus according to a first embodiment of the present invention.

FIGS. 8A and 8B show an overview of the organ gripping mechanism 3. Gripping teeth operating member 40 is connected to a connecting rod 12 via a connecting member 44. The connecting rod 12 is connected to the connecting member 13B via a UB connector 13. The connecting member 13B is connected to the operating knob 41.

The gripping teeth operating member 40 engages with an engaging recess 12G of the connecting rod 12 via an engaging projection 40A. Note that the engaging recess 12G is designed so that the width of the end surface 12H in the longitudinal direction is formed to be slightly larger than the engaging projection 40A.

As a result, the operating knob 41 is operated to move the connecting rod 12 in the advancing or retracting direction. The gripping teeth operating member 40 advances or retracts as a result, so that the pointed teeth 32 and the rake teeth 36 of the organ gripping mechanism 3 are placed in the gripping state. On the other hand, even if the eversion operating knob 51 is rotated when the everting mechanism 5 is operated, the operating knob 41 undergoes relative displacement in the direction of rotation of the eversion operating knob 51, thus preventing rotation of the operating knob 41.

The connecting rod 12 is inserted in the axial direction of the eversion operating knob 51, explained below, to allow sliding. By moving the operating knob 41 from the handheld side toward the distal end side (from right to left in FIG. 8A) as shown in FIG. 8B, the pointed teeth 32 and the rake teeth 36 move in the direction which exposes them from the edge 39E of the housing 39 in the organ gripping mechanism 3.

The part of the connecting rod 12 that is inserted into the eversion operating knob 51 is formed in the shape of a square column, for example. Rotation of the eversion operating knob 51 causes rotation of the connecting rod 12, so that the everting mechanism 5 places the pointed teeth 32 and the rake teeth 36 of the organ gripping mechanism 3 in the everting arrangement.

The rotation of the eversion operating knob 51 is not communicated to the UB connector 13.

The action of the organ gripping mechanism 3 will now be explained with reference to FIGS. 9A, 9B and 9C.

Figure 9A:
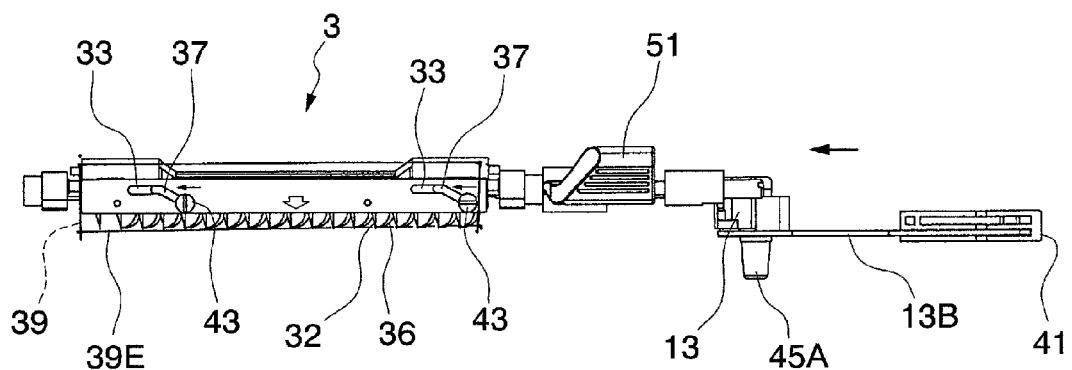
FIG. 9A is a view for explaining the action of the organ gripping mechanism in the anastomotic apparatus of the present invention, and shows the pre-operation state.

First, the operating knob 41 is manipulated (moved from the right to the left side in FIG. 9A), moving the connecting member 13B as shown in FIG. 9A. As a result, the connecting rod 12 advances so that the engaging pins 43 engage with the inclined parts of the first slanted cutout 33A of the pointed teeth member 31 and the second engaging cutout 37 of the rake teeth member 35.

Figure 9B:
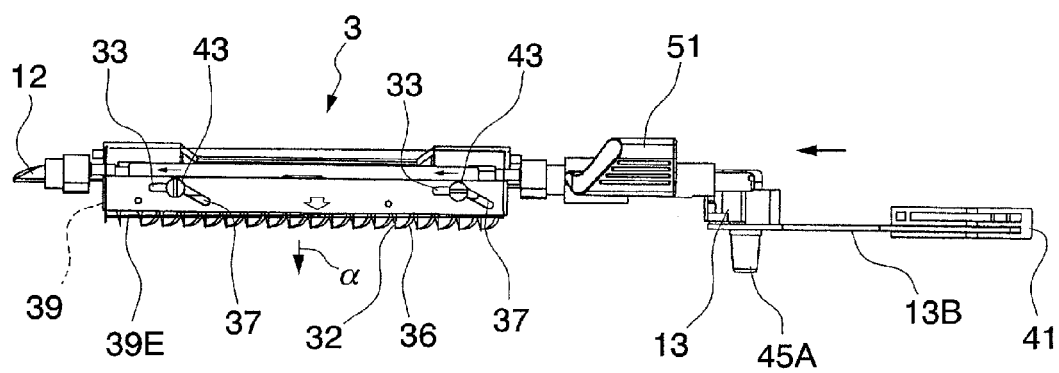
FIG. 9B is a view for explaining the action of the organ gripping mechanism in the anastomotic apparatus of the present invention, and shows the state during operation.

Next, the connecting member 13B is moved further as shown in FIG. 9B, so that the engaging pins 43 move along the inclined parts of the first slanted cutout 33A of the pointed teeth member 31 and the second engaging cutout 37 of the rake teeth member 35. The pointed teeth 32 and the rake teeth 36 move in the direction of arrow α, and are exposed from the edge 39E of the housing 39.

Figure 9C:
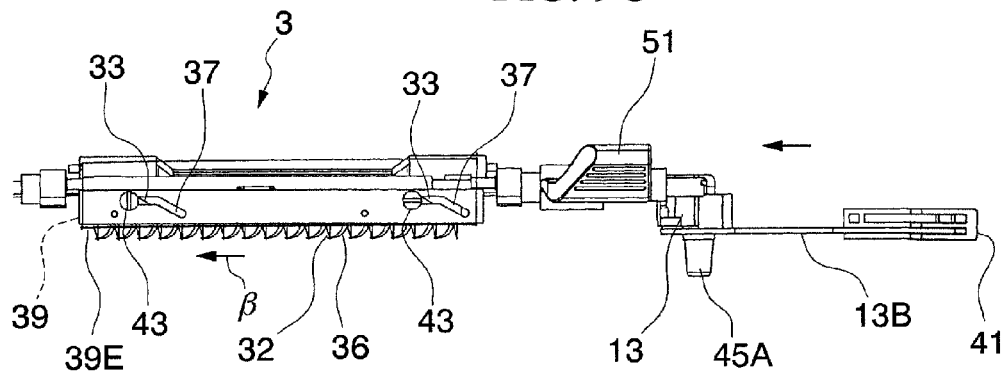
FIG. 9C is a view for explaining the action of the organ gripping mechanism in the anastomotic apparatus of the present invention, and shows the post-operation state.

Next, as shown in FIG. 9C, the engaging pins 43 are guided in the escape 33B of the pointed teeth member 31, engaging with the second engaging cutout 37 of the rake teeth member 35 and pressing against the wall portion on the distal end side of the second engaging cutout 37. When the rake teeth member 35 and the pointed teeth member 31 undergo relative displacement, the rake teeth 36 move in the direction of arrow β, and the phase of the rake teeth 36 and the pointed teeth 32 changes by one pitch.

Note that the first and second gripping teeth plate members may be designed so that the gripping teeth drive is connected to at least one of the first gripping teeth plate member and the second gripping teeth plate member to enable mutual relative displacement.

Figure 10:
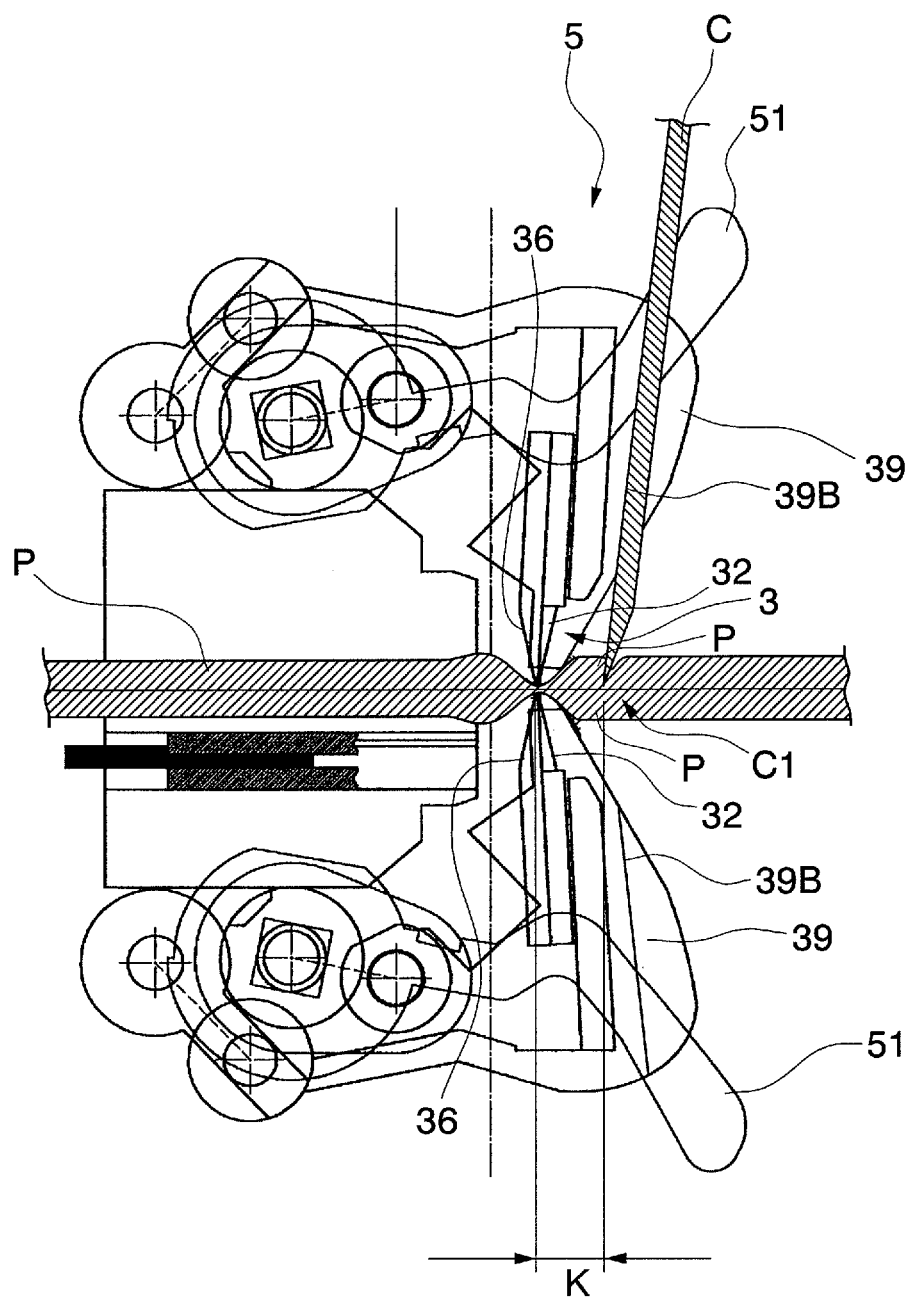
FIG. 10 is a view showing an example of the cut protector in the anastomotic apparatus of the present invention.

As shown in FIG. 10, a cut protector (guide for incising the organ tissue) 39B is formed to the housing 39. This cut protector 39B is for cutting the organ tissue with a cutting blade C while maintaining a suitable distance from the stapling site when the organ tissue P is anastomosed on the front surface (where the end of the organ tissue P is present), and designating as the cut end a position removed a specific interval K from the position corresponding to the stapling site (tip 32A of the pointed teeth 32 here).

By moving cutting blade (a scalpel blade, for example) C along the cut protector 39B, the cutting area C1 at the tip of the cutting blade C can easily cut and separate an area near the stapling site (at the optimal site for example) which is separated by a specific interval K from the tip 32A of the pointed teeth 32.

As a result, an excess or insufficiency of organ tissue P near the stapling site can be prevented and the anastomosis of the organ tissue P can be carried out stably and efficiently. Note that the cut protectors 39B ideally intersect such that their gripping teeth tip sides form an angle in the range of 10° to 45° with respect to the direction in which the pointed teeth 32 extend.

Figure 11A:
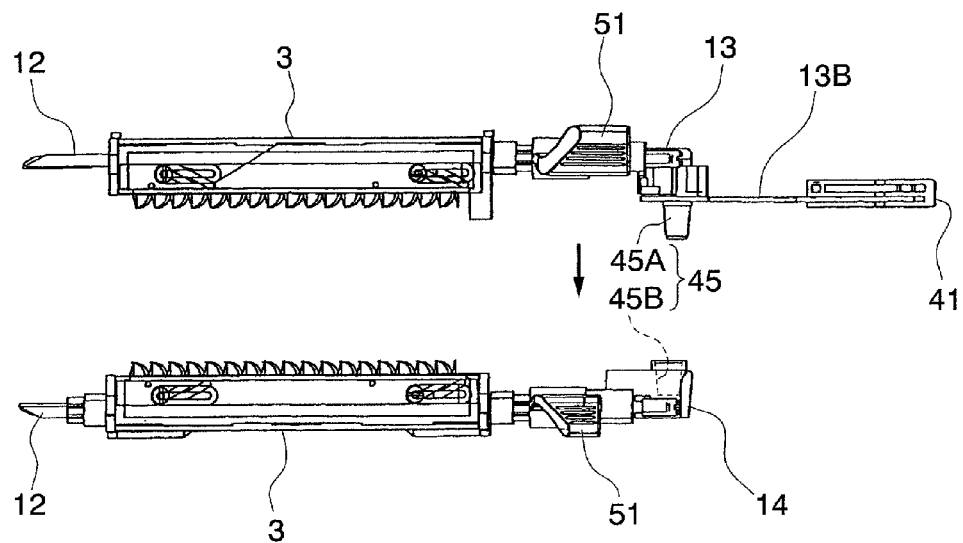
FIG. 11A is a view for explaining the gripping action synchronizing mechanism in the anastomotic apparatus according to a first embodiment of the present invention, and shows the pre-synchronization state.

Further, as shown in FIG. 11A, a synchronizing projection 45A is formed to the UB connector 13 of one of the clamp members of the respective clamps 2R,2L, while a synchronizing recess 45B is formed to the connector 14 which corresponds to the UB connector 13 and is disposed to the other clamp member.

The synchronizing projection 45A and the synchronizing recess 45B form a gripping action synchronizing mechanism 45 for synchronizing and moving the organ gripping mechanism 3.

Figure 11B:
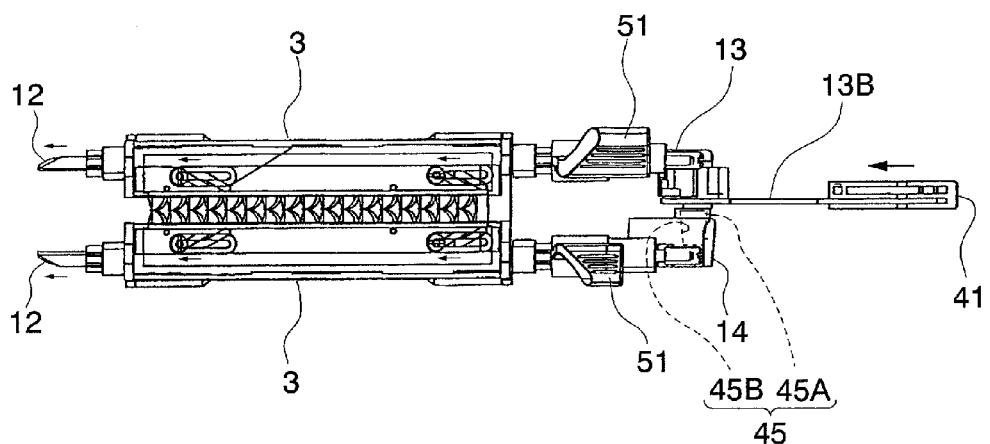
FIG. 11B is a view for explaining the gripping action synchronizing mechanism in the anastomotic apparatus according to a first embodiment of the present invention, and shows the synchronized state.

As a result, as shown in FIG. 11B, the synchronizing projection 45A is inserted into the synchronizing recess 45B by closing the clamps 2R,2L. As a result, the corresponding two organ gripping mechanisms 3 are driven in synchronization with the organ tissue P held between the clamping surfaces, and the pointed teeth 32 and the rake teeth 36 are driven in synchronization.

The everting mechanism 5 is designed so that an eversion operating knob (everting operator) 51 for everting the organ gripping mechanism 3 through remote operation, and a link 53, whose arrangement when viewed from the direction of the longitudinal axis of the anastomotic apparatus 1 is changed through rotation of the connecting rod 12 in a direction intersecting the longitudinal direction of the fork, are employed to move the organ gripping mechanism 3 within an eversion movement range which extends from a pre-eversion position, at which piercing near the stapling site occurs, to a post-eversion position, at which the stapling site on the organ tissue is positioned on the stapling surface. Note that an engaging part, not shown in the figures, is provided in between the eversion operating knob 51 and the clamp members 21R, 21L, 25R, 25L, for stopping the everting mechanism 5 at the pre-eversion position and the post-eversion position.

A lock recess is formed in the organ gripping mechanism 3 and a lock projection (not shown) is formed in the eversion operating knob 51. When the everting operation is performed, the lock projection enters the lock recess. When the eversion operating knob 51 is rotated, the lock projection engages with the lock recess, and is held at a position which exposes the pointed teeth 32 and the rake teeth 36 of the organ gripping mechanism 3. At the same time the organ gripping mechanism 3 is held at the post-eversion position, maintaining the everted state.

Figure 12A:
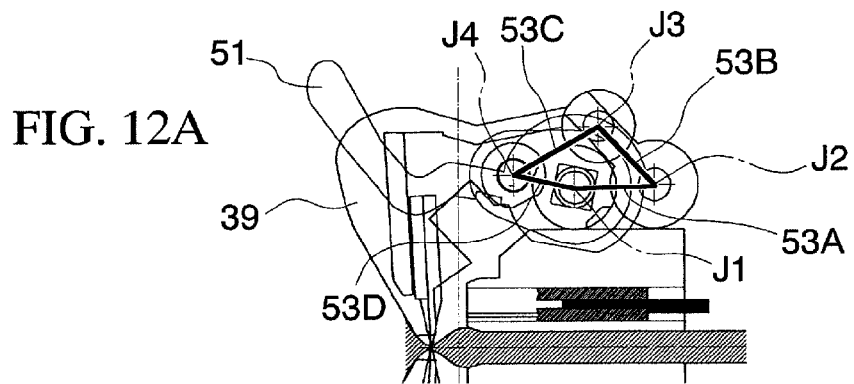
FIG. 12A is a view for explaining the link mechanism composing the everting mechanism in the anastomotic apparatus according to a first embodiment of the present invention, and shows an approximate cross-sectional view as seen along the axial line of the link mechanism.
Figure 12B:
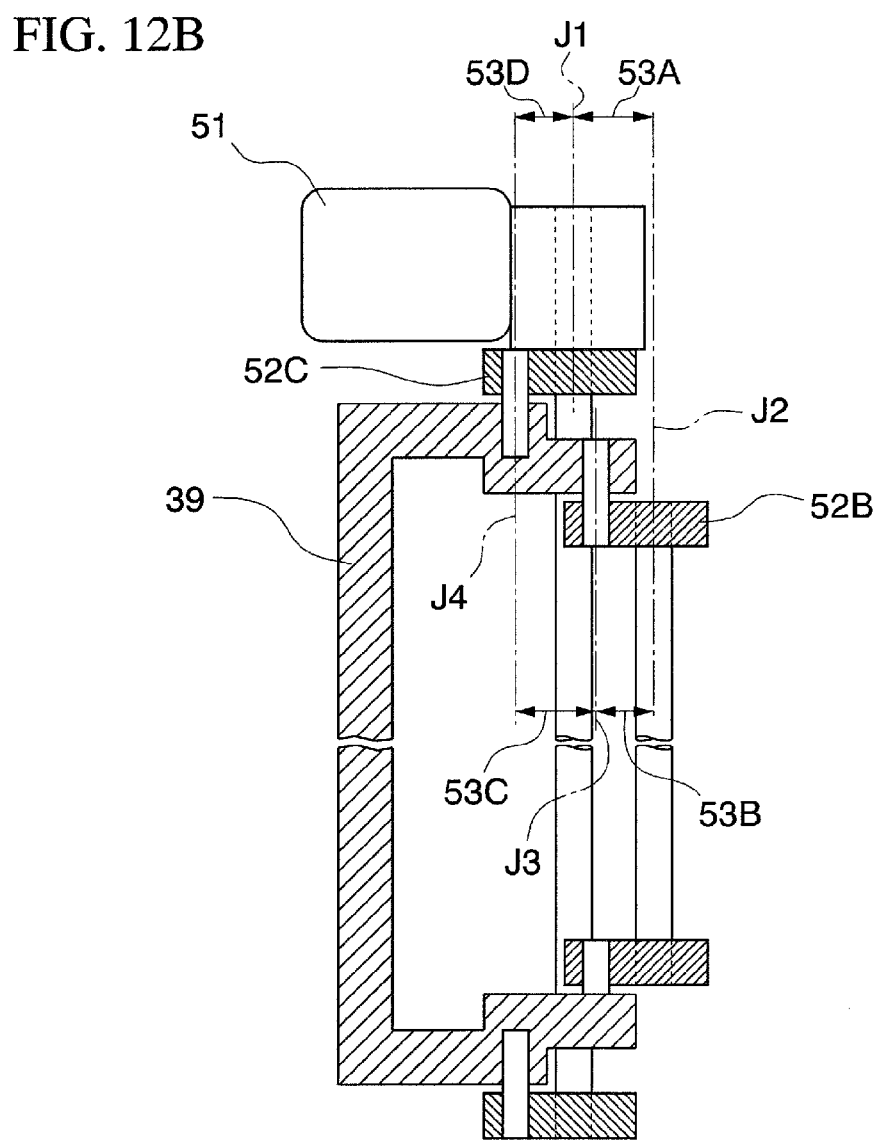
FIG. 12B is a view for explaining the link mechanism composing the everting mechanism in the anastomotic apparatus according to a first embodiment of the present invention, and is an approximate cross-sectional view as seen from the side.

In this embodiment, the link 53 is composed of a plurality (4 or more) of links 53A, 53B, 53C, 53D as shown in FIGS. 12A and 12B. Link 53A is formed in between support point J1 and support point J2, wherein one end of link 53A is designated as support point J1 formed to the main body side of the anastomotic apparatus 1 and formed to coincide with the rotational axis of the connecting rod 12, and the other end of link 53A is designated as support point J2 formed to the link member 52B. By rotating the connecting rod 12 using the eversion operating knob 51, the arrangement of the link 53 is changed and the housing 39 is warped outward.

The link 53B is formed in between support point J2 and support point J3, wherein one end of link 53B is designated as support point J2 formed to the link member 52B, and the other end of link 53B is designated as support point J3 formed to housing 39. The link 53C is formed in between support point J3 and support point J4, wherein one end of link 53C is designated as support point J3 formed to the housing 39, and the other end of link 53C is designated as support point J4 formed in the same way to the housing 39. The link 53D is formed in between the support point J4 and the support point J1 which are each formed to housing 39.

In this embodiment, the everting mechanism 5 forms a square-shaped link 53 formed by links 53A, 53B, 53C, 53D.

Figure 13:
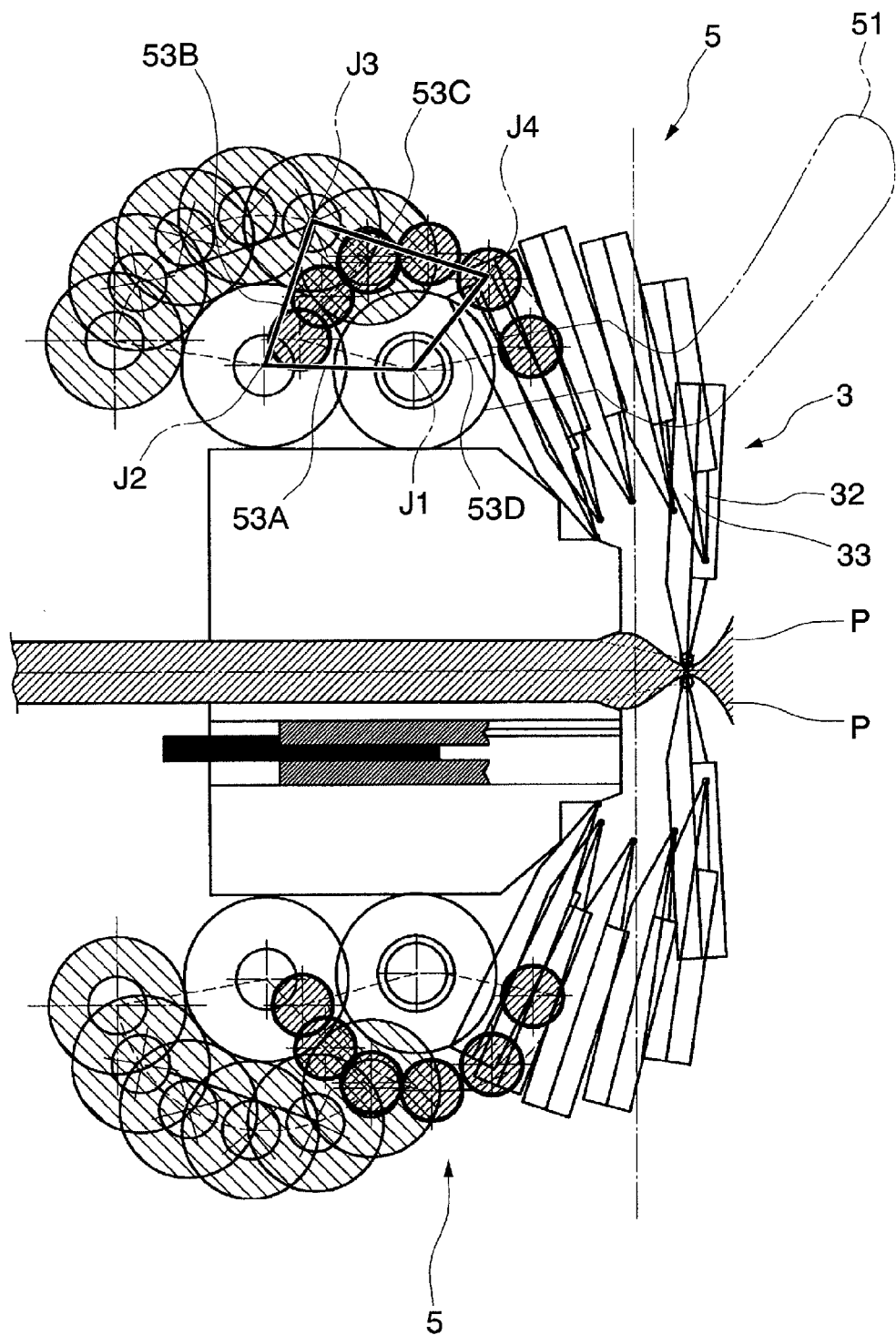
FIG. 13 is a view showing the eversion trajectory of the everting mechanism in the first embodiment.

FIG. 13 is a view showing the trajectory of the eversion of the organ tissue P by everting mechanism 5 consisting of link 53. By providing the above design, eversion of the organ tissue P which is gripped by the organ gripping mechanism 3 can be smoothly carried out with slight force by rotating the eversion operating knob 51, and the stress on the organ tissue P can be reduced by preventing the application of unnecessary pulling force on the organ tissue P during eversion.

Note that other mechanisms consisting of four or more links may be employed for the links forming the everting mechanism 5.

Further, the clamps 2R,2L forming the anastomotic apparatus 1 are provided with a clamp member space maintaining mechanism for adjusting and maintaining the space between the paired clamp members 20R,20L within a specific interval during the eversion, by rotating the eversion operating knob 51.

Figure 14A:
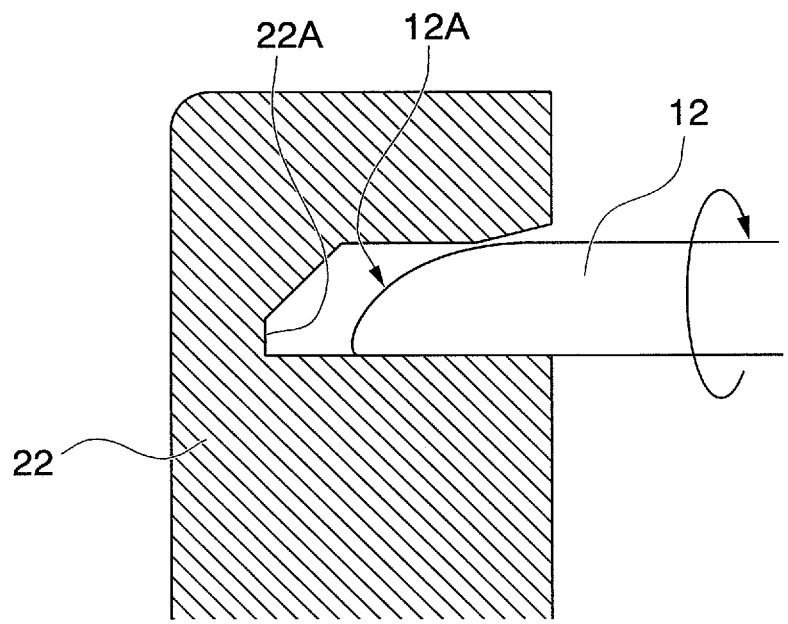
FIG. 14A is a view for explaining an example of the clamp member space maintaining mechanism in the anastomotic apparatus of the first embodiment, and shows the pre-eversion state.
Figure 14B:
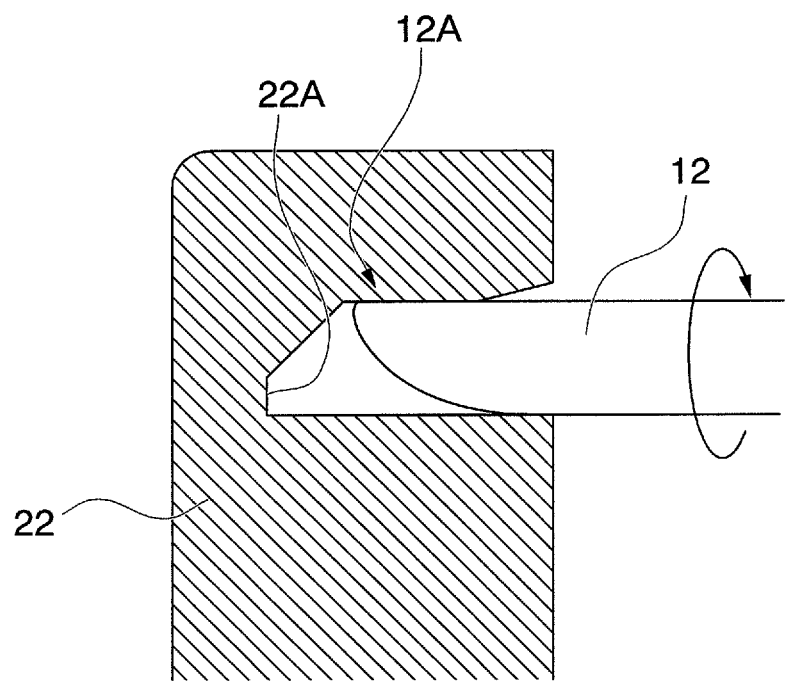
FIG. 14B is a view for explaining an example of the clamp member space maintaining mechanism in the anastomotic apparatus of the first embodiment, and shows the post-eversion state.

As shown in FIGS. 14A and 14B, the clamp member space maintaining mechanism is provided with a fork connecting member 22, which is provided to the distal end side of either one of the clamp members 20 which form the clamp 2, and a connecting rod 12 of the organ gripping mechanism 3 which is disposed to the other clamp member 20. A housing space is formed to the fork connecting member 22 for housing the tip 12A of the connecting rod 12.

The tip 12A of the connecting rod 12 has a tapered surface formed to one side and a flat surface formed to the other side of its distal end. A housing space in the fork connecting member 22 is designed to permit easy insertion of the tip 12A of the connecting rod 12 into the housing space without warping. In addition, an inner wall surface is formed which is pressed by the flat wall part of the tip 12A when the organ gripping mechanism 3 is everted.

As a result, when the organ gripping mechanism 3 is operated by advancing the connecting rod 12 with the clamps 2 in the closed state, the tip 12A is inserted smoothly into the housing of the fork connecting member 22 as shown in FIG. 14A.

When the connecting rod 12 is rotated in this state using the eversion operating knob 51, the inclination of the taper at the tip 12A changes as shown in FIG. 14B, the flat surface of the tip 12A comes into contact with the inner wall surface of the housing and the space between the paired clamp members 20R,20L is adjusted to a specific space interval and maintained.

Further, the respective clamps 2 have a grip controlling mechanism for preventing the pointed teeth member 31 and the rake teeth member 35 from moving relative to one another when the organ gripping mechanism 3 is moved to the post-eversion position side, thereby preventing the everted organ tissue P from slipping free from the organ gripping mechanism 3.

The grip controlling mechanism is provided with a engaging recess 13A which is formed in the UB connector 13, and an engaging projection 51A which is formed to side of the eversion operating knob 51 which is in the advancing direction during an everting manipulation of the eversion operating knob 51. This grip controlling mechanism is realized by insertion of the engaging projection 51A into the engaging recess 13A when the everting operation is performed by rotating the eversion operating knob 51.

Figure 15A:
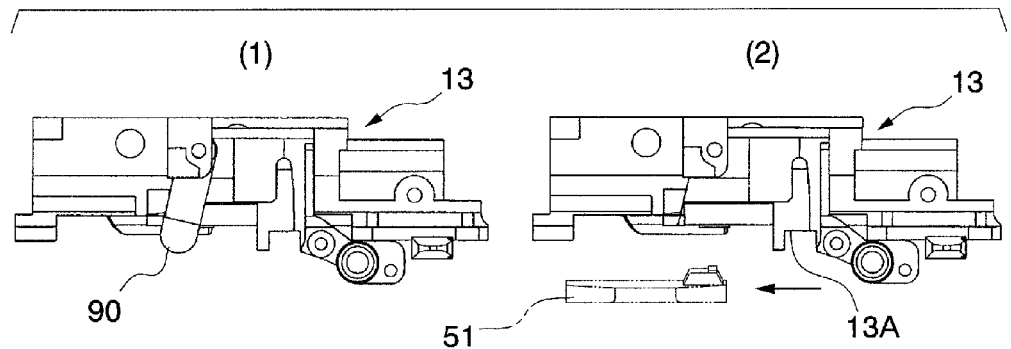
FIG. 15A is a view for explaining an example of the engagement of the organ gripping mechanism using everting knob in the anastomotic apparatus of the first embodiment, and shows the pre-eversion state.

Specifically, as shown in FIGS. 15A (1) and (2), when the organ gripping mechanism 3 is advanced in order to grip the organ tissue P with the pointed teeth 32 and the rake teeth 36, the UB connector 13 also advances.

Figure 15B:
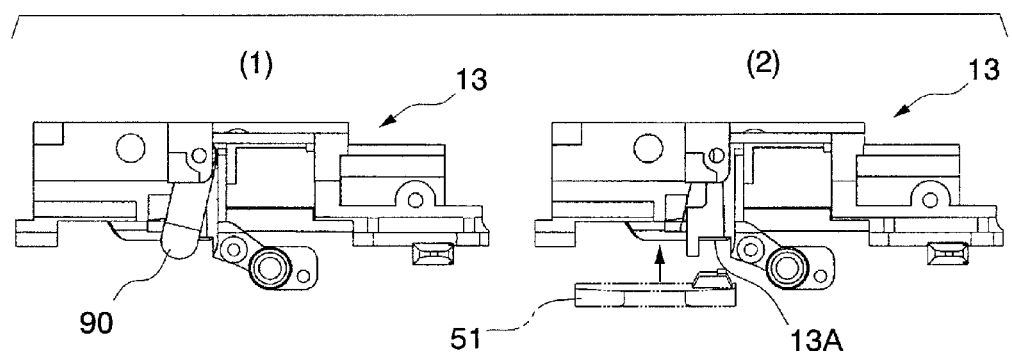
FIG. 15B is a view for explaining an example of the engagement of the organ gripping mechanism using everting knob in the anastomotic apparatus of the first embodiment, and shows the state during the eversion.

Next, as shown in FIGS. 15B (1) and (2), when the UB connector 13 is advanced, the engaging recess 13A reaches the position corresponding to the engaging projection 51A of the eversion operating knob 51.

Figure 15C:
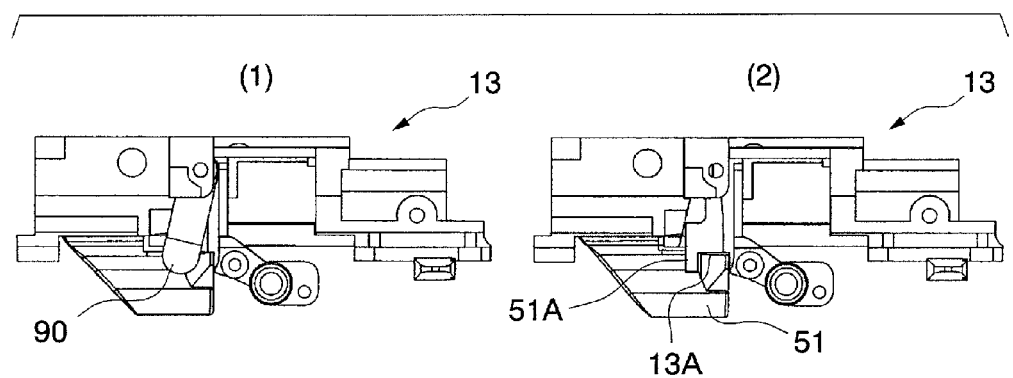
FIG. 15C is a view for explaining an example of the engagement of the organ gripping mechanism using the everting knob in the anastomotic apparatus of the first embodiment, and shows the post-eversion state.

Next, as shown in FIGS. 15C (1) and (2), when the knob 51 is rotated to create the everted state, the engaging projection 51A is inserted into the engaging recess 13A, preventing the retraction of the UB connector 13.

Note that FIG. 15A(1), FIG. 15B(1), and FIG. 15C(1) are figures showing the inclination of the releasing member 90 with respect to the UB connector 13, and the FIG. 15A(2), FIG. 15B(2), and FIG. 15C(2) are figures showing positions relative to the engaging projection 51A of the eversion operating knob 51, with the releasing member 90 omitted therefrom. Further, the eversion operating knob 51 shown by the dashed lines in FIG. 15A(2) and FIG. 15B(2) conceptually shows the relative positions of the engaging projection 51A and the engaging recess 13A.

As a result, the retraction of the UB connector is prevented, and the organ tissue P can be stably held when in the everted state by preventing the pointed teeth 32 and the rake teeth 36 from slipping free from the everted organ tissue P.

Note that the mechanism for stably gripping the organ tissue P when in the everted state may be realized by other mechanisms and the design of the aforementioned mechanism can be optionally selected.

As shown in FIGS. 1 and 2, stapling mechanisms are formed between the two sets of clamp member pairs 21, 25, i.e., clamp member 21R and clamp member 25R forming clamp 2R, and clamp member 21L and clamp member 25L forming clamp 2L, which are mutually opposable between the partnered clamps 2R,2L. The two sets of stapling mechanisms are respectively provided with a firing mechanism 60 and an anvil member 67.

Figure 16:
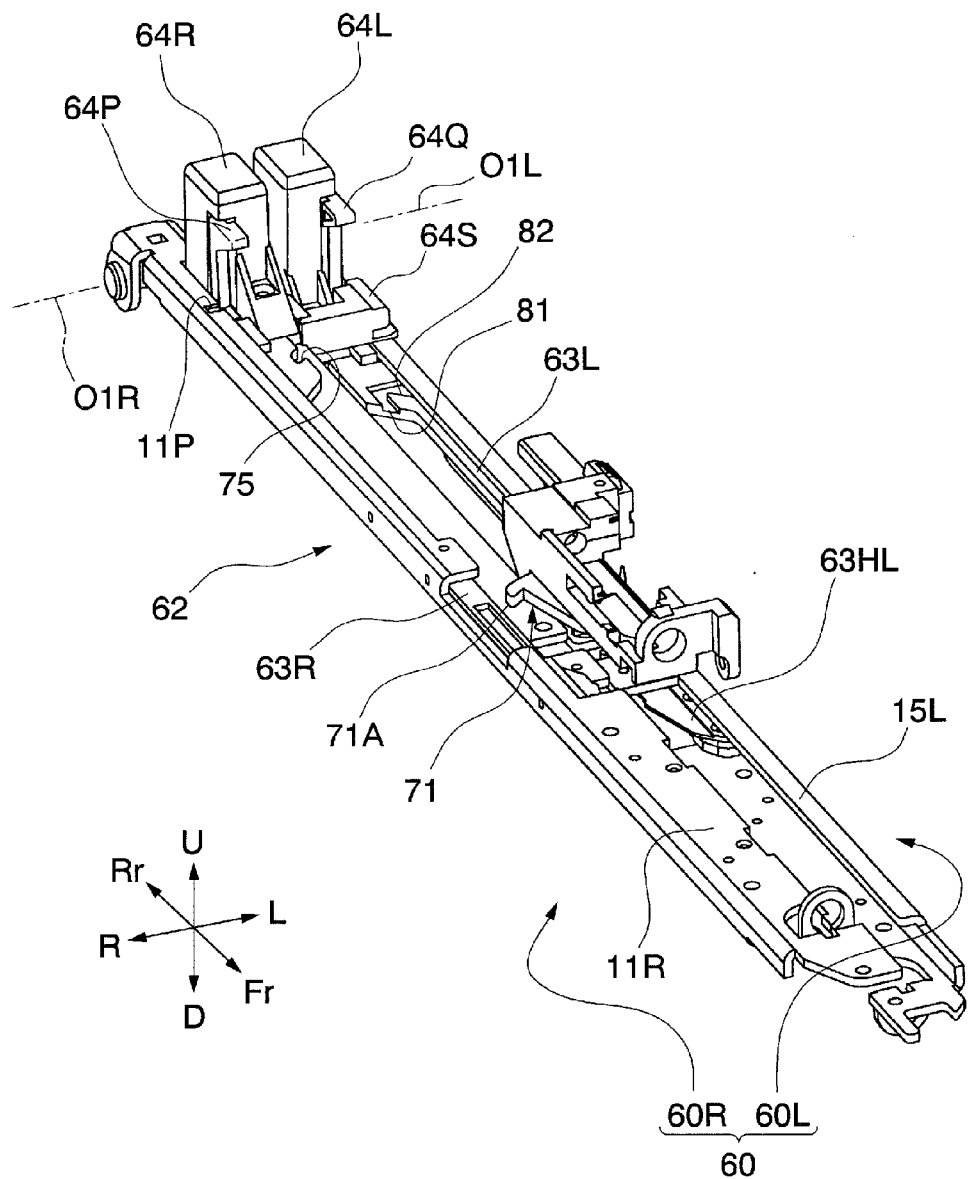
FIG. 16 is a perspective view showing the abbreviated structure of the ejector in the anastomotic apparatus of the present invention.
Figure 17:
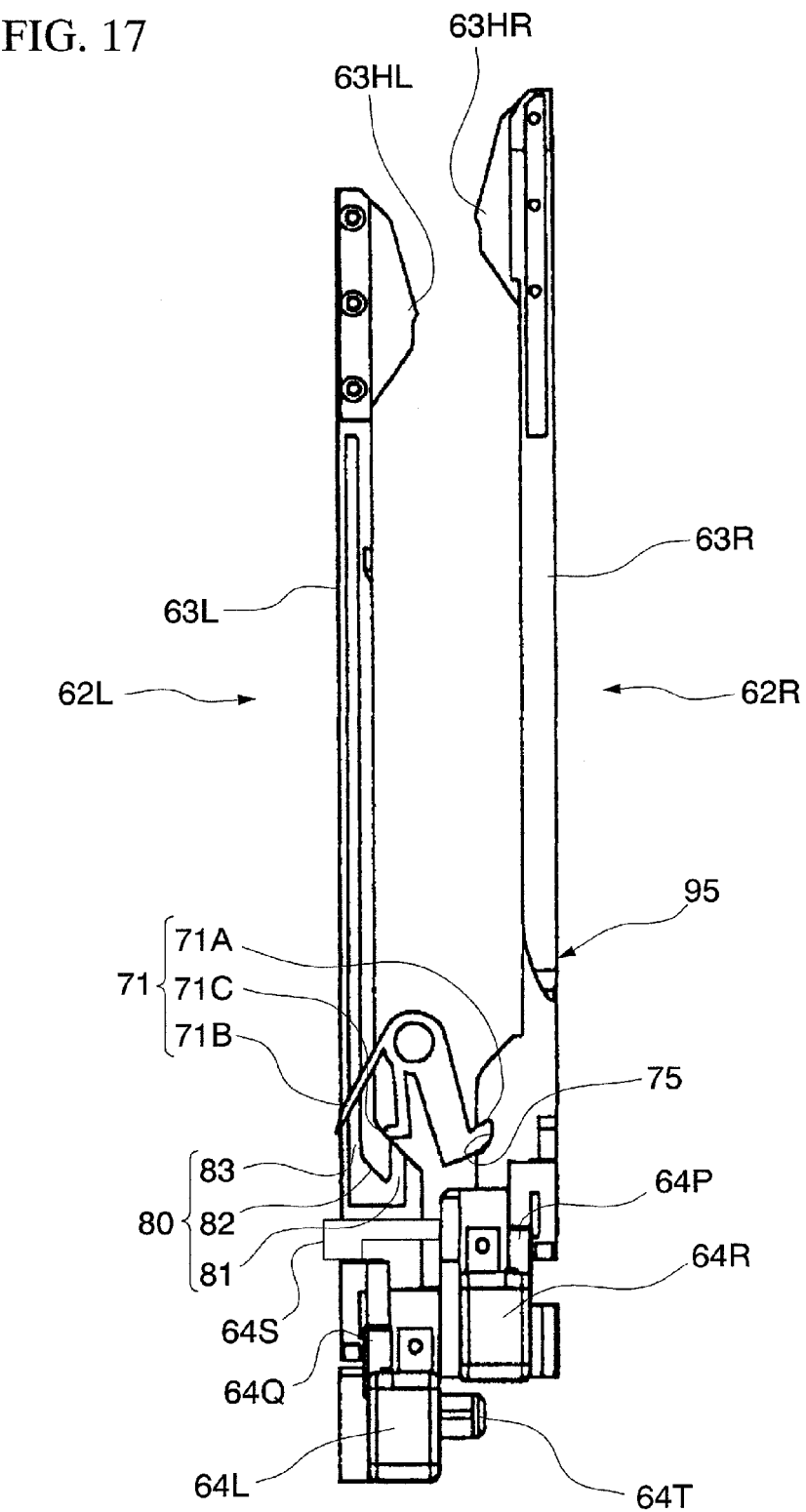
FIG. 17 is a view showing the abbreviated structure of the ejector and the ejection sequence controlling mechanism of the stapling mechanism in the anastomotic apparatus of the present invention.
Figure 18A:
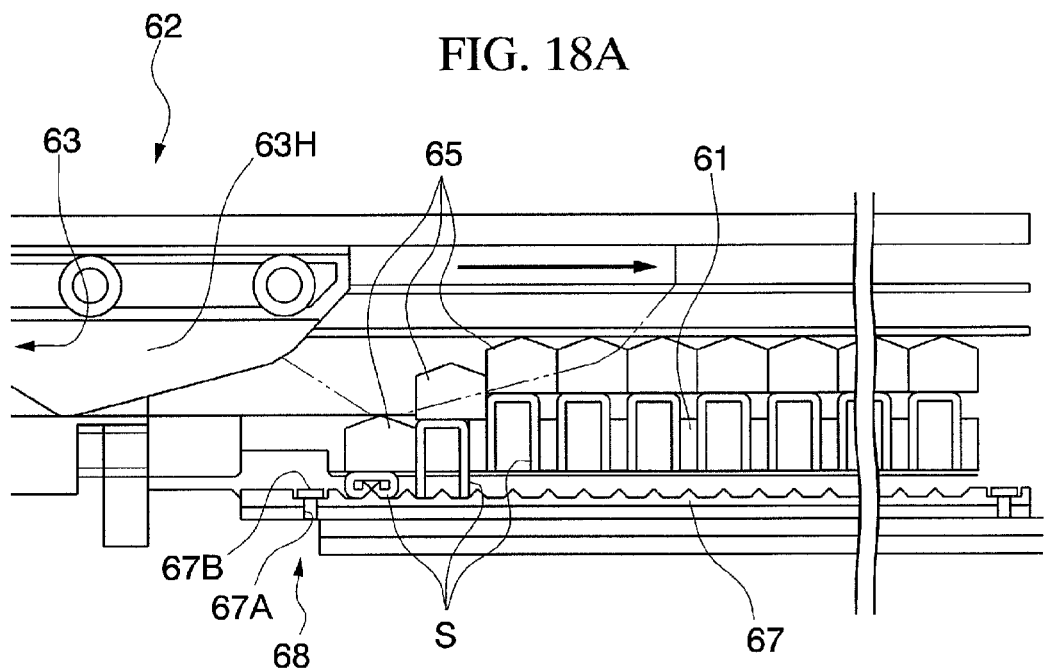
FIG. 18A is a view for explaining the stapling mechanism in the anastomotic apparatus of the present invention, and shows a summary of the operations of the firing mechanism.
Figure 18B:
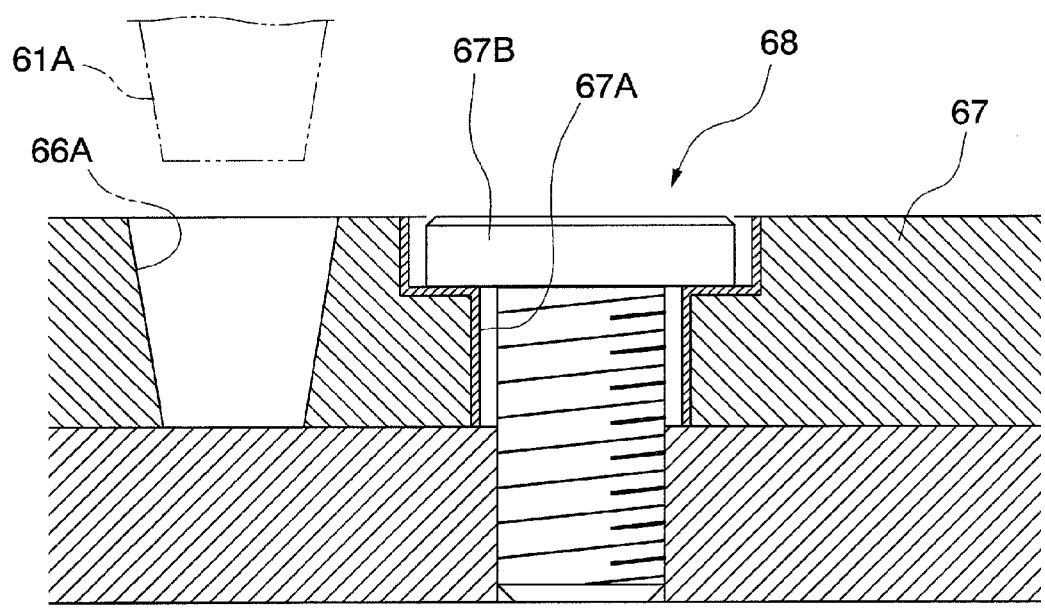
FIG. 18B is a view for explaining the stapling mechanism in the anastomotic apparatus of the present invention, and shows the abbreviated structure of the floating mechanism.

FIG. 16 and FIG. 17 are views for explaining the operation of the firing mechanism 60 and FIGS. 18A and 18B are views for explaining the operation of the stapling mechanism.

As shown in FIGS. 4 and 5, the firing mechanism 60 is provided with an upper firing mechanism 60R which is disposed to the clamp 2R and a lower firing mechanism 60L which is disposed to clamp 2L. Each firing mechanism 60 is provided with an ejector 62 and a staple housing 61 for holding staples S such as shown in FIG. 18A.

Further, with regard to the ejection sliders 63R,63L, as shown in FIG. 16, the ejection slider 63R forming the upper stapling mechanism in anastomotic apparatus 1 is provided to the frame 11R for forming the clamp member 21R of the clamp 2R, and the ejection slider 63L forming the lower stapling mechanism in anastomotic apparatus 1 is provided to the frame 15L for forming the clamp member 25L of the clamp 2L In this embodiment, the firing mechanism 60 is disposed to the clamp members (one clamp member) 21R,25L of the clamp member pairs 21,25. The anvil member 67 is disposed to the clamp members (other clamp member) 21L,25R.

In other words, in clamp 2R, as shown in FIG. 4, the upper firing mechanism 60R for stapling the side which is up when the operator is holding the anastomotic apparatus 1 is disposed to the clamp member 21 R, and the anvil member 67R which corresponds to the lower firing mechanism 60R disposed to clamp 2R is disposed to the clamp member 21R, for example.

As shown in FIG. 5, in clamp 2L, the lower firing mechanism 60L is disposed to the clamp member 25L and the anvil member 67L is disposed to clamp member 21L.

Staple housing 61 has a plurality of holding holes (not shown) corresponding to the shape and array of the staples S. In this embodiment, the holding holes are formed so that the upper and lower two rows of staples S are disposed in a parallel array along the longitudinal direction of the respective clamp members 21R,25L.

As shown in FIGS. 18A and 18B, an ejector 62 is provided with an ejection slider 63, a slider head 63H formed to the distal end of the ejection slider 63, an ejection knob 64 as show in FIGS. 16 and 17 for inputting to the ejection slider 63, and knockouts 65.

Further, the ejection slider 63 is provided with an ejection slider 63R and an ejection slider 63L.

Staples S are highly strong and rust-resistant and are formed of a material such as titanium or the like which does not readily cause biologic reaction. The staples are formed in an U-shape. The needle portions at either end of the staple, which are formed by bending the staple ends with respect to the central axis of the staple, are designed to engage and staple overlapping sections of organ tissue P by bending the needle portions toward the middle of the central axis of the staple.

As shown in FIG. 18A, respective anvil members 67 are provided with two rows of forming recesses for forming the staples by bending the needle portions at either end of the ejected staple S toward the middle of the central axis, with these anvil members disposed corresponding to the respective staple housings 61R,61L.

As shown in FIG. 18A, the stapling mechanism is designed so that when the ejection slider 63 is advanced, the slider head 63H pushes against the tapered portion of the knockout 65 and advances toward the staples S housed in the staple housing 61. As a result, the staples S are then sequentially ejected toward the anvil member 67.

As shown in FIGS. 16 and 17, a slider guide 64S is formed forward to the advancing direction (direction of movement during ejection) of the ejection knob 64R for the ejection slider 63R. This slider guide 64S extends from the ejection knob 64R to the front of the ejection knob 64L, and is designed to engage with a guide formed to the frame (not shown) of clamp member 21L corresponding to frame 11R, and limit horizontal deviation when the ejection knob 64R is advanced or retracted.

The slider guide 64S forms an ejection sequence controlling mechanism, and prevents the advance of the ejection slider 63L ahead of the ejection slider 63R, and prevents the advance of the ejection slider 63L when the ejection slider 63R is at the starting position (position prior to operation).

As a result, it is possible to prevent the occurrence of errors in operation in the case where the operating sequence during anastomosis requires stapling of the upper tissue by ejection slider 63R, followed by stapling of the lower tissue.

As shown in FIG. 17, a slider guide 64T is formed to the rear of the advancing direction of the ejection knob 64L of the ejection slider 63L. This slider guide 64T is designed to prevent horizontal deviation when advancing or retracting the ejection knob 64L by engaging with the space employed for the guide which is formed between a frame and its corresponding frame (not shown) when the clamp member 25L and the clamp member 25R are closed.

Respective lock knobs 64P,64Q are formed to ejection knobs 64R,64L. These ejection knobs 64R,64L are designed to be able to advance when lock knobs 64P,64Q are pressed and the engagement between the engaging part formed in lock knobs 64P,64Q and the cutout (cutout 11P in frame 11R for example) formed in the guide portion of the frame is released.

As a result, it is possible to prevent an operation mistake of advancing respective ejection knobs 64R,64L.

A floating mechanism 68 is provided to the stapling mechanism. As shown in FIG. 18B, this floating mechanism 68 is composed by forming the diameter of the anvil attachment hole 67A for providing the anvil member 67 to the clamp 2 to be slightly larger than the attachment screw 67B, enabling the relative position of the anvil member 67 with respect to the staple housing 61 to be adjusted within a specific range.

Note, in this embodiment, an explanation was made of the case in which a floating mechanism 68 is provided to the anvil member 67 side, and the staple housing 61 is fixed in place. However, the floating mechanism 68 may be provided freely to either the staple housing 61 or the anvil member 67. It is also acceptable to provide the floating mechanism 68 to the staple housing 61 side, or to both the staple housing 61 and the anvil member 67.

In the stapling mechanism, a positioning pin 61A (positioning mechanism) such as shown in FIG. 18B is provided to the staple facing surface of the staple housing 61, and a positioning hole (positioning mechanism) 66A is formed to the staple facing surface of the anvil member 67. The relative positions of the staple housing 61 and the anvil member 67 are maintained by introducing the positioning pin 61A into the positioning hole 66A.

As a result of the aforementioned design, it is possible to stably form a staple S in the gripped organ tissue P even when there is a deviation in the alignment of the stapling mechanism and thereby prevent the occurrence of poor staple formation or poor stapling, for example.

The anastomotic apparatus 1 is provided with a forward ejection locking mechanism, and is designed so that the ejector which is first operated from among the two sets of stapling mechanisms is locked at the ejection completion position and cannot move.

In this embodiment, the forward ejection locking mechanism is provided with a slider locking member 71 provided to the main body of the anastomotic apparatus and a slider locking recess 75 formed to the ejection slider 63R such as are shown in FIGS. 19A-19D and FIGS. 20A-20E.

The slider locking member 71 is provided with three arms, which are formed of a resin such as plastic or the like, and which extend from the main body of the member in which the attachment hole for attaching to the anastomotic apparatus 1 is formed toward the periphery. The three arms serve respectively as a lock 71A, biasing member 71B, and releasing pin 71C. The slider locking member 71 is designed so that its inclination which is centered on the lock 71A and the attachment hole for releasing pin 71C changes as a result of elastic deformation of the biasing member 71B.

The forward ejection locking mechanism is designed so that when the ejection slider 63R has been advanced, the lock 71A of the slider locking member 71 engages in the slider locking recess 75 of the ejection slider 63R at this leading edge position, locking the ejection slider 63R and preventing the advance or retraction of the ejection slider 63R.

The action of the forward ejection locking mechanism will now be explained with reference to the FIGS. 19A-19D.

Figure 19A:
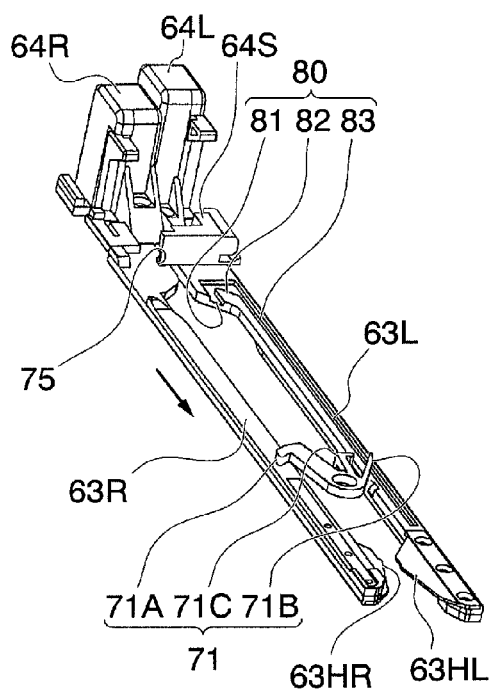
FIG. 19A is a perspective view for explaining the forward ejector locking mechanism in the anastomotic apparatus of the present invention, and shows the state prior to the manipulation of the ejection knob on the right.

As shown in FIG. 19A, the ejection slider 63R is advanced in order to staple the organ tissue P above the anastomotic apparatus 1 which is clamped by the clamp member pair 21.

Figure 19B:
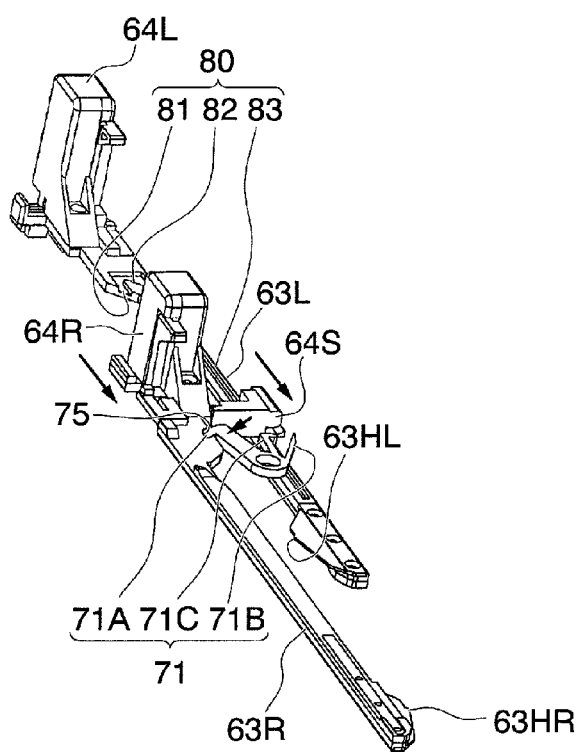
FIG. 19B is a perspective view for explaining the forward ejector locking mechanism in the anastomotic apparatus of the present invention, and shows the state when the ejection knob on the right is manipulated.

When the advanced ejection slider 63R arrives at the leading edge, the lock 71A engages with the slider locking recess 75 as shown in FIG. 19B, preventing further movement of the ejection slider 63R. This state is maintained until the ejection slider 63L is moved to the leading edge and then retracted.

Figure 19C:
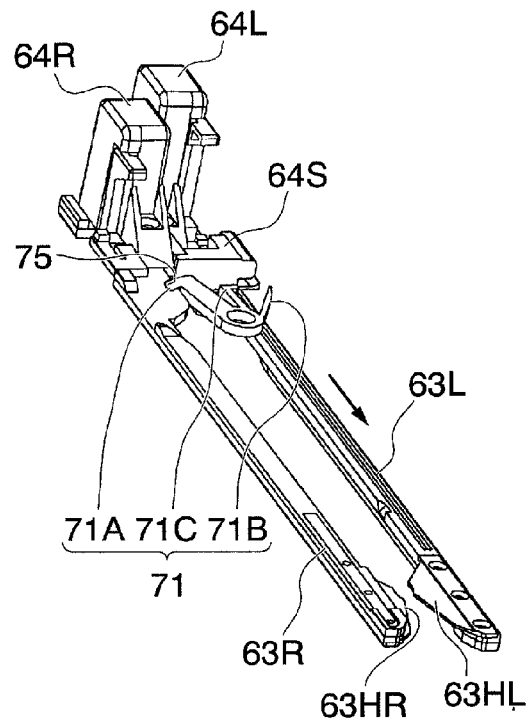
FIG. 19C is a perspective view for explaining the forward ejector locking mechanism in the anastomotic apparatus of the present invention, and shows the state when the ejection knob on the left is manipulated.

Next, as shown in FIG. 19C, the ejection slider 63L is advanced in order to staple the organ tissue P below the anastomotic apparatus 1 which is clamped by the clamp member pair 25.

Figure 19D:
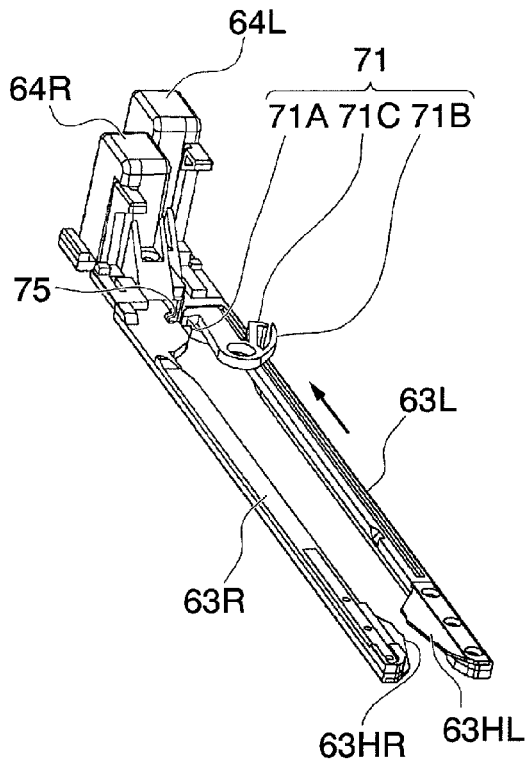
FIG. 19D is a perspective view for explaining the forward ejector locking mechanism in the anastomotic apparatus of the present invention, and shows the state when the ejection knob on the left is returned.

Next, as shown in FIG. 19D, when the ejection slider 63L is retracted, the lock 71A is freed from the slider locking recess 75, thereby enabling sliding of the ejection slider 63R.

Further, the anastomotic apparatus 1 is provided with an ejector lock releasing mechanism. By moving the ejection slider 63 which is operated later to the starting position after completing ejection of the staples S, the lock on the ejection slider 63 which was moved first and engaged by the forward ejection locking mechanism is released and movement is enabled.

In this embodiment, the ejector lock releasing mechanism has a slider locking member 71 and a releasing groove 80 formed to the ejection slider 63L.

The ejector lock releasing mechanism is designed as follows. As shown in FIGS. 19A-19D and FIGS. 20A-20E, the ejection slider 63R (one of the ejectors) is operated first, followed by the ejection slider 63L (the other ejector), after which both ejection sliders 63R,63L are returned to the starting position. By returning to the starting position side, the pointed teeth 32 and the rake teeth 36 are retracted and gripping by the organ gripping mechanism 3 is released.

Note that it is preferable from an operational perspective to employ the ejection slider 63L as the lagging edge when the lock on the ejection slider 63R which was operated first is released using the ejector lock releasing mechanism.

As shown in FIGS. 17, 19A-19D and FIGS. 20A-20E, a releasing groove 80 is formed to the ejection slider 63L. The releasing groove 80 engages with the lock releasing pin 71C and releases the lock 71A from the slider locking recess 75.

As shown in FIGS. 17, 19A-19D and FIGS. 20A-20E, the releasing groove 80 is provided with a pin guide 81, a inclined part 82, and a deformation maintaining part 83 which are formed to the upper surface of the ejection slider 63L.

The operation of the ejector lock releasing mechanism will now be explained with reference to FIGS. 20A-20E. Note that for the purpose of convenience, the slider guide 64S in FIG. 20 is not shown in these figures.

Figure 20A:
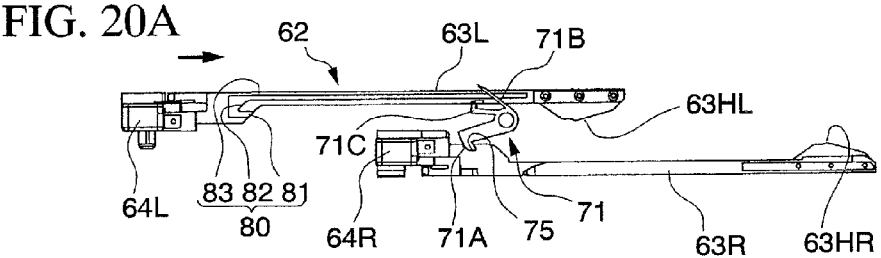
FIG. 20A is a view for explaining the forward ejector locking mechanism of the anastomotic apparatus of the present invention, and shows the state when the ejection knob on the right is manipulated.

First, as shown in FIG. 20A, the ejection slider 63L is advanced in order to staple the organ tissue P which is clamped below the anastomotic apparatus 1.

Figure 20B:
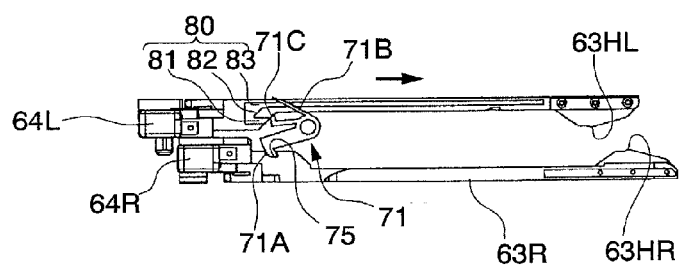
FIG. 20B is a view for explaining the ejector lock releasing mechanism of the anastomotic apparatus of the present invention, and shows the state during manipulation of the ejection knob on the left.

Next, as shown in FIG. 20B, when the ejection of the staples S by the ejection slider 63L is finished, the lock releasing pin 71C approaches the pin guide 81 of the releasing groove 80.

Figure 20C:
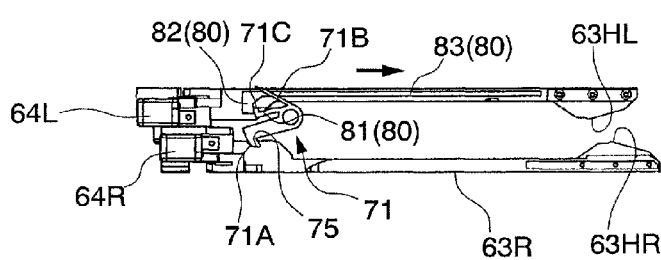
FIG. 20C is a view for explaining the ejector lock releasing mechanism of the anastomotic apparatus of the present invention, and shows the state during manipulation of the ejection knob on the left.

Next, as shown in FIG. 20C, when the ejection slider 63L approaches the leading edge, the lock releasing pin 71C approaches the edge of the back side of the wall which is formed between the inclined part 82 and the pin guide 81 of the releasing groove 80.

Figure 20D:
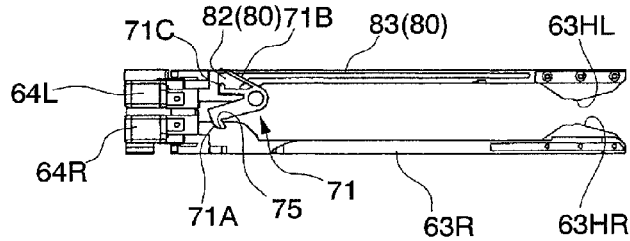
FIG. 20D is a view for explaining the ejector lock releasing mechanism of the anastomotic apparatus of the present invention, and shows the state when manipulation of the ejection knob on the left is completed.

Next, as shown in FIG. 20D, when the ejection slider 63L reaches the leading edge, movement of the lock releasing pin 71C from the pin guide 81 to the inclined part 82 is enabled.

Figure 20E:
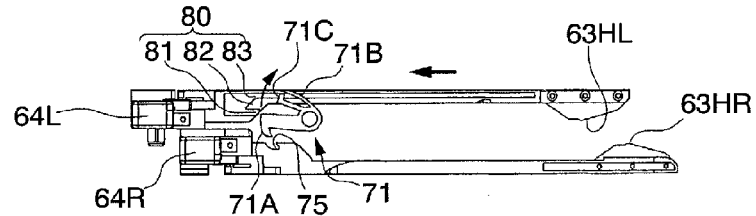
FIG. 20E is a view for explaining the ejector lock releasing mechanism of the anastomotic apparatus of the present invention, and shows the state when the manipulation of the ejection knob on the left is completed and the knob is returned.

Next, as shown in FIG. 20E, when the ejection slider 63L is retracted, the lock releasing pin 71C moves along the inclined part 82 to the outside of the ejection slider 63L side (i.e., up in FIG. 20E)

As a result, the biasing member 71B of the slider locking member 71 deforms, and the lock 71A deforms on the side away from the slider locking recess 75, releasing the lock on the ejection slider 63L.

In addition, the anastomotic apparatus 1 has a grip releasing mechanism (lock releasing mechanism).

FIGS. 21A through 24E are views for explaining the grip releasing mechanism.

The grip releasing mechanism is provided with a releasing member 90, a releasing member controller 95 which is formed to the ejection slider 63R, and an engaging recess 13C which can engage with the engaging pin 93 which is formed to the UB connector 13.

Figure 21A:
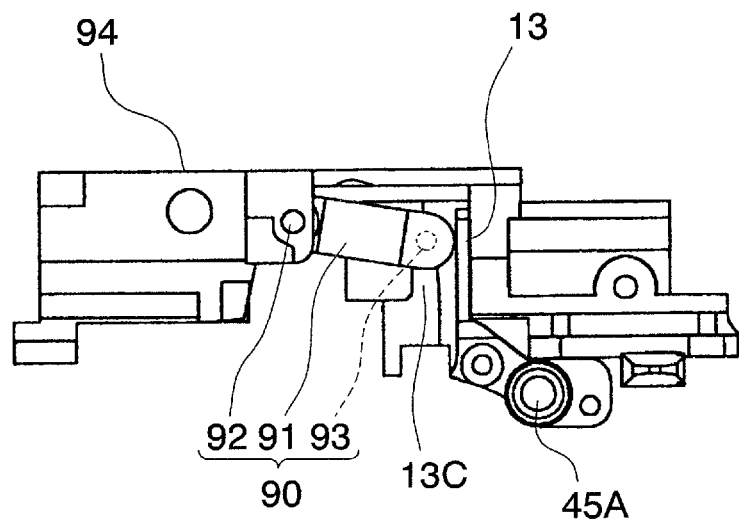
FIG. 21A is a planar view for explaining the structure of the UB connector in the anastomotic apparatus of the first embodiment.
Figure 21B:
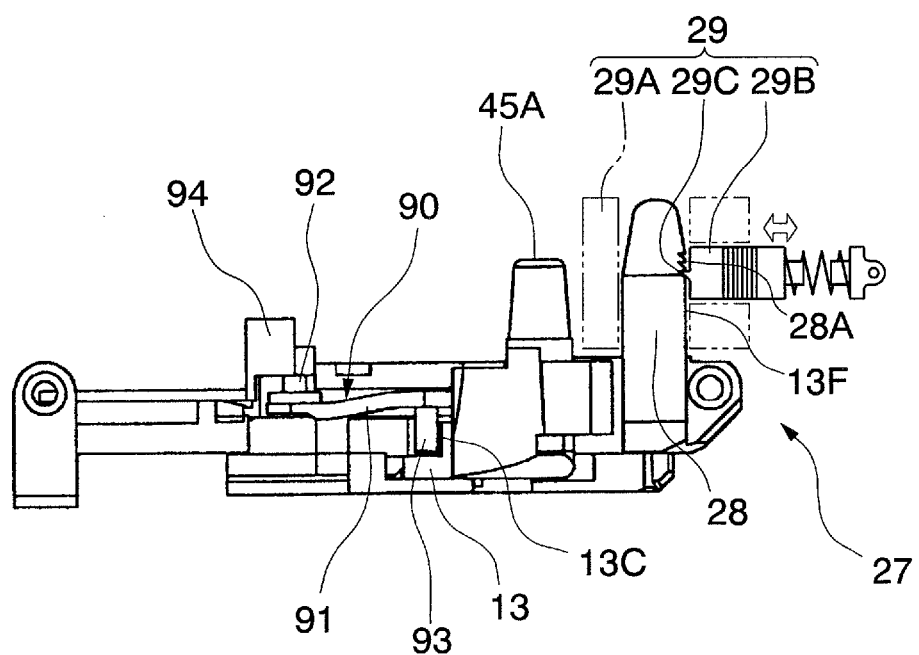
FIG. 21B is a lateral view for explaining the structure of the UB connector in the anastomotic apparatus of the first embodiment.

UB connector 13 is provided with the engaging recess 13C composing a grip releasing mechanism such as shown in FIG. 21A and FIG. 21B, and is capable of engaging with the engaging pin 93.

As shown in FIG. 21B, the UB connector 13 composes a vertical lock 27 for locking the upper clamp members 21R, 21L and the lower clamp members 25R,25L in the closed state.

The vertical lock 27 is provided with an engaging projection 28 and a release knob 29.

The engaging projection 28 is disposed to the lower clamp members 25R,25L, and the release knob 29 is disposed to the upper clamp members 21R,21L The engaging projection 28 consists of a plate member which extends toward the upper clamp members 21R,21L side, and is provided with a plurality of engaging grooves 28A formed parallel to the axes O1R, O1L of the clamps 2R,2L.

The release knob 29 is for operating the vertical lock by engaging with the engaging projection 28, and for releasing the locked vertical lock 27. The release knob 29 is provided with a wall 29A in which a hole for inserting the engaging projection 28 is formed, and an engaging member 29B for locking the engaging projection 28.

The engaging member 29B is biased toward the engaging groove 28A, and an engaging projection 29C, formed at the distal end of the engaging member 28B, engages in the engaging groove 28A, thereby locking the clamps 2R,2L in the closed state.

Further, by moving the release knob 28 opposite the biasing direction, the engagement of the engaging projection 29C in the engaging groove 28A is released and the vertical lock 27 is released.

A rotating pin 92 and an engaging pin 93 are formed to the releasing member 90. The rotating pin 92 is provided to the surface of one side at one end of the releasing member main body 91, which is formed in a circular shape, and can rotate with respect to anastomotic apparatus 1. The engaging pin 93 is formed to the surface of the other side, i.e., the surface opposite that to which the rotating pin 92 is formed, at the other end of the releasing member main body 91. The releasing member 90 is connected to the anastomotic apparatus 1 via the rotating pin 92.

Figure 22A:
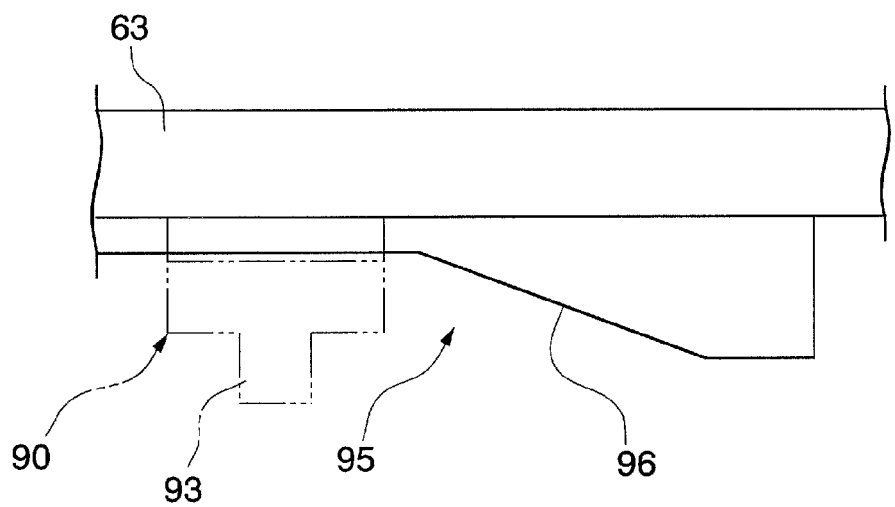
FIG. 22A is a lateral view for explaining the releasing member controller which composes the grip releasing mechanism in the anastomotic apparatus of the present invention.
Figure 22B:
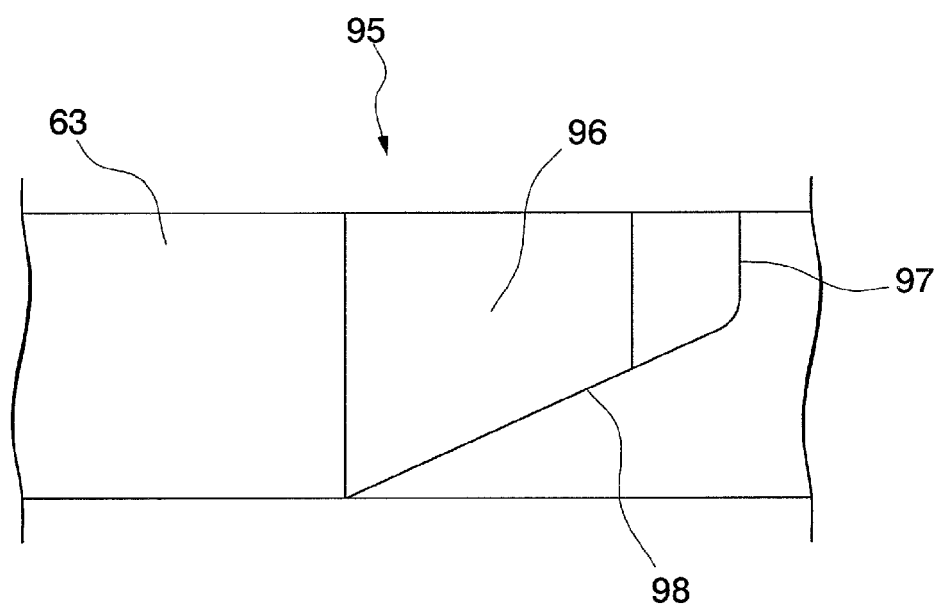
FIG. 22B is a planar view for explaining the releasing member controller which composes the grip releasing mechanism in the anastomotic apparatus of the present invention.

FIGS. 22A and 22B are views for explaining the releasing member controller 95.

FIG. 22A is a lateral view and FIG. 22B is a planar view showing the bottom surface of the ejection slider 63R. The releasing member controller 95 is provided with a releasing member deforming inclined part 96 which is formed to the bottom surface of the ejection slider 63R, the rear side of the releasing member deforming inclined part 96 becoming gradually higher with increasing distance from the bottom surface of the ejection slider 63R; a releasing member restoring step 97 which is formed to the back side of the releasing member deforming inclined part 96; and a inclined part 98 on which the engaging pin 93 of the releasing member 90, which is disposed roughly perpendicular to the ejection slider 63R, rotates toward the direction of movement (the direction of retraction) of the ejection slider 63R due to retraction of the ejection slider 63R.

FIGS. 23A-23D and FIGS. 24A-24E are views for explaining the action of the grip releasing mechanism. FIGS. 23A-23D are for explaining the action of the releasing member 90. FIGS. 24A-24E are for explaining the release of the organ gripping mechanism 3 by the releasing member 90.

Figure 23A:
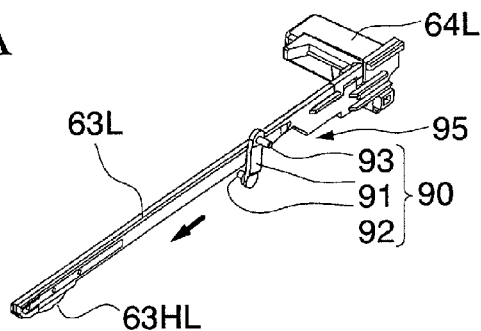
FIG. 23A is a view for explaining the action of the releasing member in the grip releasing mechanism in the anastomotic apparatus of the present invention, and shows the state during advance of the ejection knob on the left.

First, the ejection slider 63L is advanced as shown in FIG. 23A.

Figure 23B:
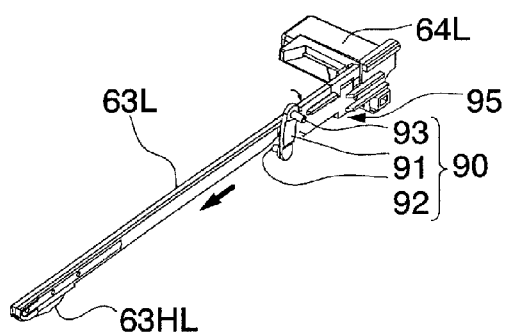
FIG. 23B is a view for explaining the action of the releasing member in the grip releasing mechanism in the anastomotic apparatus of the present invention, and shows the state after the advance of the ejection knob on the left is completed.

Next, the releasing member controller 95 of the ejection slider 63L is advanced to the releasing member 90, as shown in FIG. 23B, causing the releasing member main body 91 to ride up onto the releasing member deforming inclined part 96 of the releasing member controller 95. Because the releasing member main body 91 undergoes deformation, the releasing member 90 does not rotate in this case.

Figure 23C:
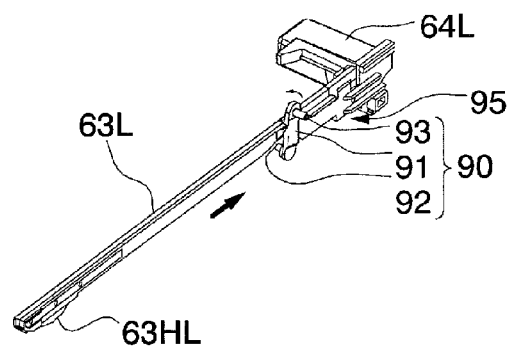
FIG. 23C is a view for explaining the action of the releasing member in the grip releasing mechanism in the anastomotic apparatus of the present invention, and shows the state during the return of the ejection knob on the left.

Next, as shown in FIG. 23C, when the deformed releasing member 90 reaches the releasing member restoring step 97 of the releasing member controller 95, the releasing member main body 91 drops from the releasing member deforming inclined part 96 onto the releasing member restoring step 97, resolving the deformation of the releasing member main body 91. As a result, the releasing member 90 does not rotate when the ejection slider 63L advances.

Figure 23D:
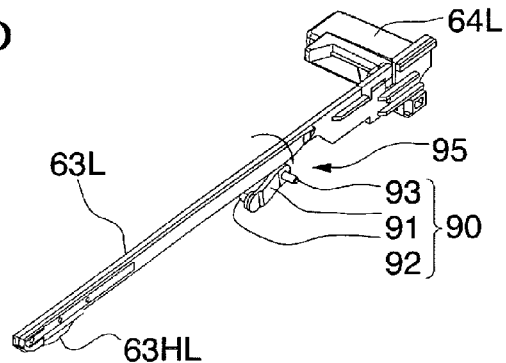
FIG. 23D is a view for explaining the action of the releasing member in the grip releasing mechanism in the anastomotic apparatus of the present invention, and shows the state when the ejection knob on the left is returned.

Next, when the ejection slider 63L is retracted as shown in FIG. 23D, the releasing member 90 is rotated by the inclined part 98. As a result, the engaging pin 93 of the releasing member 90 is inserted into the engaging recess 13A of the UB connector 13.

FIGS. 24A-24E are views for explaining the action of the releasing member 90 in the grip releasing mechanism.

Figure 24A:
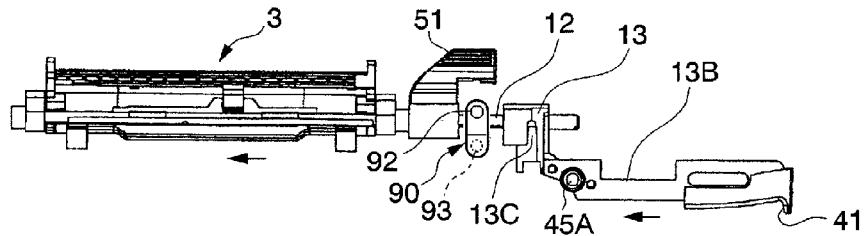
FIG. 24A is a view for explaining the action of the grip releasing mechanism in the anastomotic apparatus of the present invention, and shows the state during gripping by the organ gripping mechanism.

First, the operating knob 41 is advanced to operate the organ gripping mechanism 3 as shown in FIG. 24A.

Figure 24B:
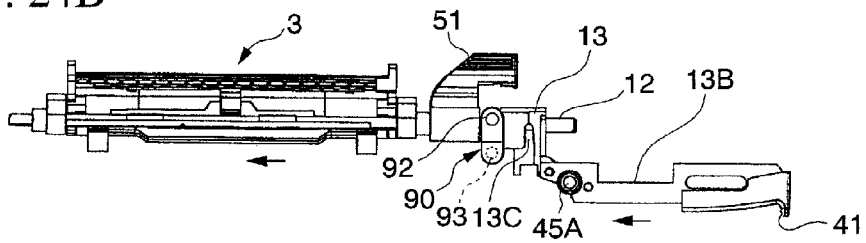
FIG. 24B is a view for explaining the action of the grip releasing mechanism in the anastomotic apparatus of the present invention, and shows the state during gripping by the organ gripping mechanism.
Figure 24C:
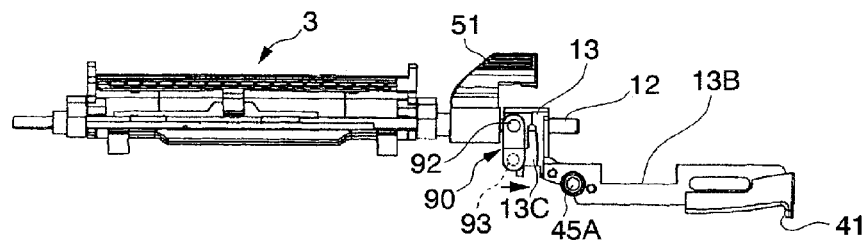
FIG. 24C is a view for explaining the action of the grip releasing mechanism in the anastomotic apparatus of the present invention, and shows the state after gripping by the organ gripping mechanism.

FIG. 24B shows the position when the pointed teeth 32 and the rake teeth 36 are both moved and exposed in the organ gripping mechanism 3. FIG. 24C shows the case where the rake teeth 36 reach the leading edge and UB connector 13 has advanced to the position at which the organ tissue P is gripped (the arrow in the return direction is omitted).

The releasing member 90 does not rotate during the states shown in FIG. 24A and FIG. 24B, until the UB connector 13 reaches the position shown in FIG. 24C, nor during the states shown in FIG. 23A and FIG. 23B, until the releasing member main body 91 reaches the state shown in FIG. 23C and deforms, allowing the releasing member 90 to ride up over the releasing member controller 95.

Next, as shown in FIG. 24C, the releasing member 90 begins to rotate due to the releasing member controller 95 in FIGS. 23B, 23C.

Figure 24D:
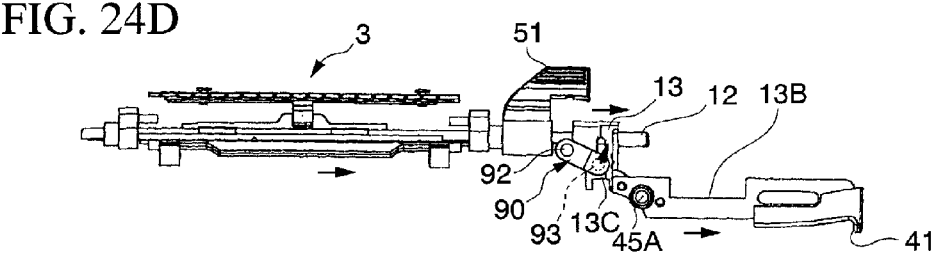
FIG. 24D is a view for explaining the action of the grip releasing mechanism in the anastomotic apparatus of the present invention, and shows the state during the return of the organ gripping mechanism.

Next, as shown in FIG. 24D, releasing member 90 rotates, and the engaging pin 93 of the releasing member 90 begins to engage with the engaging recess 13C of the UB connector 13, and the connecting rod 12 of the organ gripping mechanism 3 is retracted via the UB connector 13. As a result, the pointed teeth 32 and the rake teeth 36 sink down into the housing 39.

Figure 24E:
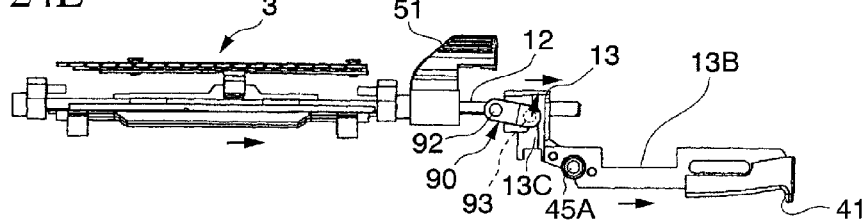
FIG. 24E is a view for explaining the action of the grip releasing mechanism in the anastomotic apparatus of the present invention, and shows the state after the organ gripping mechanism is returned.

Next, as shown in FIG. 24E, the releasing member 90 is rotated until reaching the rotation edge. The UB connector 13 is retracted back to this position and the grip on the organ tissue P is released by the organ gripping mechanism 3.

As discussed above, by engaging the releasing member 90 with the engaging recess 13C of the UB connector 13 and retracting the UB connector 13, the pointed teeth 32 and the rake teeth 36 come free from the organ tissue P without returning the everting mechanism 5 to its original pre-eversion position. As a result, the organ tissue P can be freed from the anastomotic apparatus 1 while maintaining the state of apposition in the anastomosed organ tissue P.

The specific operation will now be explained with reference to FIGS. 25A-25D.

Figure 25A:
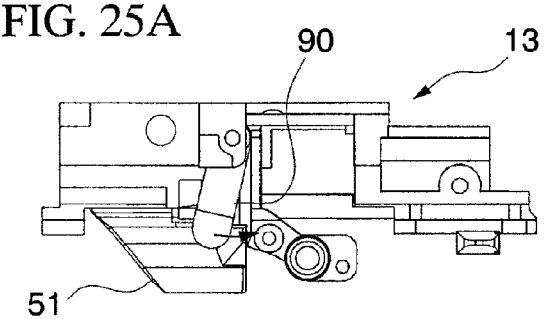
FIG. 25A is a view for explaining the action when the engagement of the everting knob in the anastomotic apparatus according to the first embodiment is released by the grip releasing mechanism, and is a planar view showing the pre-release state.

First, when the ejection slider 63L is advanced and the stapling is concluded, the engaging projection 51A is inserted into the engaging recess 13A of the UB connector 13 as shown in FIG. 25A. This state is equivalent to that shown in FIGS. 15C(1) and 15C(2).

Figure 25B:
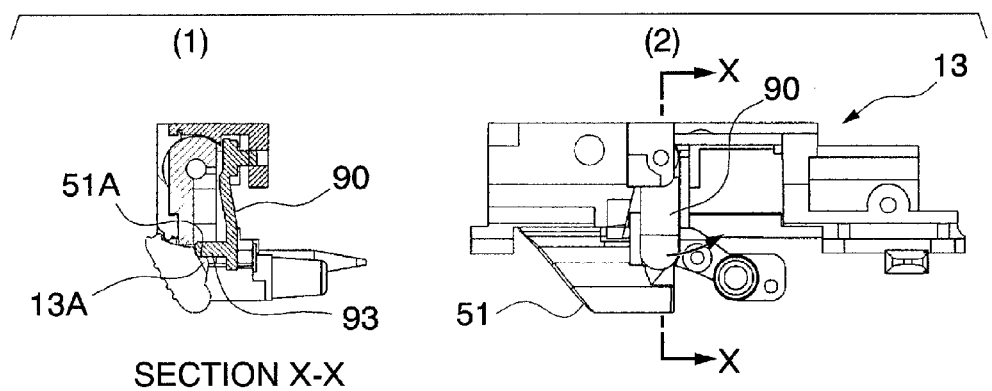
FIG. 25B is a view for explaining the action when the engagement of the everting knob in the anastomotic apparatus of the first embodiment is released by the grip releasing mechanism, wherein FIG. 25B (1) is a planar view showing the state during the release and FIG. 25B (2) is a view shown in cross-section along the line X-X shown in FIG. 25B (1).
Figure 25C:
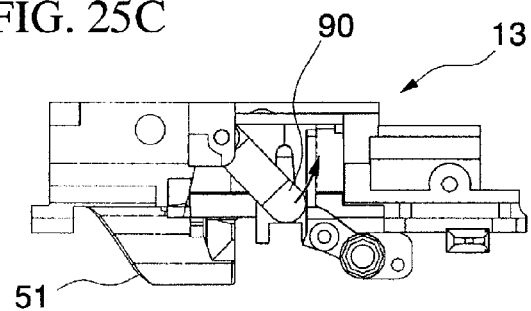
FIG. 25C is a view for explaining the action when the engagement of the everting knob of the anastomotic apparatus in the first embodiment is released by the grip releasing mechanism, and is a planar view showing the state during release.

Next, when the ejection slider 63L is retracted and the releasing member 90 rotates (see FIGS. 23C and 23D), the engaging pin 93 comes in contact with the engaging projection 51A as shown in FIGS. 25B(1),(2) and is pressed in the direction which pulls the engaging projection 51A from the engaging recess 13A. Once the releasing member 90 rotates to a specific angle, the engaging projection 51A is pulled out from the engaging recess 13A as shown in FIG. 25C.

Figure 25D:
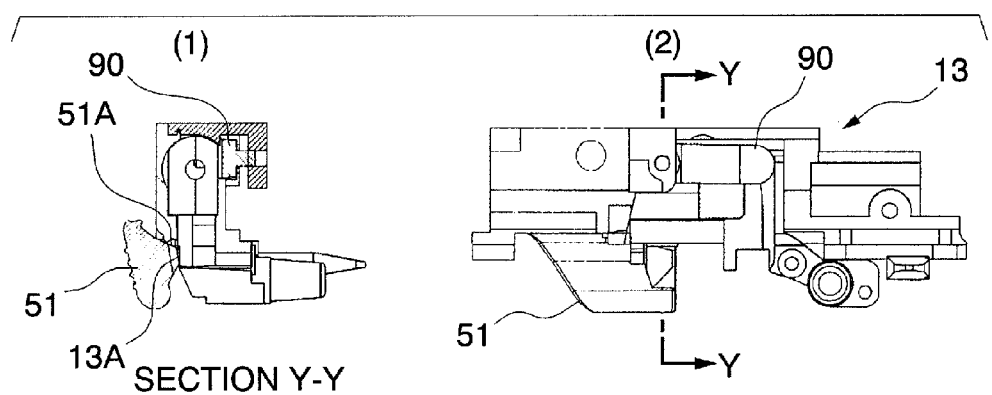
FIG. 25D is a view for explaining the action when the engagement of the everting knob in the anastomotic apparatus of the first embodiment is released by the grip releasing mechanism, wherein FIG. 25D (1) is a planar view showing the state after release and FIG. 25D (2) is a view shown in cross-section along the line Y-Y shown in FIG. 25D (1).

As result, the eversion operating knob 51 does not return to the original position when the UB connector 13 is retracted, and the UB connector 13 can be retracted by pulling out the engaging projection 51A from the engaging recess 13A as shown in FIGS. 25D(1),(2).

Here, FIG. 25B(1) is a view in cross-section along the line X-X of FIG. 25B(2) and FIG. 25D(1) is a view in cross-section along the line Y-Y of FIG. 25D(2).

The action of the anastomotic apparatus 1 will now be explained with reference to FIG. 26A through FIG. 34.

Figure 26A:
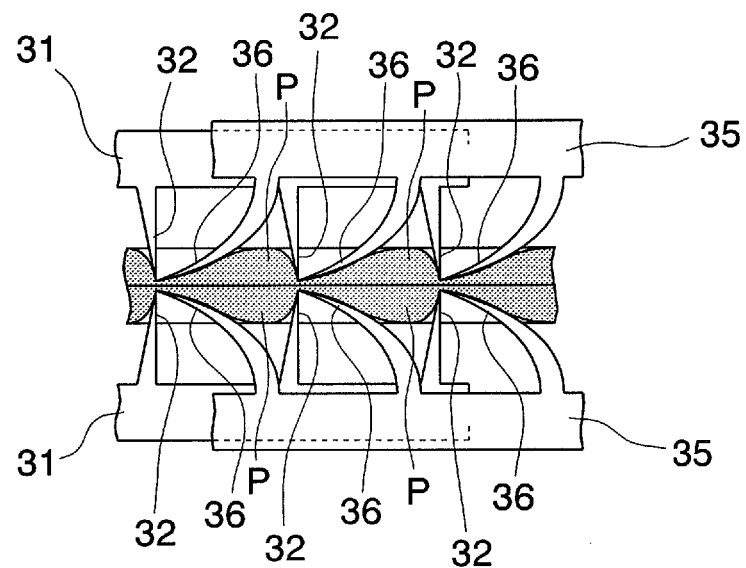
FIG. 26A is a view for explaining an example and the action of the pointed teeth and the rake teeth of the organ gripping mechanism in the anastomotic apparatus of the first embodiment, and shows the state prior to gripping of the organ tissue.
Figure 26B:
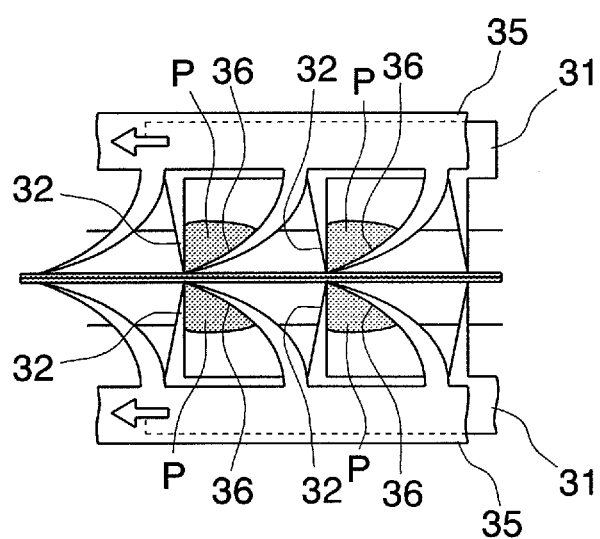
FIG. 26B is a view for explaining an example and the action of the pointed teeth and the rake teeth of the organ gripping mechanism in the anastomotic apparatus of the first embodiment, and shows the state after gripping of the organ tissue.

First, a marker (not shown in the figures) is disposed in between the paired opposing clamping surfaces in clamp 2 to facilitate visualization when the edges of the tubular organ tissue P are flattened. Clamp 2 is made to grip by rotating around the axis O1 and operating knob 41 is manipulated. As a result, organ tissue P is pierced by pointed teeth 32 as shown in FIG. 26A and FIG. 26B, and the organ tissue P is pulled and gripped by the rake teeth 36.

The example here shows the case for gripping the edges of a tubular tissue from which a diseased portion has been excised. However, it is typically the procedural sequence to clamp the tubular organ tissue prior to excision of the diseased area and formation of an edge, and then remove the disease area.

Figure 27:
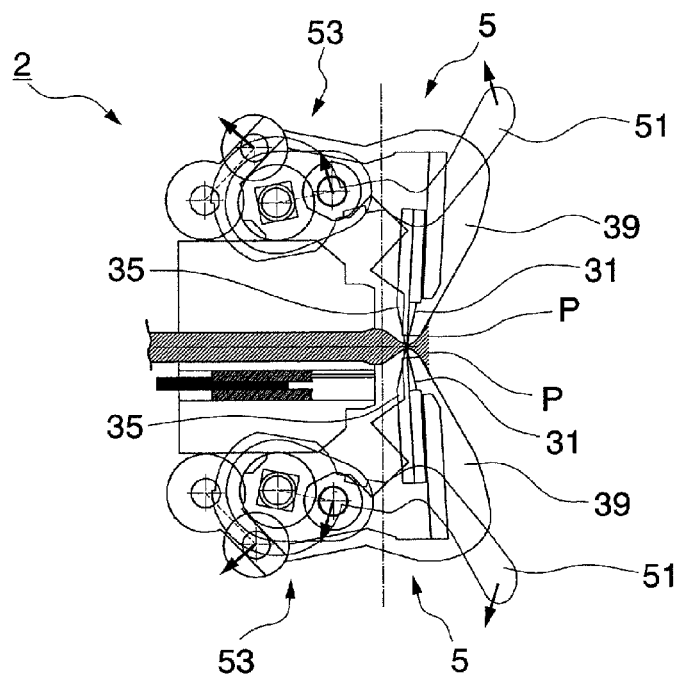
FIG. 27 is a view for explaining the action of the anastomotic apparatus according to the first embodiment, and shows the state when the organ tissue is gripped by the organ gripping mechanism.
Figure 28:
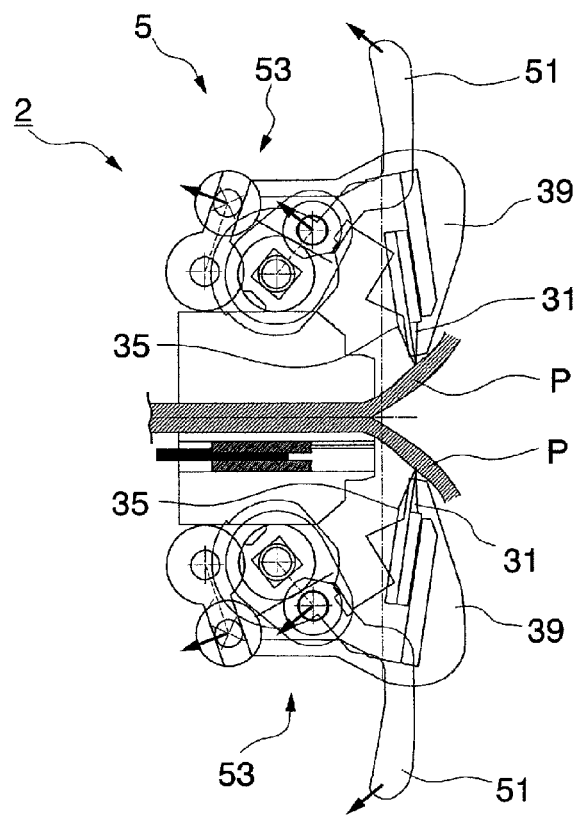
FIG. 28 is a view for explaining the action of the anastomotic apparatus according to the first embodiment, and shows the process of everting the organ tissue gripped by the organ gripping mechanism.
Figure 29:
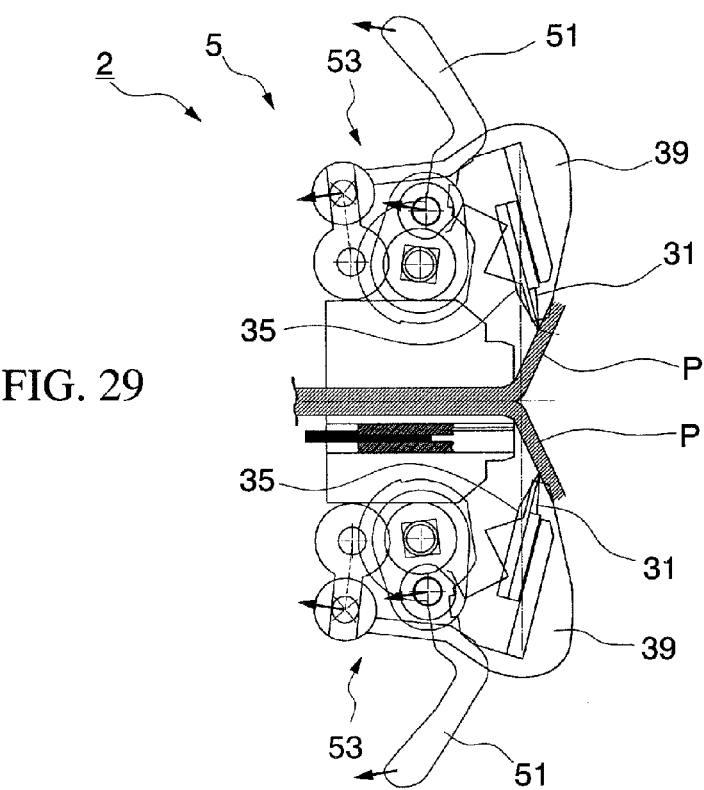
FIG. 29 is a view for explaining the action of the anastomotic apparatus according to the first embodiment, and shows the process of everting the organ tissue gripped by the organ gripping mechanism.
Figure 30:
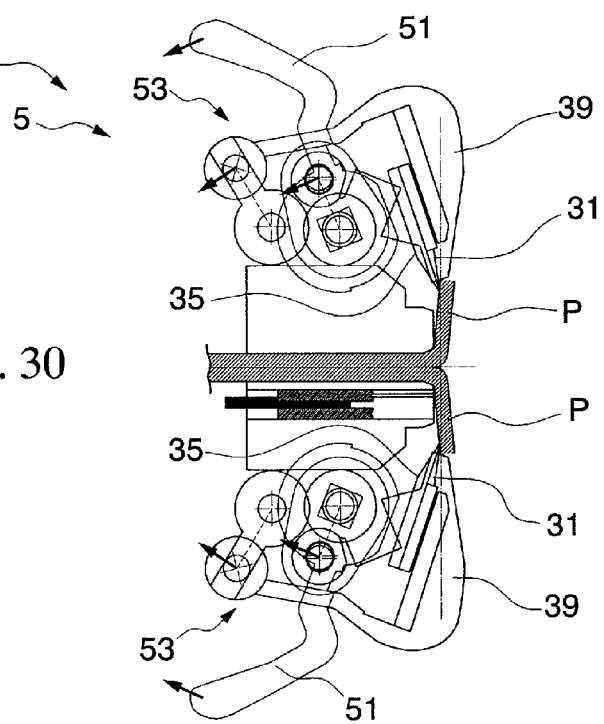
FIG. 30 is a view for explaining the action of the anastomotic apparatus according to the first embodiment, and shows the process of everting the organ tissue gripped by the organ gripping mechanism.

Next, as shown in FIG. 27 and FIG. 28, the eversion operating knob 51 is manipulated to change the arrangement of the link 53 of the everting mechanism 5, everting the edges of the organ tissue P. FIGS. 29 and 30 show this process ongoing.

Figure 31:
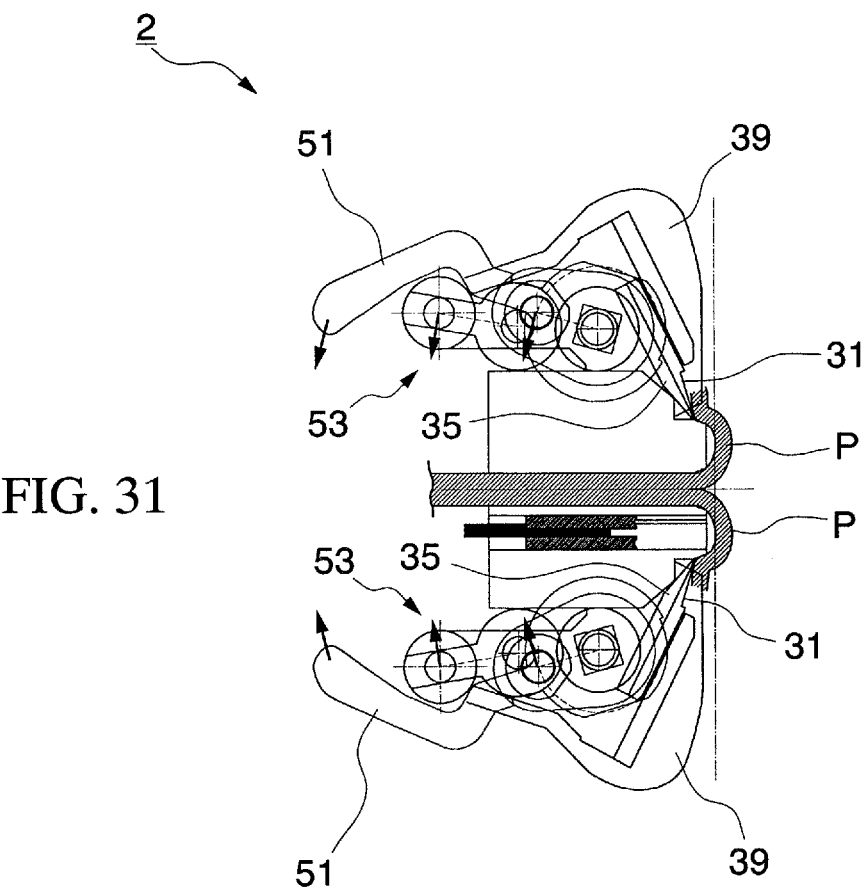
FIG. 31 is a view for explaining the action of the anastomotic apparatus according to the first embodiment, and shows the state after eversion of the organ tissue is completed.

Next, as shown in FIG. 31, the eversion operating knob 51 is rotated further, moving the edges of the organ tissue P to the position at which the eversion is completed.

Figure 32:
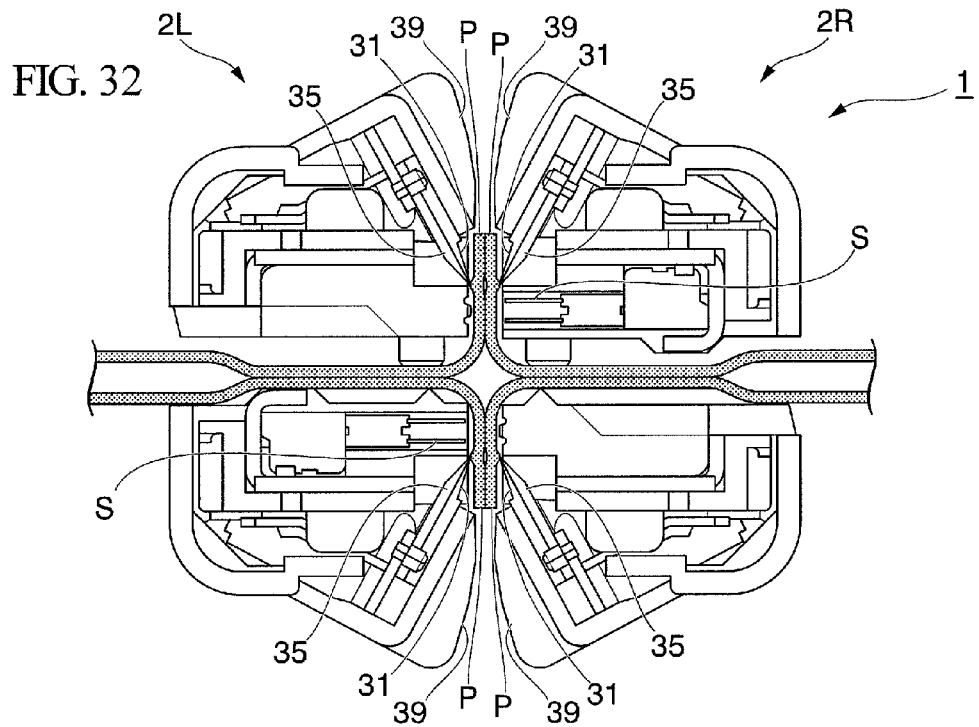
FIG. 32 is a view for explaining the action of the anastomotic apparatus according to the first embodiment, and shows the state when the edges of the everted tubular organ tissue are apposed.

Next, the two sets of clamps 2R,2L are rotated about the axis O2, so that clamp 2R and clamp 2L are positioned opposite one another as shown in FIG. 32, and the edges of the opening in the organ tissue P everted by clamps 2R,2L are brought into apposition.

The clamp 2R and the clamp 2L are sufficiently overlapped at this time due to the fork connector hook N which is provided at their distal ends.

Figure 33:
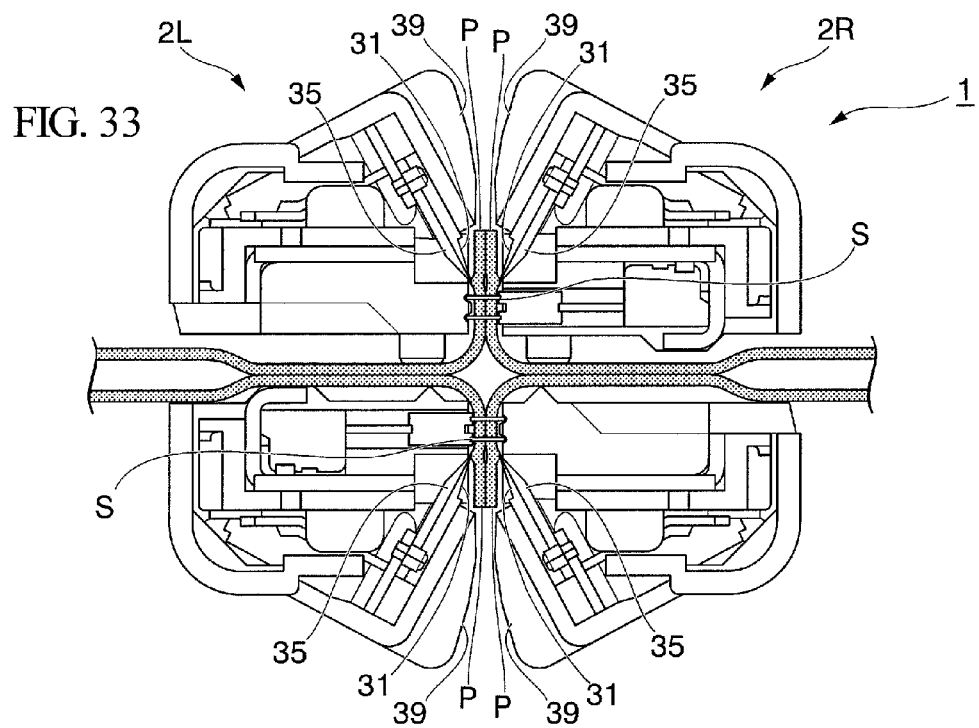
FIG. 33 is a view for explaining the action of the anastomotic apparatus according to the first embodiment, and shows the state when the apposed edges of the organ tissue are stapled.

Next, the right and left firing mechanisms 60 are operated to staple the respective organ tissue P sections apposed as shown in FIG. 33 using staples S.

Stapling is carried out by operating the respective ejection knobs 64R,64L causing sequential sliding of the respective ejection sliders 63R,63L. The respective slider heads 63H then advance, causing the corresponding knockouts 65 to advance. As a result, the staples S are ejected from the staple housing 61 toward the anvil member 67 and are formed by bending of the needle portions.

Figure 34:
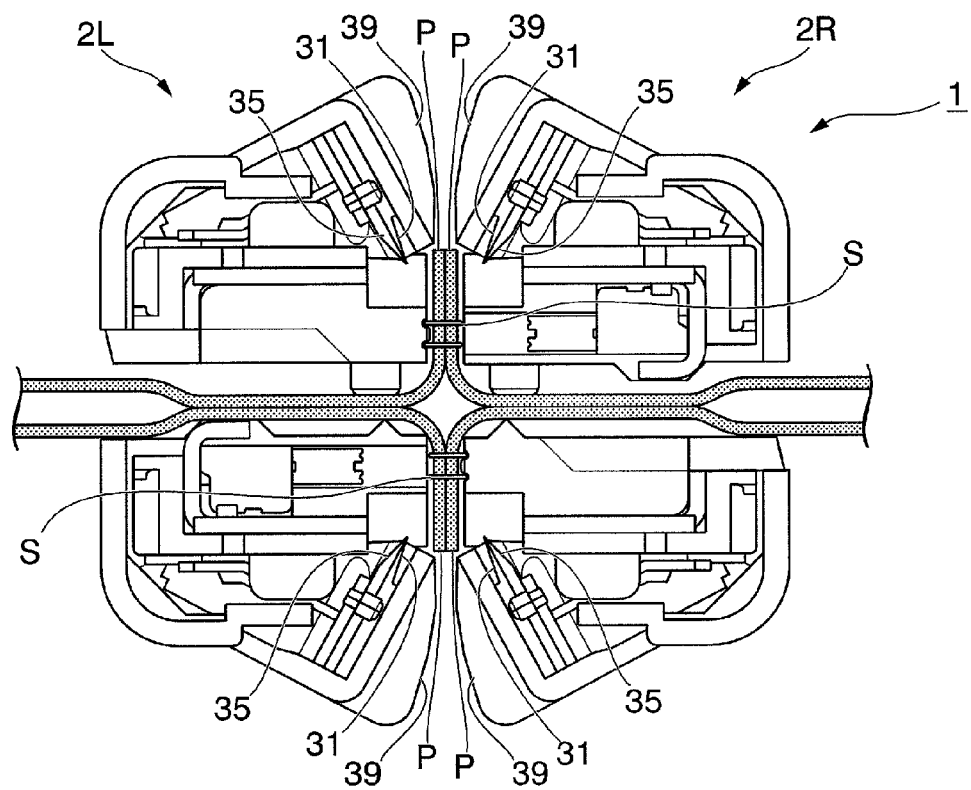
FIG. 34 is a view for explaining the action of the anastomotic apparatus according to the first embodiment, and shows the state when the stapled organ tissue is released from the grip of the organ gripping mechanism.

Next, as shown in FIG. 34, the pointed teeth 32 and the rake teeth 36 of the organ gripping mechanism 3 are retracted by sequentially retracting the ejection slider 63L and the ejection slider 63R, moving the pointed teeth 32 and the rake teeth 36 away from the organ tissue P.

In this state, the clamps 2R and 2L are opened, after which they are rotated about the axis O2, thereby separating the respective clamp members 21R,21L,25R,25L of the anastomotic apparatus from the organ tissue P.

Figure 35A:
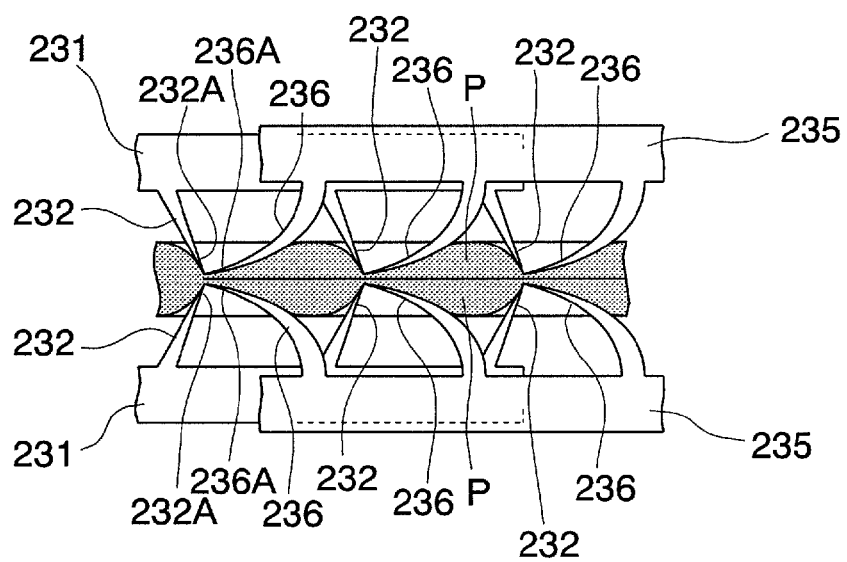
FIG. 35A is a view for explaining a first modification and the action of the pointed teeth and the rake teeth of the organ gripping mechanism in the anastomotic apparatus of the first embodiment, and shows the state prior to gripping of the organ tissue.
Figure 35B:
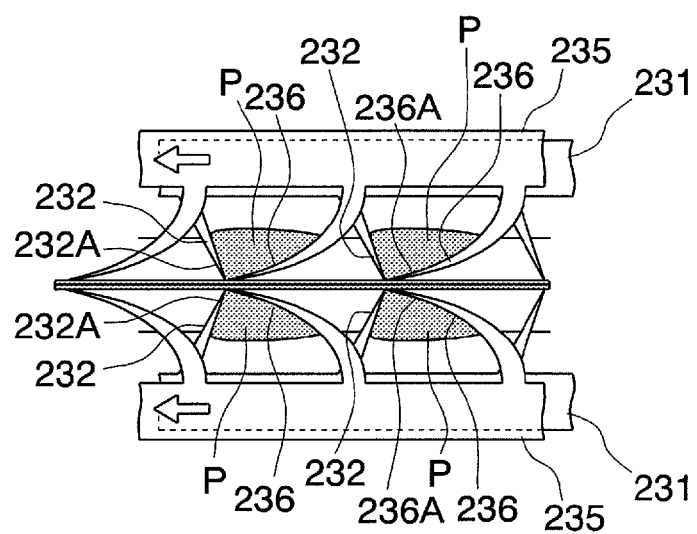
FIG. 35B is a view for explaining the action and a first modification of the arrangement of the pointed teeth and the rake teeth of the organ gripping mechanism in the anastomotic apparatus of the first embodiment, and shows the state when the organ tissue is gripped.

Note that the above-described first embodiment described the case where the pointed teeth 32 extend roughly in the piercing direction. However, in place of pointed teeth 32, it is also acceptable to provide pointed teeth 232 which are formed extending with a slight incline toward the rake teeth 236 side, as shown in FIG. 35A and FIG. 35B. By employing this structure, piercing can be carried out easily and sufficient gripping together with the rake teeth 236 of the organ tissue P is enabled.

Figure 36A:
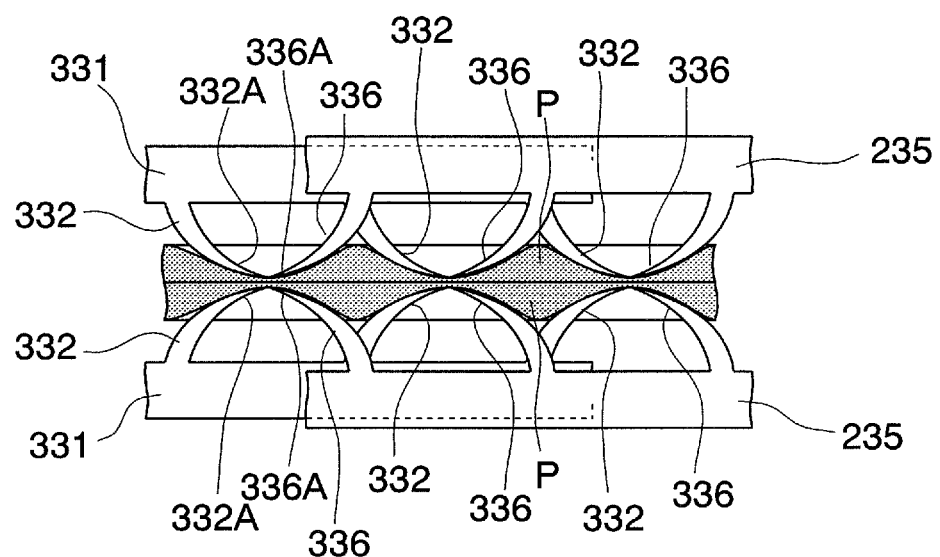
FIG. 36A is a view for explaining the action and a second modification of the arrangement of the pointed teeth and the rake teeth of the organ gripping mechanism of the anastomotic apparatus according to the first embodiment, and shows the state before gripping of the organ tissue.
Figure 36B:
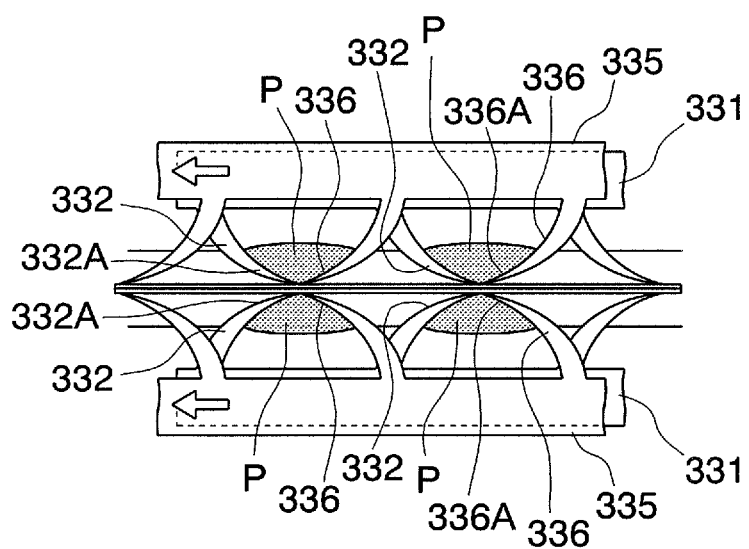
FIG. 36B is a view for explaining the action and a second modification of the arrangement of the pointed teeth and the rake teeth of the organ gripping mechanism of the anastomotic apparatus of the first embodiment, and shows the state after gripping of the organ tissue.

Further, as shown in FIGS. 36A and 36B for example, pointed teeth 332 may be formed with a curve such as for rake teeth 336, with the tips 332A gradually displaced toward the rake teeth 336 side. By employing this structure, damages to the organ tissue P can be prevented and gripping to hold the organ tissue is ensured. Note that profiles other than that of rake teeth 336 may be employed in a design in which the tips are gradually displaced toward the rake teeth side.

In the clamp members 21R, 21L, 25R, 25L, the eversion operating knob 51 is employed to perform horizontal remote operation to hold the organ gripping mechanism 3 at the pre-eversion position or the post-eversion position. As a result, it is possible to easily carry out the everting operation, and to carry out a stable everting operation by holding the organ gripping mechanism 3 with certainty at the pre- and post-eversion positions.

In the clamps 102R,102L, the organ tissue P held by clamp 2 can be maintained at roughly the same thickness, so that the organ tissue P can be stapled while being held stably.

Further, by providing a grip controlling mechanism, the organ gripping mechanism 3 is held at the pre-eversion position or post-eversion position respectively. When the organ gripping mechanism 3 is moved to the post-eversion position side, the everted organ tissue P is prevented from coming free from the pointed teeth 32 and the rake teeth 36, thereby enabling the gripped organ tissue P to be held stably.

Further, in the clamp members 21R,21L,25R,25L, the pointed teeth 32 and the rake teeth 36 are housed in the housing 39. As a result, the tips 32A,36A of the pointed teeth 32 and the rake teeth 36 are prevented from coming into contact with and injuring or damaging an external object.

As a result, a healthcare professional or the like is able to handle the equipment easily, safely and effectively.

Further, it is possible to prevent damage to the organ tissue P by damaged pointed teeth 32 or rake teeth 36.

In clamps 2R and 2L, the gripped organ tissue P can be easily and effectively gripped and everted by the organ gripping mechanism 3 and the everting mechanism 5 of the respective clamp members.

Further, in the clamps 2R and 2L, the corresponding upper and lower organ gripping mechanisms 3 are operated in synchrony, so that the organ tissue P can be simultaneously gripped from above and below, enabling stable gripping of the organ tissue P.

The anastomotic apparatus 1 is provided with a separation controlling mechanism. As a result, the clamps 2R,2L can only be opened when the two ejectors are both positioned at the starting point, thereby preventing damage to the organ tissue P.

In this anastomotic apparatus 1, the organ tissue P is gripped securely by the organ gripping mechanism 3 and held between the clamping surfaces during operation of the two ejection knobs 64R,64L and completion of the anastomosis, thus enabling a stable anastomosis to be performed.

By operating release knob 29 in this anastomotic apparatus 1, the gripping by vertical lock 27 and the organ gripping mechanism 3 can be easily released and injury to the organ tissue P caused by multiple sequential or mistaken operations during anastomosis can be prevented. Thus a continuous operational sequence can be carried out easily and safely.

As described above, the anastomotic apparatus 1 enables the anastomosis of organ tissue P efficiently and safely.

Next, the second embodiment of the present invention will be explained with reference to the figures.

Figure 37:
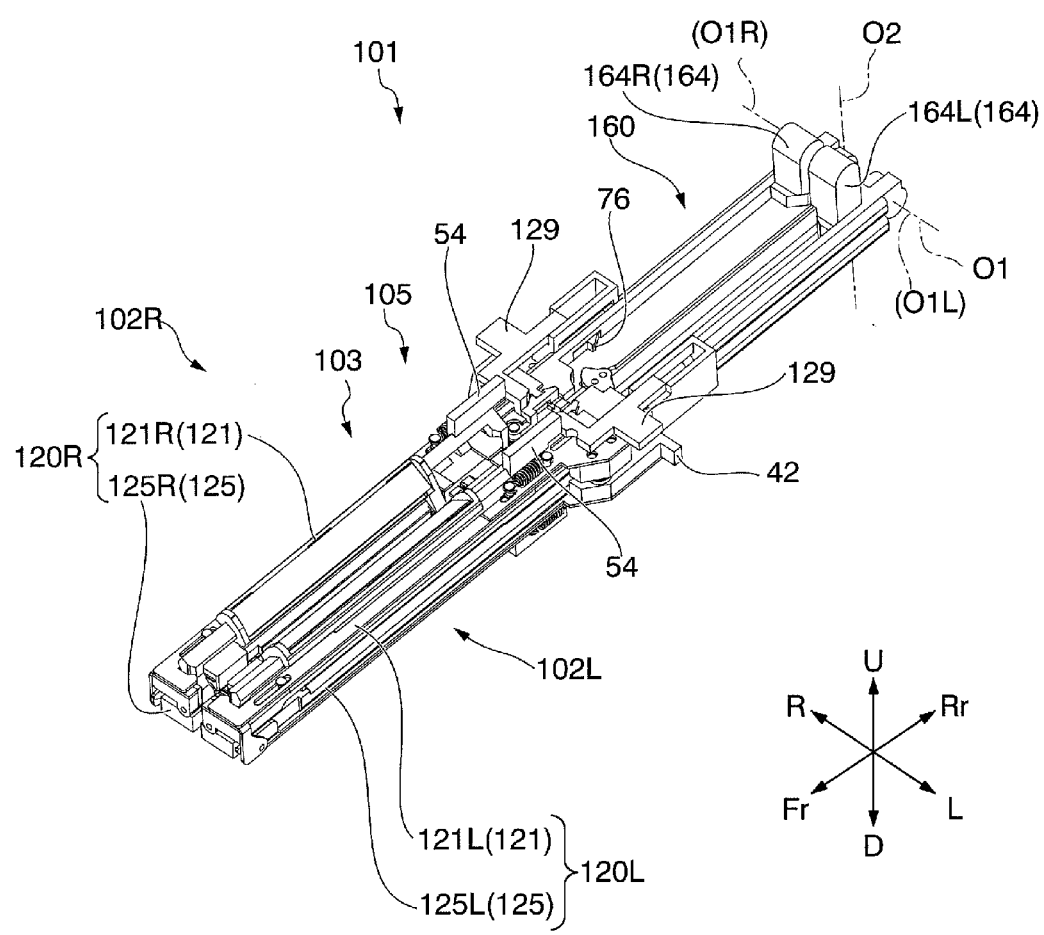
FIG. 37 is a perspective view showing the anastomotic apparatus according to a second embodiment of the present invention, and shows the state when the two sets of clamps are closed.
Figure 38:
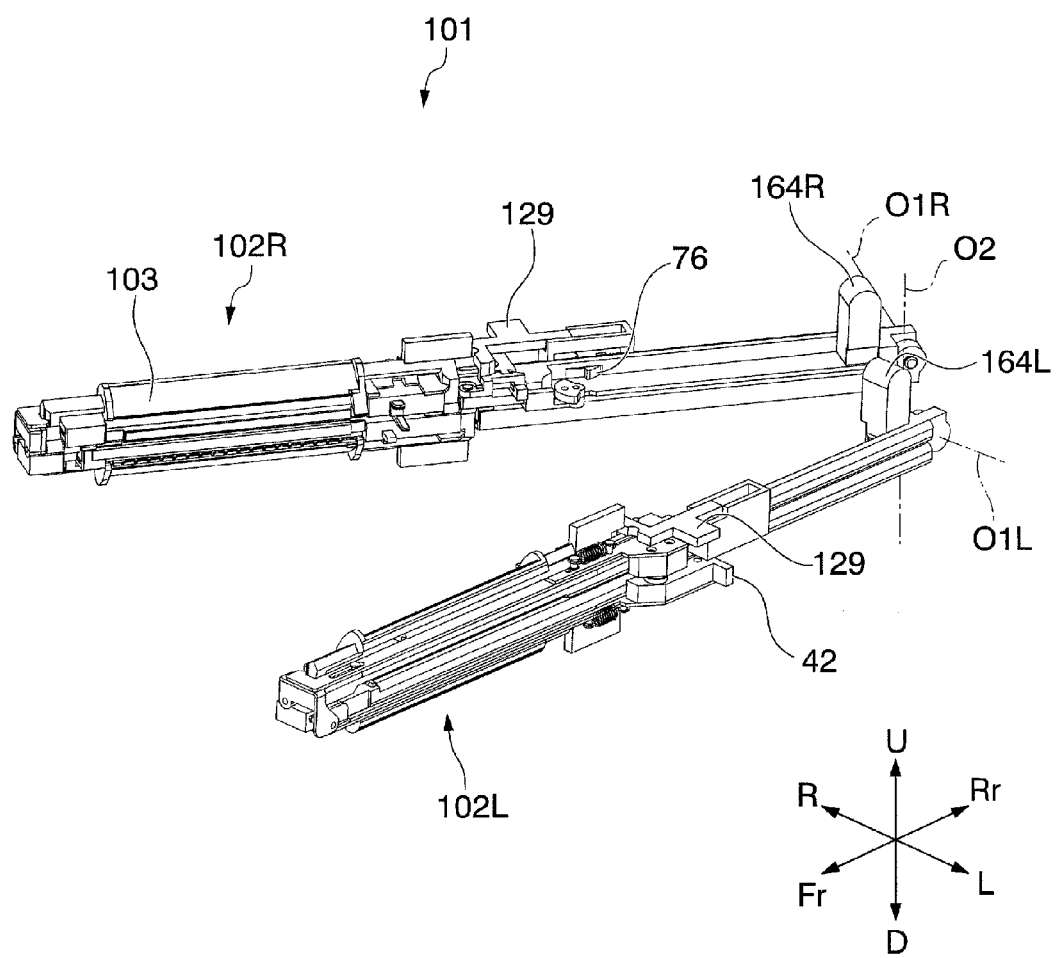
FIG. 38 is a perspective view showing the anastomotic apparatus according to a second embodiment of the present invention, and shows the state when the two sets of clamps are spread open.

FIGS. 37 and 38 are views showing the anastomotic apparatus according to the present invention. Numeric symbol 101 indicates the anastomotic apparatus and numeric symbols 102R,102L indicate the clamps.

Figure 39:
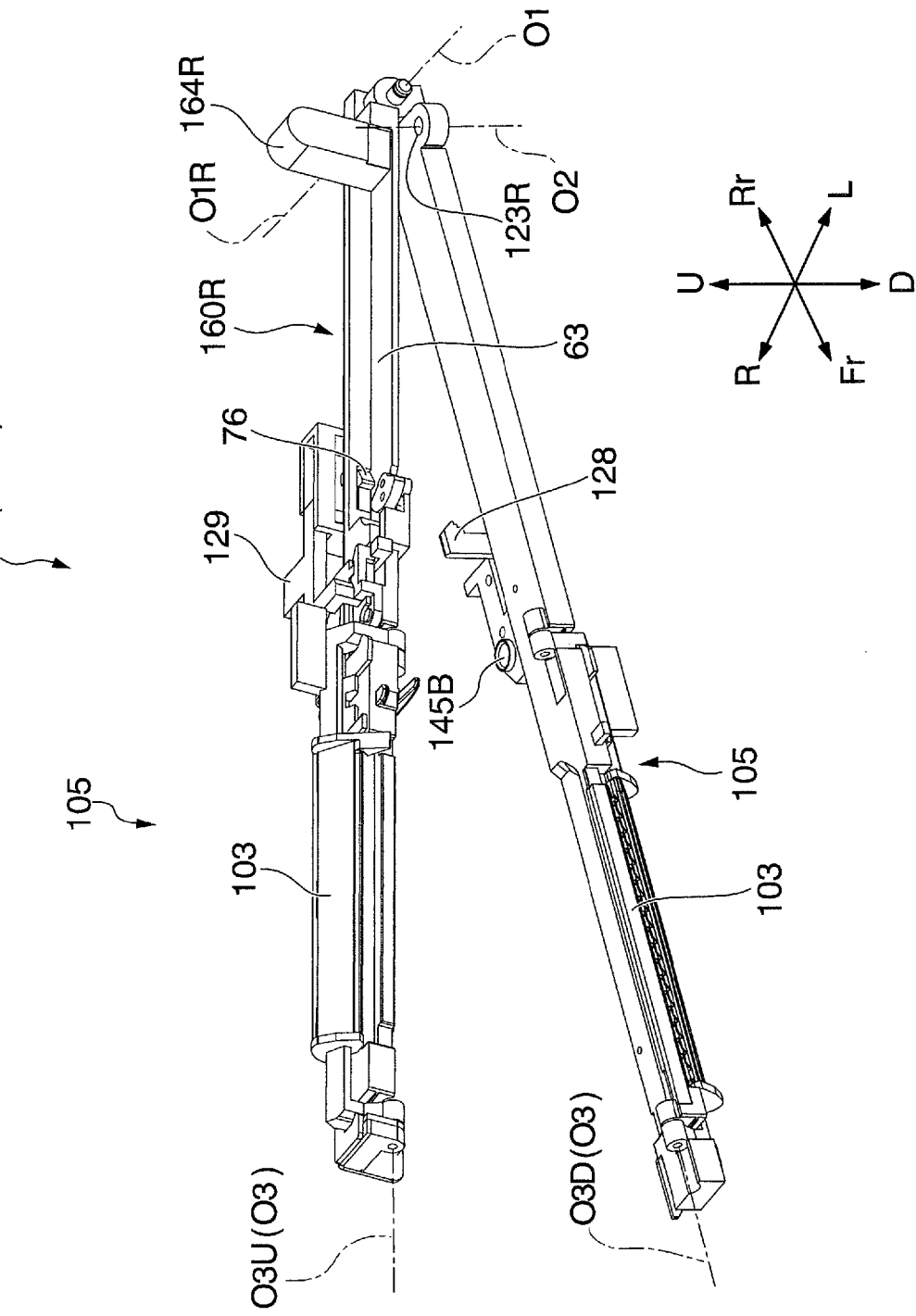
FIG. 39 is a perspective view showing the clamp on the right in the anastomotic apparatus according to a second embodiment of the present invention.
Figure 40:
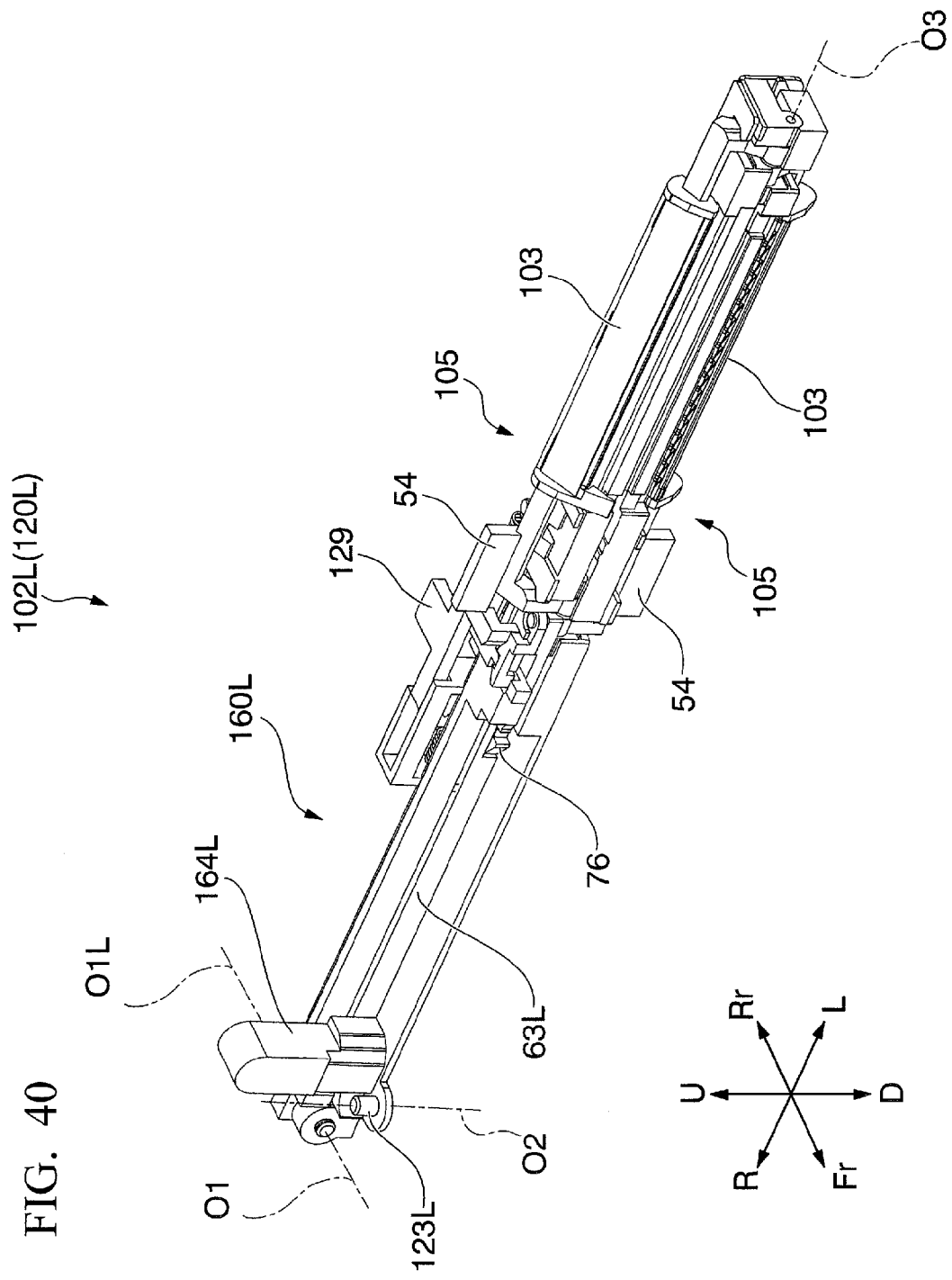
FIG. 40 is a perspective view showing the clamp on the left in the anastomotic apparatus according a second embodiment of the present invention.
Figure 41:
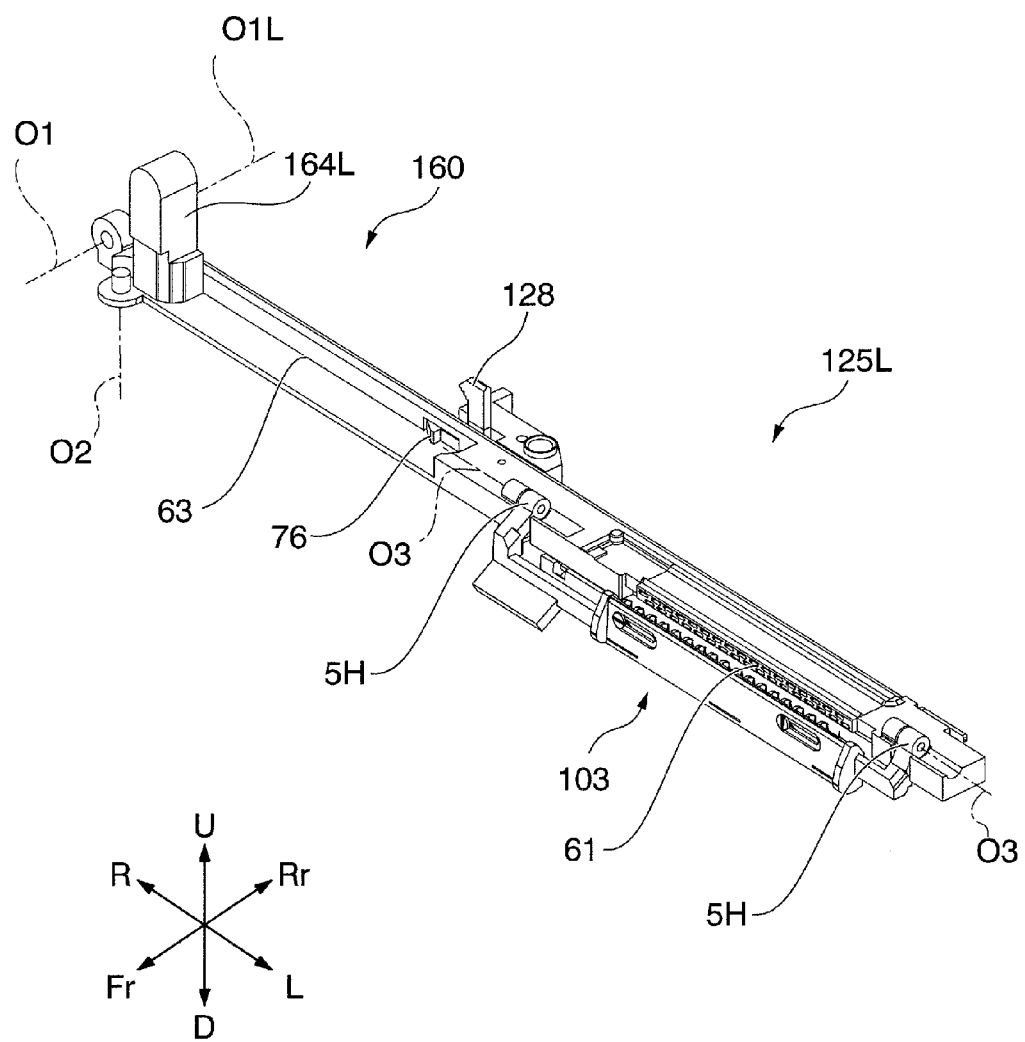
FIG. 41 is a perspective view showing a portion of the internal structure of the clamp on the left in the anastomotic apparatus according to a second embodiment of the present invention.

FIGS. 39 and 40 are views showing the paired clamp member 120R (formed from clamp member 121R and clamp member 125R) which composes the clamp 102R, and paired clamp member 120L (formed from clamp members 121L and clamp members 125L) which composes the clamp 102L. FIG. 41 is a view showing the clamp member 125L.

The symbols R, L, Fr, Rr, U and D along the coordinate axes shown in FIGS. 37 through 41 show directions associated with anastomotic apparatus 1 and its composing members, and shows right (R), left (L), Fr (front), up (U) and down (D) when the rear Rr ("handheld side" hereinafter) of the anastomotic apparatus 1 is held on the handheld side.

As shown in FIGS. 37 and 38, the anastomotic apparatus 101 is provided with a clamp 102R capable of rotating around axis O1R and a clamp 102L capable of rotating around axis O1L.

The clamps 102R and 102L are designed to be able to rotate around respective axes O1R,O1L.

Further, clamps 102R and 102L can be connected by inserting a connecting pin 123L, which is formed on the same axis as axis O2 which is perpendicular to the axis O1L which is formed to clamp 102L, into a connecting hole 123R, which is formed to the same axis as axis O2 which is perpendicular to the axis O1R formed in clamp 102R. Clamp 102R and clamp 102L are designed to enable mutual rotation around axis O2.

When the clamp 102R and the clamp 102L are connected and closed by rotating around the axis O2, the axis O1R of the clamp 102R and the axis O11 of the clamp 102L are disposed to the single axis O1.

A locking member (indicated by numeric symbol N in FIG. 1), not shown in these figures, is provided for closing the distal end side of the clamps when the clamps 102R and 102L are in the closed state, thereby preventing opening of the left and right clamps 102R,102L when the anastomosis is being performed.

Note that the axis O1 and the axis O2 do not signify absolute coordinates in space. Rather, they are axes that are standardized to the anastomotic apparatus 1 when it is formed with the clamps 2R,2L closed.

As shown in FIG. 39, the clamp 102R is provided with a clamp member 121R and a clamp member 125R.

The clamp members 121R and 125R are respectively provided with a fork which is formed extending in the stapling direction when employed as anastomotic apparatus 101; an organ gripping mechanism 103 which is disposed in the longitudinal direction of clamp members 121R,125R; an everting mechanism 105; a firing mechanism 160 and an anvil member 67; and a grip controlling mechanism.

The everting mechanism 105 is designed to evert the edges of the organ tissue which is gripped by the organ gripping mechanisms 103, by rotating the respective organ gripping mechanisms 103 around the everting axes O3U,O3D which are formed in the longitudinal direction of the respective clamp members 121R,125R.

Further, the clamping surface of the clamp member 121R and the clamping surface of the clamp member 125R are formed to enable opposition of the surfaces, and to enable holding of the organ tissue by closing the clamp member 121R and the clamp member 125R.

As shown in FIG. 40, the clamp 102L is provided with a clamp member 121L and a clamp member 125L.

Clamp members 121L and 125L are respectively provided with a fork which is formed extending in the stapling direction when employed as anastomotic apparatus 101; an organ gripping mechanism 103 which is disposed in the longitudinal direction of clamp members 121L,125L; an everting mechanism 105; a firing mechanism 160 and an anvil member 67; and a grip controlling mechanism.

The everting mechanism 105 is designed to evert the edges of the organ tissue which is gripped by the organ gripping mechanisms 103, by rotating respective organ gripping mechanisms 103 around the everting axes O3 (O3U,O3D) which are formed in the longitudinal direction of the respective clamp members 121R,125R. Note that when clamps 120R,102L are closed, everting axis O3U and everting axis O3D of clamps 120R,102L are disposed to the same single axis, everting axis O3.

Further, the clamping surface of the clamp member 121L and the clamping surface of the clamp member 125L are formed to enable opposition of the surfaces, and to enable gripping of the organ tissue by closing the clamp member 121L and the clamp member 125L.

Note that the clamp 102R and the clamp 102L are designed to be able to close around the axis O2 when an everting operation has been performed for each of the everting mechanisms 105 that are provided respectively to the clamp members 121R, 125R, 121L, 125L.

Further, the clamps 102R and 102L are designed to form two groups of mutually opposed clamp member pairs 121 and clamp member pairs 125 when the anastomotic apparatus 101 is closed about the axis O2.

The surface which faces both the space between the clamp member 121R and the clamp member 121L which form the clamp member pair 121, and the space between clamp member 121R and clamp member 121L which form the clamp member pair 125, forms the staple facing surface (stapling surface).

Once the anastomotic apparatus 1 is formed, a stapling mechanism, having a firing mechanism 160 and an anvil member 67, is formed respectively between the mutually opposing clamp member 121R and clamp member 121L, and the clamp member 121L and the clamp member 121R, with the firing mechanism 160 disposed to the clamp member 121R and the clamp member 125L, and the anvil member 67 disposed to the clamp members 121L and 125R.

FIG. 41 shows the abbreviated structure of the firing mechanism 160 which is disposed to the clamp member 125L of clamp 102L. The firing mechanism 160 is provided with a staple housing 61 for housing the staples S and an ejector. The ejector is provided with an ejection knob 164L and an ejection slider 63.

Further, it is preferable that the clamp 102R and the clamp 102L are covered by an externally visible cover of lightweight plastic resin, for example, which limits reactivity with the organ tissue.

Figure 42:
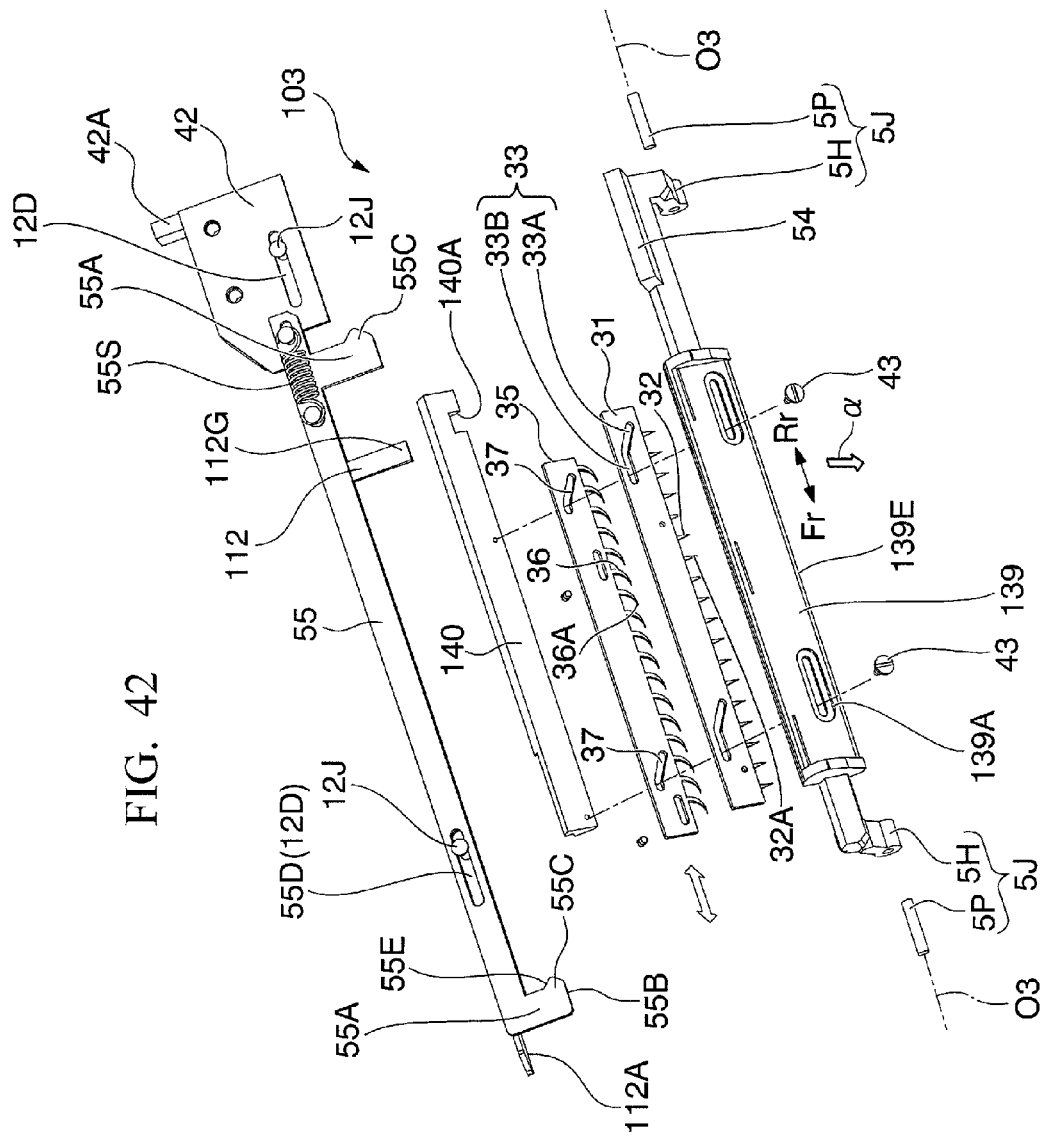
FIG. 42 is a perspective view showing the organ gripping mechanism in the anastomotic apparatus according to a second embodiment of the present invention.
Figure 43A:
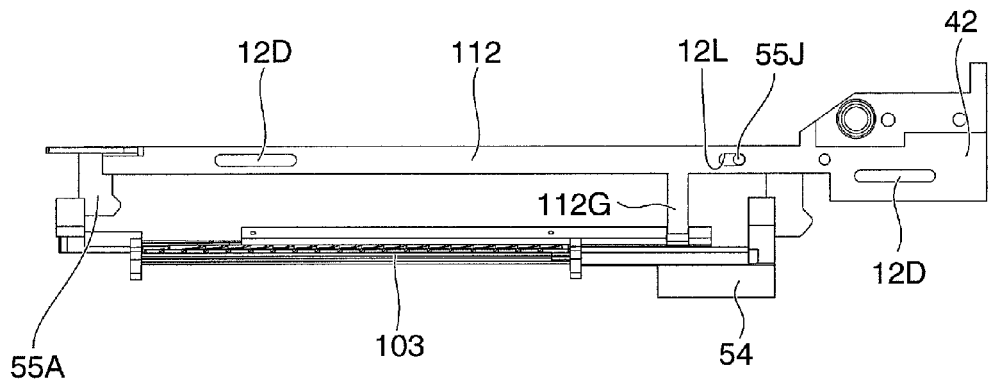
FIG. 43A is a view for explaining the everting mechanism of the anastomotic apparatus according to a second embodiment of the present invention, and is a planar view showing the pre-eversion state as seen from the clamping surface side.
Figure 43B:
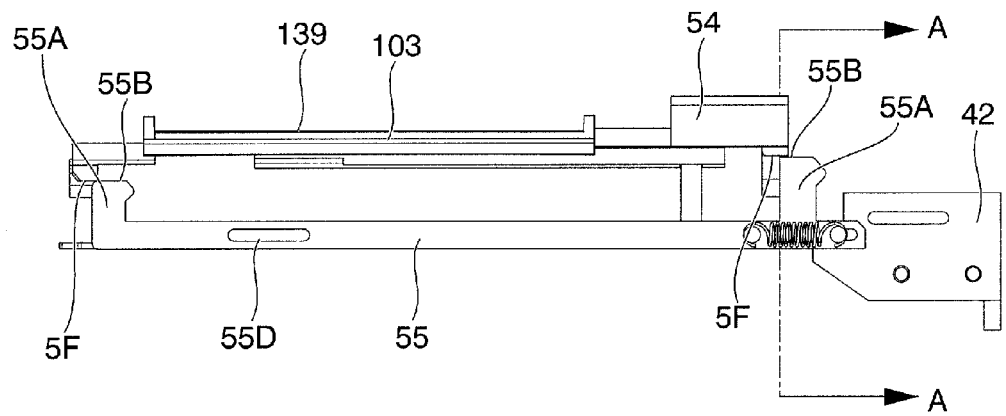
FIG. 43B is a view for explaining the everting mechanism of the anastomotic apparatus according to a second embodiment of the present invention, and is a planar view showing the pre-eversion state as seen from the side opposite the clamping surface.
Figure 43C:
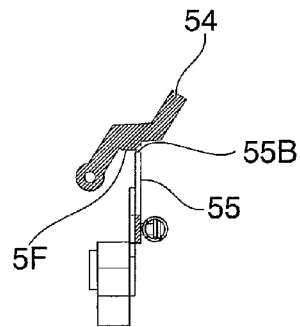
FIG. 43C is a view for explaining the everting mechanism of the anastomotic apparatus according to a second embodiment of the present invention, and is a view shown in cross-section along the line A-A in FIG. 43B.
Figure 44A:
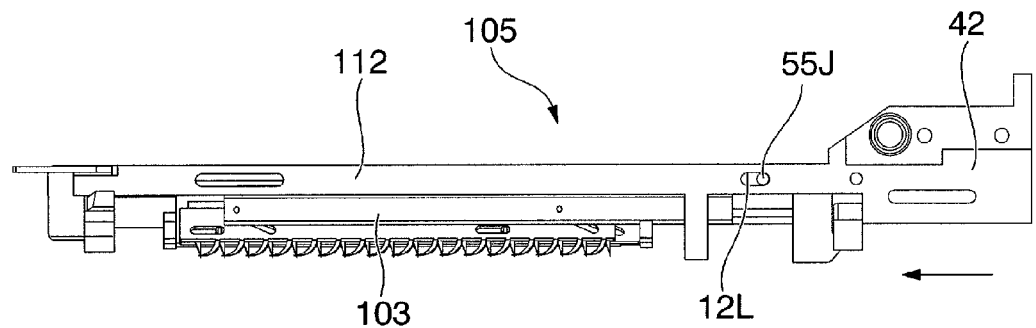
FIG. 44A is a view for explaining the everting mechanism of the anastomotic apparatus according to a second embodiment of the present invention, and is a planar view showing the post-eversion state as seen from the clamping surface side.
Figure 44B:
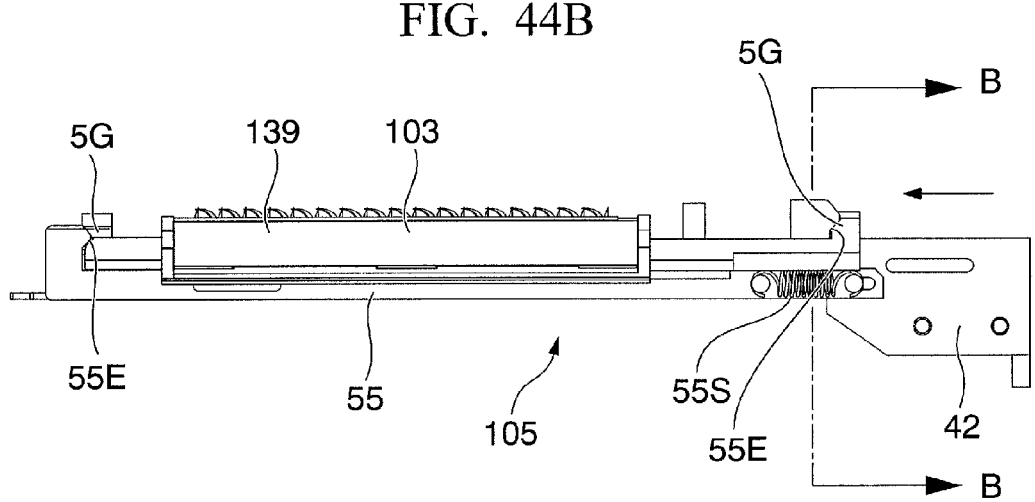
FIG. 44B is a view for explaining the everting mechanism of the anastomotic apparatus according to a second embodiment of the present invention, and is a planar view showing the post-eversion state as seen from the side opposite the clamping surface.
Figure 44C:
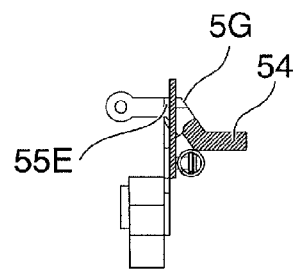
FIG. 44C is a view for explaining the everting mechanism of the anastomotic apparatus according to a second embodiment of the present invention, and is a view shown in cross-section along the line B-B in FIG. 44.
Figure 45:
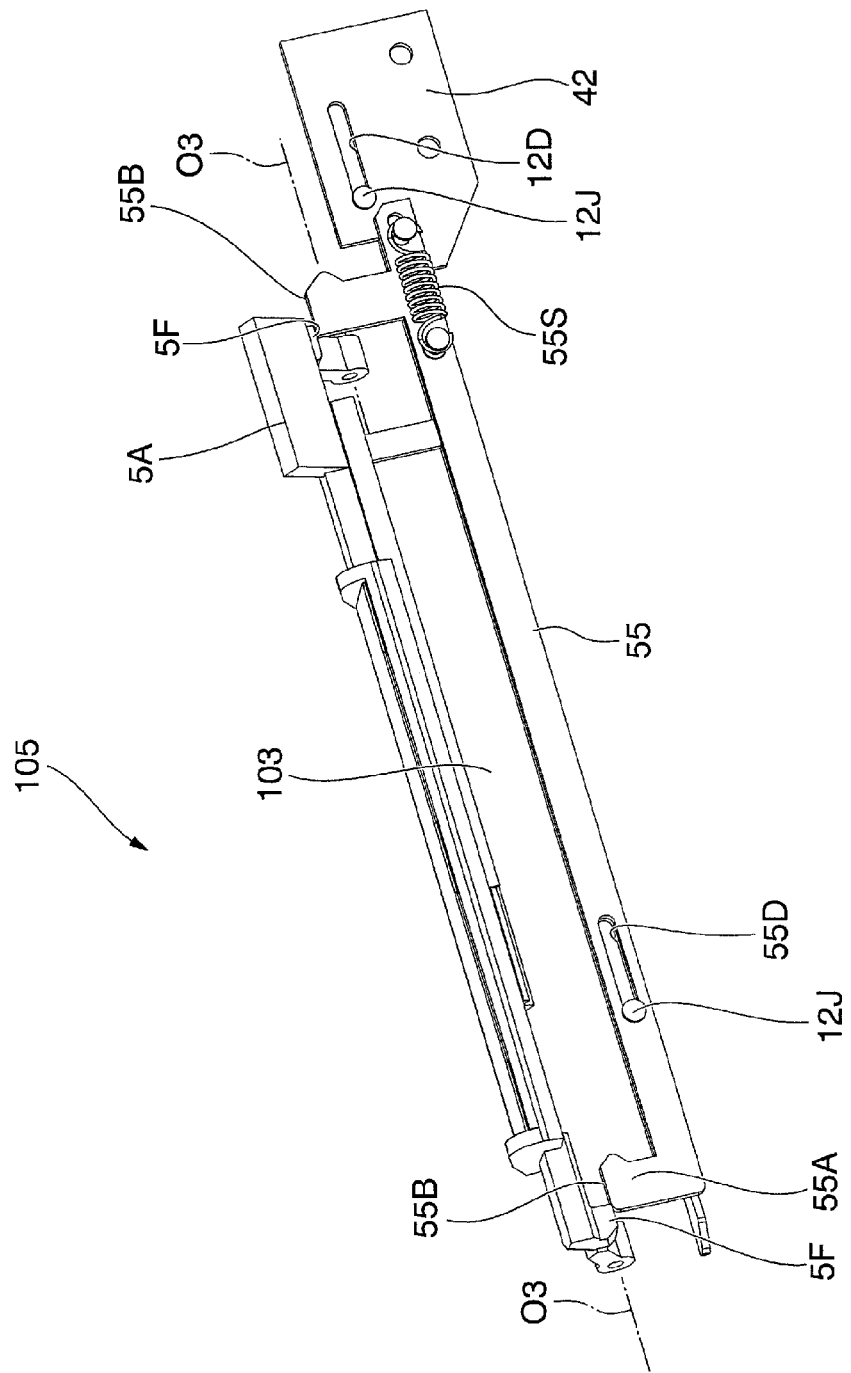
FIG. 45 is a perspective view showing the state before eversion and is for explaining the everting mechanism of the anastomotic apparatus according to a second embodiment of the present invention.
Figure 46:
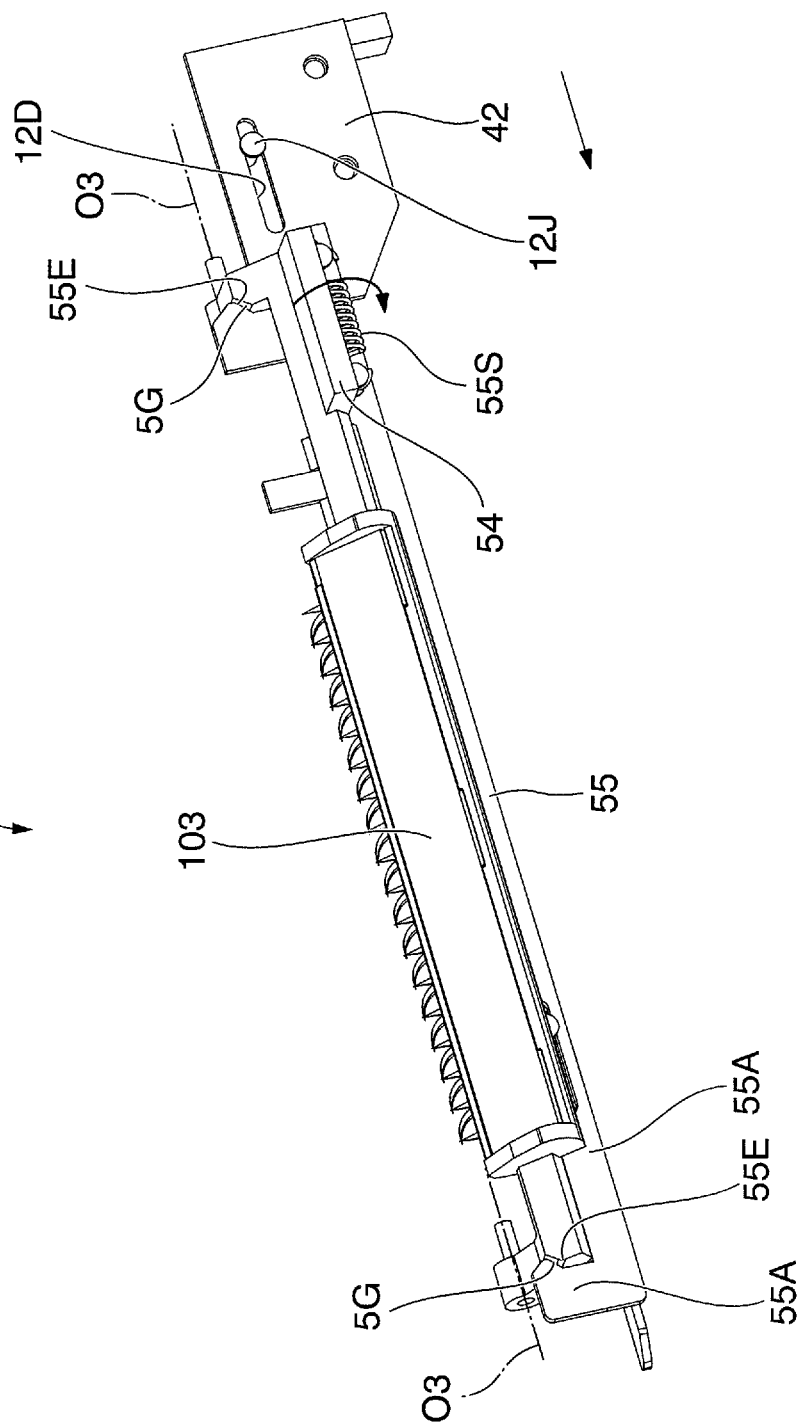
FIG. 46 is a perspective view showing the state after eversion and is for explaining the everting mechanism in the anastomotic apparatus according to a second embodiment of the present invention.
Figure 47:
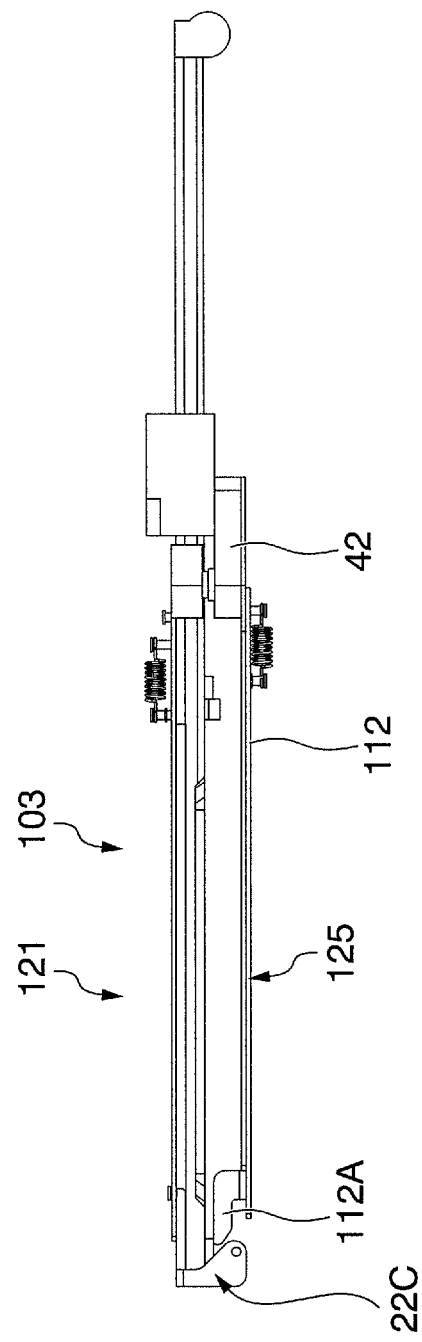
FIG. 47 is a view for explaining an example of the clamp member space maintaining mechanism in the anastomotic apparatus according to the second embodiment, and shows the state prior to action of the organ gripping mechanism.

As shown in FIG. 42, the organ gripping mechanism 103 is provided with a pointed teeth member (first gripping teeth plate member) 31, a rake teeth member (second gripping teeth plate member) 35, a housing 139, a gripping teeth operating member (gripping teeth actuating member) 140, and an engaging pin (first engaging member, second engaging member) 43. Housing 139, pointed teeth member 31, rake teeth member 35, and gripping teeth operating member 140 are disposed from the front surface in this order overlying one another, and are designed to grip about the stapling site on the organ tissue.

Further, as shown in FIG. 42, the organ gripping mechanism 103 is connected to a connecting plate 112 and an everting position engaging member 140. The connecting plate 112 and the everting position engaging member 140 undergo relative displacement in the direction of the pointed teeth member 31 and the rake teeth member 35 when gripping manipulation of the organ gripping mechanism 103 is performed, and undergo relative displacement in the direction of rotation (i.e., in a direction which transects the hook) when an everting operation of the organ gripping mechanism 103 is performed.

Further, the housing 139 is capable of containing the pointed teeth member 31 and the rake teeth member 35, including the tips 32A of the pointed teeth 32 and the tips 36A of the rake teeth 36, so that exposure of the tip end side of the pointed teeth 32 and the rake teeth 36 is prevented.

Note that in this embodiment, the phrase "piercing direction" means the direction in which the pointed teeth are pressed against the outer side of the organ tissue (i.e., the direction of displacement of the pointed teeth).

The structures of the pointed teeth member 31, the rake teeth member 35, pointed teeth 32 and rake teeth 36 are the same as in the case of the organ gripping mechanism 3 according to the first embodiment. Accordingly, the same numeric symbols are applied and an explanation thereof is omitted.

The housing 139 is disposed to the front surface side of the pointed teeth member 31 and the rake teeth member 35, and is designed to prevent damage to the pointed teeth 32 and the rake teeth 36 and contact with the operator by preventing exposure of the tip side 32A of the pointed teeth 32 and the tip side 36A of the rake teeth 36. Further, two long holes 139A are formed in alignment in the direction of the pointed teeth 32 array. The engaging pin 43 can move along the long holes 139A. The pointed teeth 32 and the rake teeth 36 are exposed from the edge 139E of the housing 139 by moving the pointed teeth 32 and the rake teeth 36 in the direction indicated by the arrow α. In addition, a cut protector identical to that of housing 39 is formed to housing 139.

Eversion rotating supports 5H for forming the everting axis O3 (O3U or O3D) are formed at either end of the housing 139.

Note that the eversion rotating support 5H for the organ gripping mechanism 103 forming the upper clamp members 121R,121L, and the eversion rotating support 5H for the organ gripping mechanism 103 forming the lower clamp members 125R,125L, which form the clamps 102R,102L, are disposed at different positions along the longitudinal direction so that the everting axis O3U and the everting axis O3D form a single everting axis O3 when the clamps 102R,102L are closed.

Two engaging pins 43 are provided to the gripping teeth operating member 140. By manipulating the operating knob 42, the engaging pins 43 undergo relative displacement with respect to the housing 139, the rake teeth member 35 and the pointed teeth member 31, moving from the handheld side to the distal end side of the clamp members 120R,120L.

Note that in this embodiment the first drive mechanism and the second drive mechanism are both connected to the operating knob 42 and manipulate operating knob 42. As a result, the rake teeth 36 move one pitch in the longitudinal direction with respect to the pointed teeth 32 and are exposed from the edge 139E of the housing 139.

The gripping teeth operating member 140 engages with the engaging projection 112G of the connecting plate 112 via an engaging recess 140A. Note that the engaging projection 112G is designed so that the width of its end surface in the longitudinal direction is formed to be slightly narrower than the engaging recess 140A.

As a result, the operating knob 42 is operated to move the connecting plate 112 in the advancing direction. The gripping teeth operating member 140 thus advances, so that the pointed teeth 32 and the rake teeth 36 of the organ gripping mechanism 103 are placed in the gripping state. On the other hand, when the everting mechanism 105 is operated, even if the eversion operating knob 54 is rotated, the operating knob 42 undergoes relative displacement in the direction of rotation of the eversion operating knob 51, thus preventing rotation of the operating knob 42.

Next, the everting mechanism 105 will be explained with reference to FIG. 43A through FIG. 46.

The everting mechanism 105 is provided with a design in which an eversion operating knob (everting operator) 54 for performing the everting manipulation of the organ gripping mechanism 103 by remote operation is rotated to horizontally transect the longitudinal direction of the fork. As a result, the organ gripping mechanism 103 rotates around the everting axis O3 and the organ tissue is everted by moving within an eversion movement range which extends from a pre-eversion position to a post-eversion position.

The everting mechanism 105 is provided with an eversion position engaging member 55 which moves together with the connecting plate 112 of the organ gripping mechanism 103.

The eversion position engaging member 55 is designed to move together with the housing 139 as well as the connecting plate 112. When the operating knob 42 is manipulated, the eversion position engaging member 55 is designed to move along with the connecting plate 112 to the gripping position for the pointed teeth member 31 and the rake teeth member 35. In this case, the everting position engaging member 55 and the connecting plate 112 have a guide hole 55D which is formed in the everting position engaging member 55 and a guide hole 12D (which communicates with guide hole 55D) which is formed in the connecting plate 112 respectively, and move with guidance by pin 12.

As shown in FIGS. 43A-43C and FIG. 45, contact part 5F of the organ gripping mechanism 103 and pre-eversion position engaging part 55B are engaged until the pointed teeth member 31 and the rake teeth member 35 are moved to the gripping position by the operating knob 42, engaging the organ gripping mechanism 103 at the pre-eversion position.

As shown in FIGS. 44A-44C and FIG. 46, when an eversion operation is performed on the organ gripping mechanism 103, the post-eversion position engaging part 5G and the post-eversion position engaging part 55E of the organ gripping mechanism 103 engage, thereby engaging the organ gripping mechanism 103 at the post-eversion position.

The eversion position engaging member 55 and the connecting plate 112 can undergo relative displacement within a specific range as a result of the long holes 12L and the engaging pin 55J. When the organ gripping mechanism 103 is everted, the eversion position engaging member 55 moves relative to the connecting plate 112, causing the housing 139 (contact part 5F) to ride over the exchange profile part 55C of the engaging part 55A of the eversion position engaging member 55. As a result, the engagement with the organ gripping mechanism 103 is exchanged from the pre-eversion position engaging part 55B to the post-eversion engaging part 55G. Note that once the exchange is complete, the relative positions of the eversion position engaging part 55 and the connecting plate 112 return to their original positions due to spring 55S.

As a result, using the clamp members 121R, 121L, 125R, 125L, the organ gripping mechanism 103 can be held with certainty at the pre-eversion and post-eversion positions by means of a simple structure.

As in the case of the organ gripping mechanism 3, the organ gripping mechanism 103 which is disposed to the clamp member 121R and the organ gripping mechanism 103 which is disposed to the clamp member 125R, and the organ gripping mechanism 103 which is disposed to the clamp member 121L and the organ gripping mechanism 103 which is disposed to the clamp member 125L, are operated in synchrony by means of respective gripping action synchronizing mechanisms.

Note that the first gripping teeth plate member and the second gripping teeth plate member may be designed to permit mutual relative movement by connecting the gripping teeth drive to at least one of either the first gripping teeth plate member or the second gripping teeth plate member.

The clamp 102R, 102L is provided with a distal end space maintaining part for holding constant the space interval at the distal end side of the clamp members 121R,125R and the clamp members 121L,125L.

The connecting plate 112 composing the organ gripping mechanism 103 of the clamp members 125R,125L has a distal inclined part 112A formed thereto which slants from the distal to the caudal side and away from the clamp members 121R,121L, as shown in FIG. 47 through FIG. 50.

Figure 48:
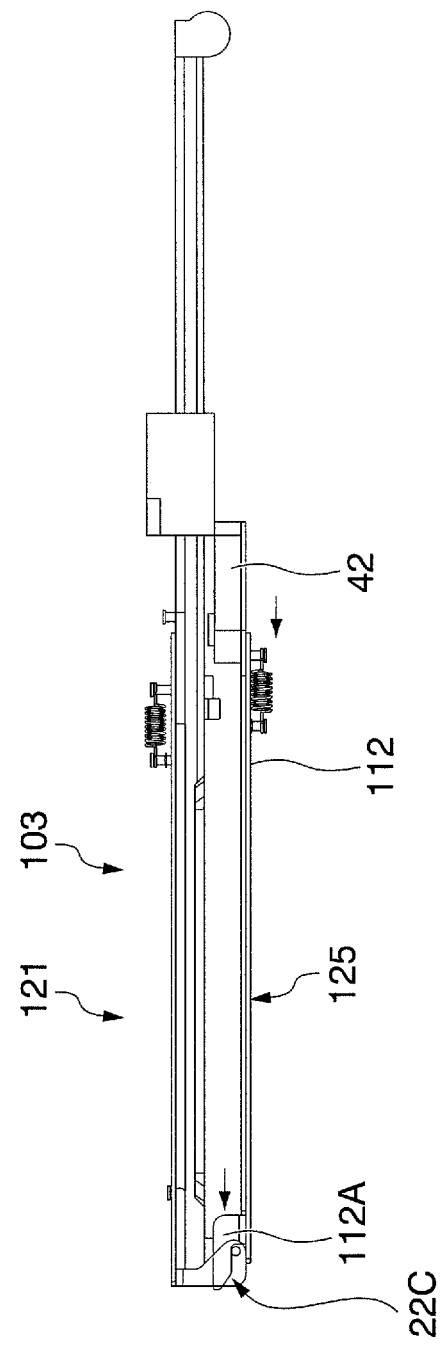
FIG. 48 is a view for explaining an example of the clamp member space maintaining mechanism in the anastomotic apparatus according to the second embodiment, and shows the state after action of the organ gripping mechanism.
Figure 49:
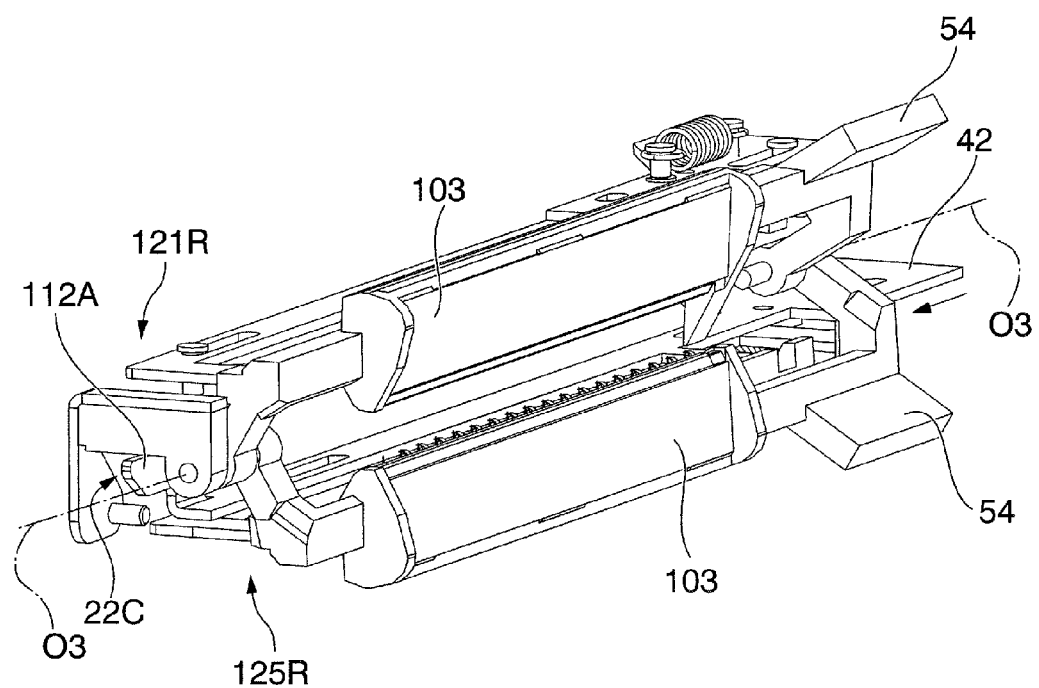
FIG. 49 is a perspective view showing the state prior to eversion of the organ gripping mechanism in the anastomotic apparatus according to a second embodiment.
Figure 50:
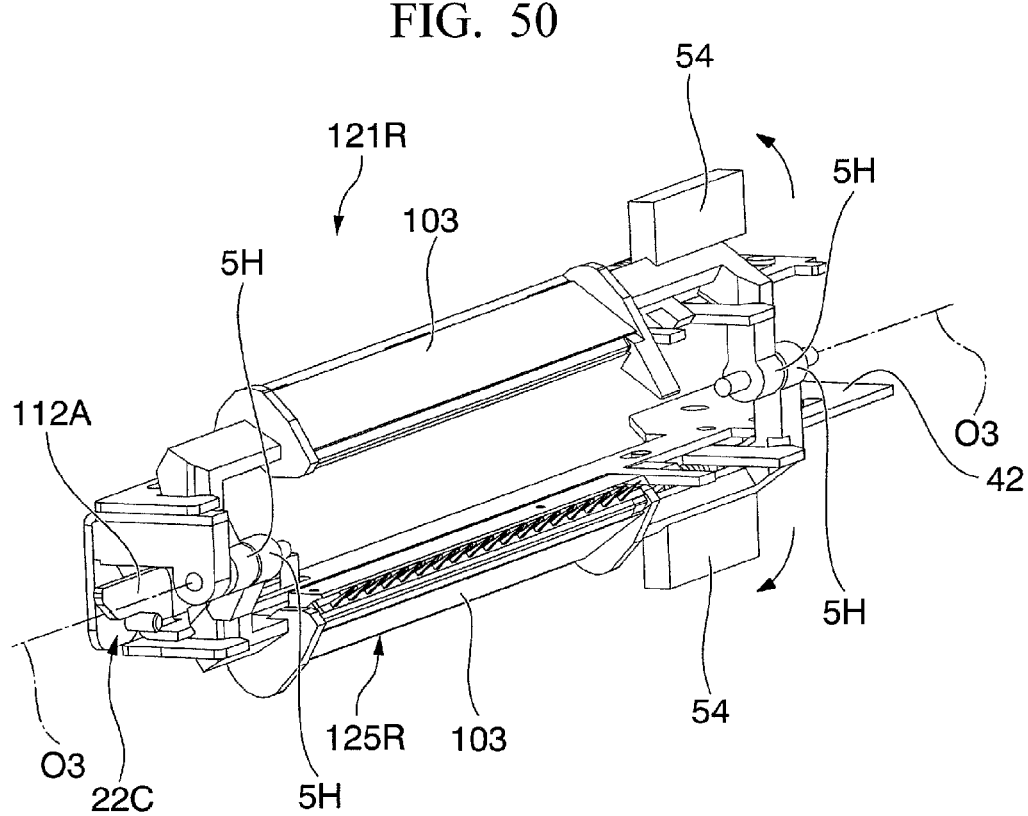
FIG. 50 is a perspective view showing the state after eversion of the organ gripping mechanism in the anastomotic apparatus according to a second embodiment.

As result, the operating knob 42 is manipulated to carry out gripping of the organ tissue P by the organ gripping mechanism 103 as shown in FIG. 48 and FIG. 50, causing the distal inclined part 112A to be housed in the connecting housing 22C of the clamp members 121R,121L. As a result, the provided design enables a specific space interval to be formed between the surfaces of the clamps 102R,102L easily and with certainty.

The distal inclined part 112A and connecting housing 22C form the distal end space maintaining part.

Next, the operation of the everting mechanism 105 will be explained with reference to FIGS. 51A to 54C.

Figure 51A:
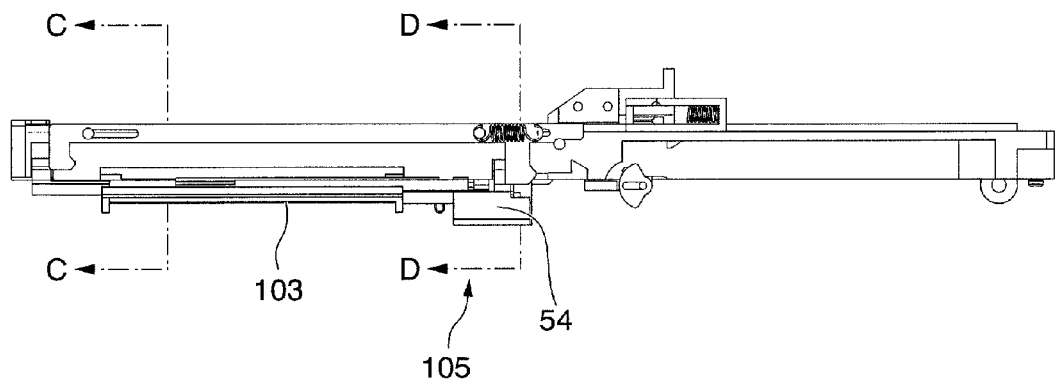
FIG. 51A is a view for explaining the everting mechanism in the anastomotic apparatus according to a second embodiment, and is a planar view showing the state prior to the eversion.

As shown in FIGS. 51A from 51C, the organ tissue P is gripped by the organ gripping mechanism 103.

Figure 51B:
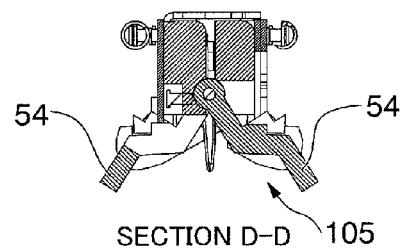
FIG. 51B is a view for explaining the everting mechanism in the anastomotic apparatus according to the second embodiment of the present invention, and is a view shown in cross-section along the line D-D of FIG. 51A.
Figure 51C:
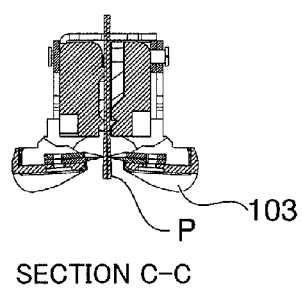
FIG. 51C is a view for explaining the everting mechanism in the anastomotic apparatus according to the second embodiment of the present invention, and is a view shown in cross-section along the line C-C of FIG. 51A.

The eversion operating knob 54 is at the position shown in FIG. 51B at this time. The gripped organ tissue P is in an arrangement such as shown in FIG. 51C.

Figure 52A:
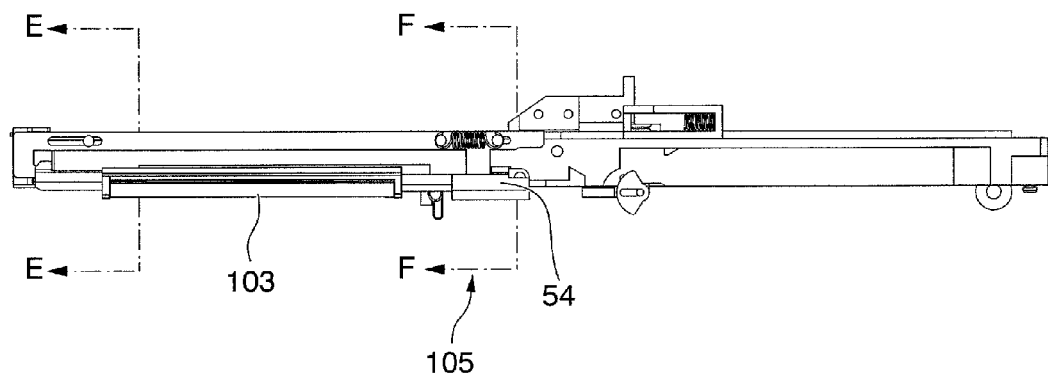
FIG. 52A is a view for explaining the everting mechanism in the anastomotic apparatus according to the second embodiment of the present invention, and is a planar view showing the state during eversion.
Figure 52E:
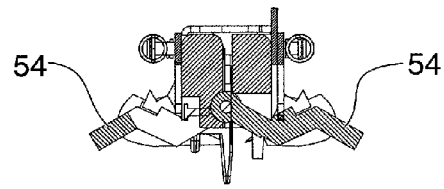
FIG. 52B is a view for explaining the everting mechanism in the anastomotic apparatus according to a second embodiment of the present invention, and is a view shown in cross-section along the line F-F of FIG. 51A.
FIG. 52C is a view for explaining the everting mechanism in the anastomotic apparatus according to a second embodiment of the present invention, and is a view shown in cross-section along the line E-E of FIG. 51A.
Figure 52C:
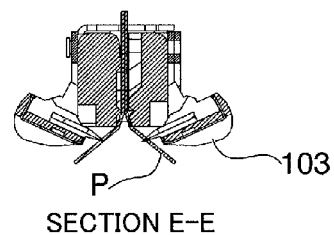
Figure 53A:
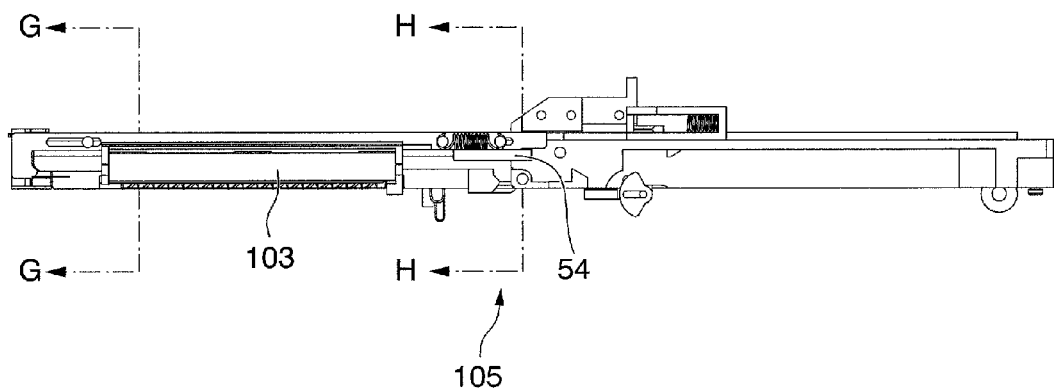
FIG. 53A is a view for explaining the everting mechanism in the anastomotic apparatus according to a second embodiment of the present invention, and is a planar view showing the state after the eversion.
Figure 53B:
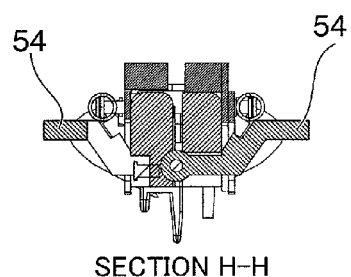
FIG. 53B is a view for explaining the everting mechanism in the anastomotic apparatus according to a second embodiment of the present invention, and is a view shown in cross-section along the line H-H of FIG. 51A.
Figure 53C:
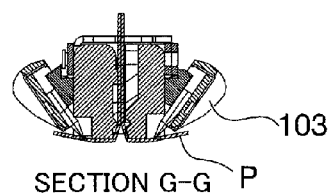
FIG. 53C is a view for explaining the everting mechanism in the anastomotic apparatus according to a second embodiment of the present invention, and is a view shown in cross-section along the line G-G of FIG. 51A.

Next, the eversion operating knob 54 is rotated and the organ tissue P is everted by the organ gripping mechanism 103. As a result, as shown in FIG. 52A to FIG. 52C the eversion of the organ tissue P begins. The views shown in FIG. 52A through FIG. 52C are the states during the eversion. The eversion operating knob 54 is at the position shown in FIG. 52B and the gripped organ tissue P is in the state shown in FIG. 52C.

Figure 54A:
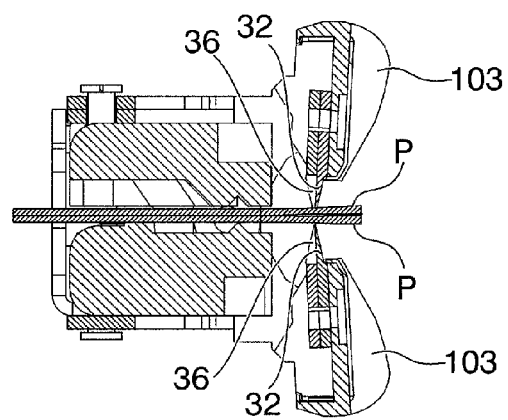
FIG. 54A is a view for explaining the everting mechanism in the anastomotic apparatus according to a second embodiment of the present invention, and is a cross-sectional view showing the state before the organ tissue is everted.
Figure 54B:
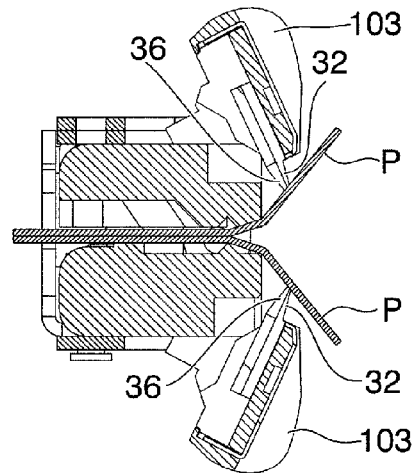
FIG. 54B is a view for explaining the everting mechanism in the anastomotic apparatus according to a second embodiment of the present invention, and is a cross-sectional view showing the state during eversion of the organ tissue.
Figure 54C:
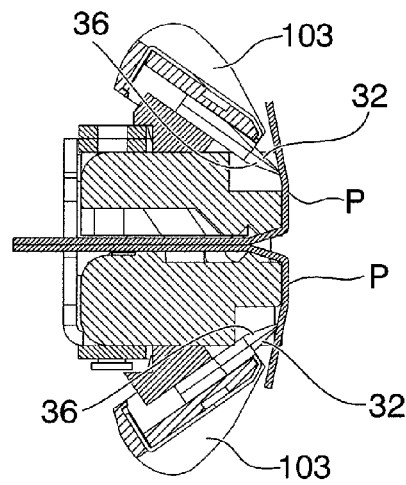
FIG. 54C is a view for explaining the everting mechanism in the anastomotic apparatus according to a second embodiment of the present invention, and is a cross-sectional view showing the state after eversion of the organ tissue.

The views shown in FIG. 54A through 54C show the process of everting the organ tissue P by rotating the organ tissue mechanism 103. FIG. 54A shows the pre-eversion state, FIG. 54B shows the state during eversion, and FIG. 54C shows the post-eversion state.

Next, the lock releasing mechanism in the anastomotic apparatus 101 will be explained with reference to FIG. 55A through FIG. 61.

Figure 55B:
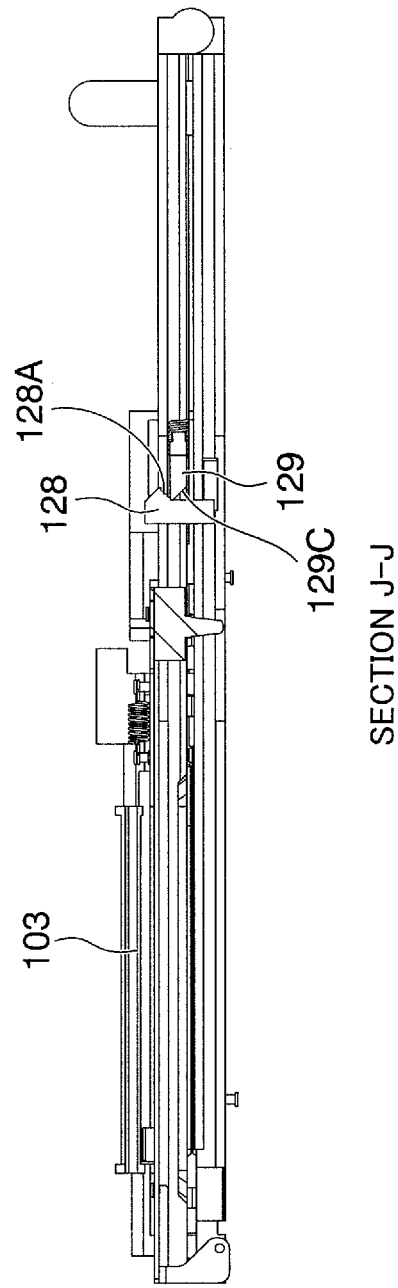
FIG. 55B is a view for explaining the lock releasing mechanism in the anastomotic apparatus according to a second embodiment of the present invention, and is a view shown in cross-section along the line J-J in FIG. 55A.
Figure 55C:
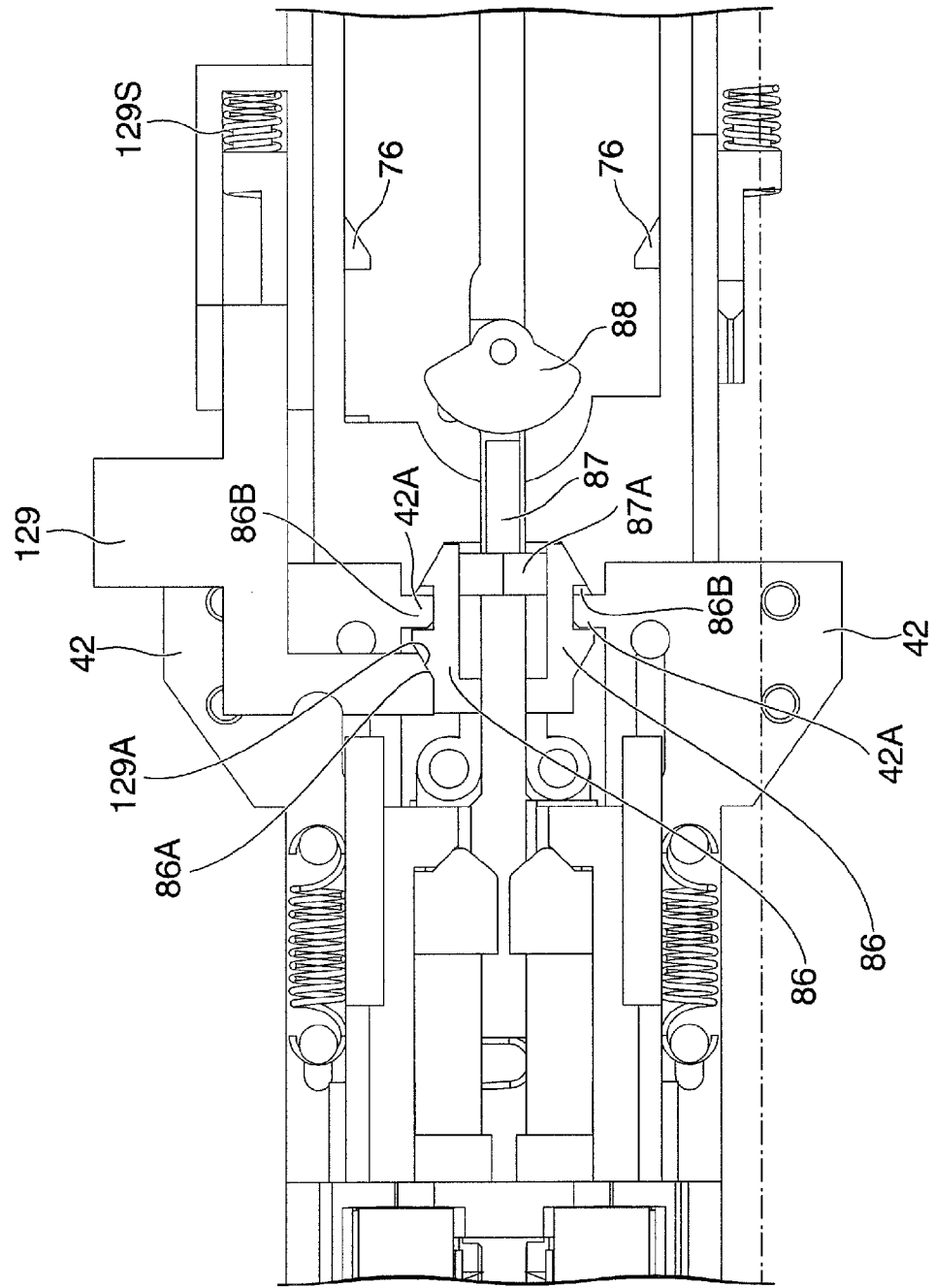
FIG. 55C is an enlarged view for explaining the essential components of the lock releasing mechanism in the anastomotic apparatus according to a second embodiment of the present invention.
Figure 56A:
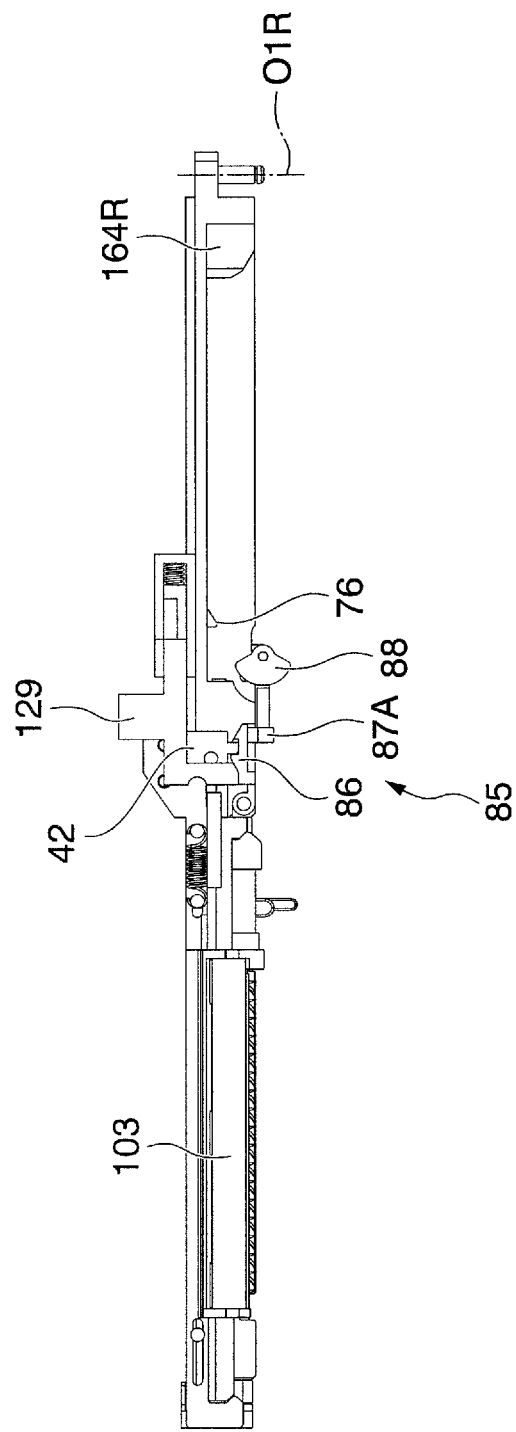
FIG. 56A is a planar view for explaining the lock releasing mechanism in the anastomotic apparatus according to a second embodiment of the present invention.
Figure 56B:
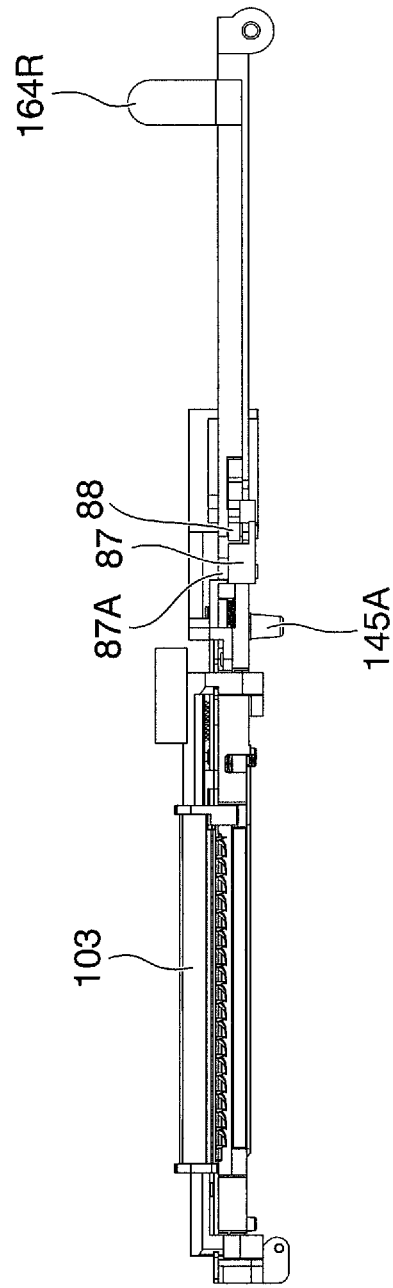
FIG. 56B is a lateral view for explaining the lock releasing mechanism in the anastomotic apparatus according to a second embodiment of the present invention.
Figure 57A:
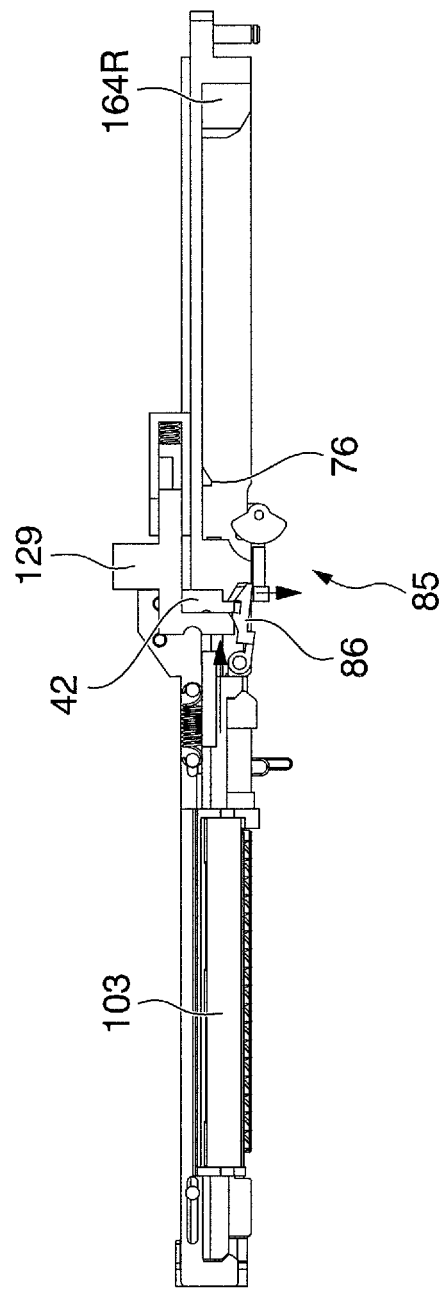
FIG. 57A is a planar view for explaining the lock releasing mechanism in the anastomotic apparatus according to a second embodiment of the present invention.
Figure 57B:
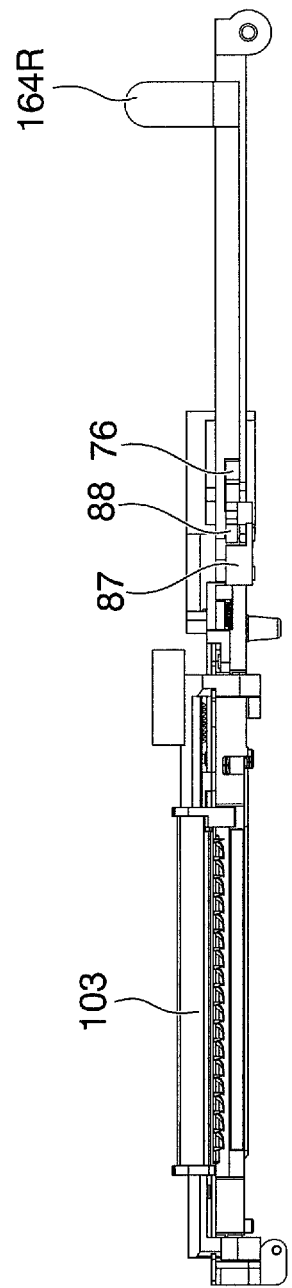
FIG. 57B is a lateral view for explaining the lock releasing mechanism in the anastomotic apparatus according to a second embodiment of the present invention.

The lock releasing mechanism is provided with a release knob 129 and a release knob controlling mechanism 85 as shown in FIG. 55A through FIG. 55C. When the ejection knobs 164R,164L are advanced and reach the leading edge, they are constrained by the ejection locking member 76 (forward ejector locking mechanism). Note that either of the ejection knobs 164R,164L may be operated first, with the ejector 164 which is operated subsequently being constrained.

Once the ejection knob 164R and the ejection knob 164L have both been operated to complete the anastomosis procedure, the release knob controlling mechanism 85 is activated to operate the release knob 129, thus releasing the grip by the vertical lock and the organ gripping mechanism 103.

The release knob 129 is for releasing the vertical lock 27 which, together with the engaging projection 128, forms and locks the vertical lock on the clamps 102R,102L. The release knob 129 is biased toward the distal end side by the spring 129S. The vertical knob is released by operating the release knob 129 on the handheld side.

The release knob 129 is provided with an engaging projection 129A and a locking member 129B for constraining the movement in the longitudinal direction of the release knob 129. The distal end of the locking member 129B engages with the engaging part 128A which is formed to the engaging projection 128. Provided that the release knob 129 is not operated to release the lock when the upper clamp members 121R,121L and the lower clamp members 125R,125L are closed, then the upper clamp members 121R,121L and the lower clamp members 125R,125L do not open.

An engaging projection 128 is disposed to the lower clamp members 125R,125L and the engaging member 129B of the release knob 129 is disposed to the upper clamp members 121R,121L.

The engaging projection 28 consists of a plate-shaped member which extends toward the upper clamp members 121R,121L. A triangular-shaped engaging part 128A is formed to engaging part 28 for engaging on the distal end side with the engaging projection 129B.

A plurality of engaging grooves are formed to engaging part 128A parallel to the axes O1R or O1L.

The release knob controlling mechanism 85 is provided with a locking member 86 and a lock controlling member (engaging part controlling member) 87.

A pair of locking members 86 are symmetrically disposed to the right and left to clamp member 102R and clamp 102L respectively, extending in the longitudinal direction of the anastomotic apparatus 101. The locking member 86 is provided with a locking inclined part (second lock engaging part) 86A which widens outward from the front to the back edge in the right or left direction, and a locking recess (first lock engaging part) 86B which is formed as an inward concavity along the longitudinal direction on the right and left. Lock 86 is designed to rotate centered on the respective distal ends of locking inclined part 86A and locking recess 86B.

A lock controlling member 87 is provided with a rocking member 88 on the ejection knobs 164R,164L side, and can move in the longitudinal direction of the anastomotic apparatus 101 by means of a guide which is not shown in the figures. Lock controlling member 87 is designed to detect the action of the ejection knobs 164R,164L via the rocking member 88 and move toward the handheld side.

The lock controlling member 87 has a controlling projection 87A. When the right and left clamp 102R,102L are open, the lock controlling member 87 can move freely in the longitudinal direction. When the right and left clamp 102R,102L are closed, the controlling projection 87A is held between the right and left locking members 86.

When the controlling projections 87A are held between the rear ends of the right and left locking members 86, the rear ends of the locking members 86 spread outward in the right and left directions. When the controlling projections 87A are held between the front ends of the locking members 86, the rear ends of the locking members 86 change position so as to be directed inward in the right and left directions, so that contact becomes possible.

When the rear ends of the locking members 86 spread outward in the right and left directions, and a position change inward in the right and left directions is not possible, the locking inclined part 86A and the locking recess 86B of the locking member 86 are positioned outward in the right and left directions.

When the locking inclined part 86A and the locking recess 86B are positioned to the outside in the right and left directions, the inclined part 129A of the release knob 129 and the locking projection 42A of the operating knob 42 are engaged respectively with the locking inclined part 86A and the locking recess 86B, so that the release knob 129 is constrained in the longitudinal direction.

Note that in the lock releasing mechanism, the lock controlling member 87 is not held between the right and left locking members 86 when the clamps 102R and 102L are not closed, as shown in FIG. 56A through FIG. 57B. Thus, the operation of the organ gripping mechanism 103 and the release knob 129 can be carried out freely. In contrast, when the clamp 102R and the 102L are closed, it is not possible to operate the release knob 129 if the ejection knobs 164R,164L are not operated.

As a result, until the operation of the two ejectors is complete, gripping of the organ tissue P by the clamps 102R,102L and gripping of the organ tissue P by the organ gripping mechanism 103 can be maintained with certainty.

Next, the operation of the lock releasing mechanism will be explained.

Figure 58:
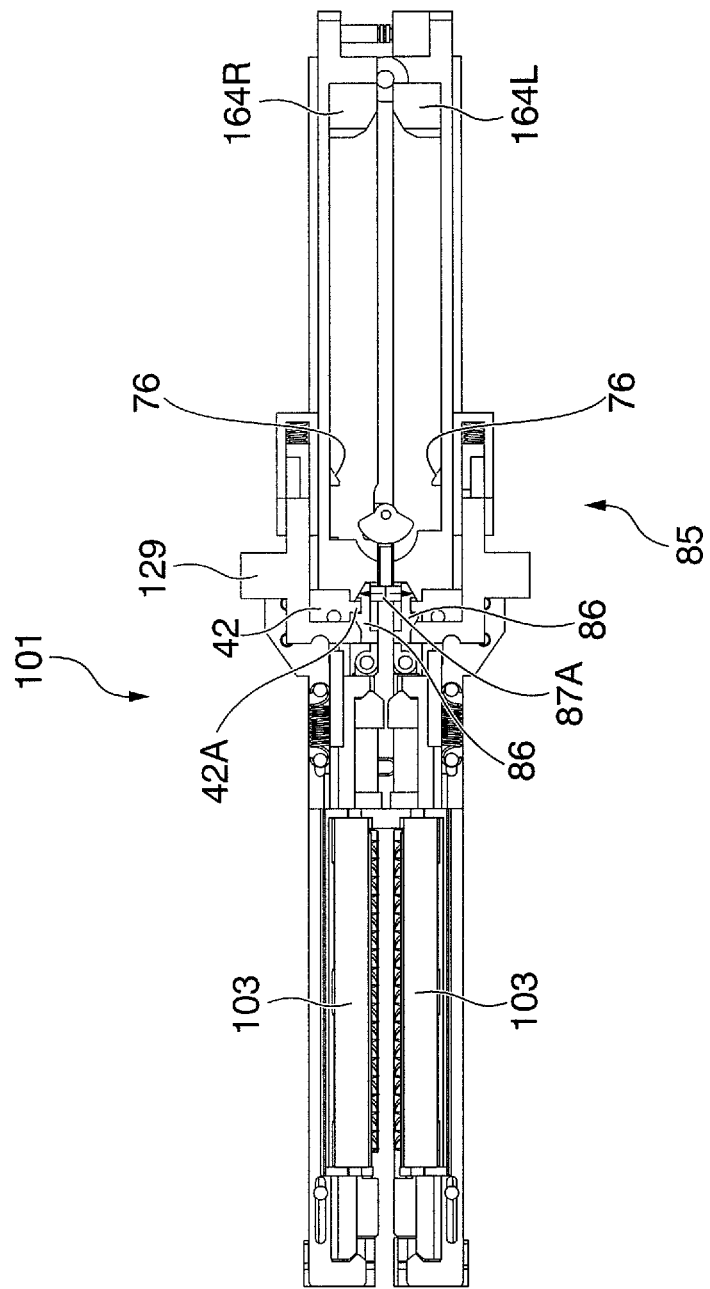
FIG. 58 is a view for explaining the action of the lock releasing mechanism in the anastomotic apparatus according to a second embodiment of the present invention, and is a planar view showing the state prior to action of the ejection knob of the ejector.

First, as shown in FIG. 58, the right and left clamps 102R, 102L are closed by rotating around the axis O2, to form the anastomotic apparatus 101.

When the right and left clamps 102R,102L are closed, the controlling projection 87A of the lock controlling member 87 is held at the rear ends of the right and left locking members 86.

When the controlling projection 87A is held at the rear ends of the right and left locking members 86, the inclined part 129A of the release knob 129 and the locking projection 42A of the operating knob 42 engage with the locking inclined part 86A of the locking member 86 and the locking recess 86B respectively, thereby constraining the release knob 129.

Figure 59:
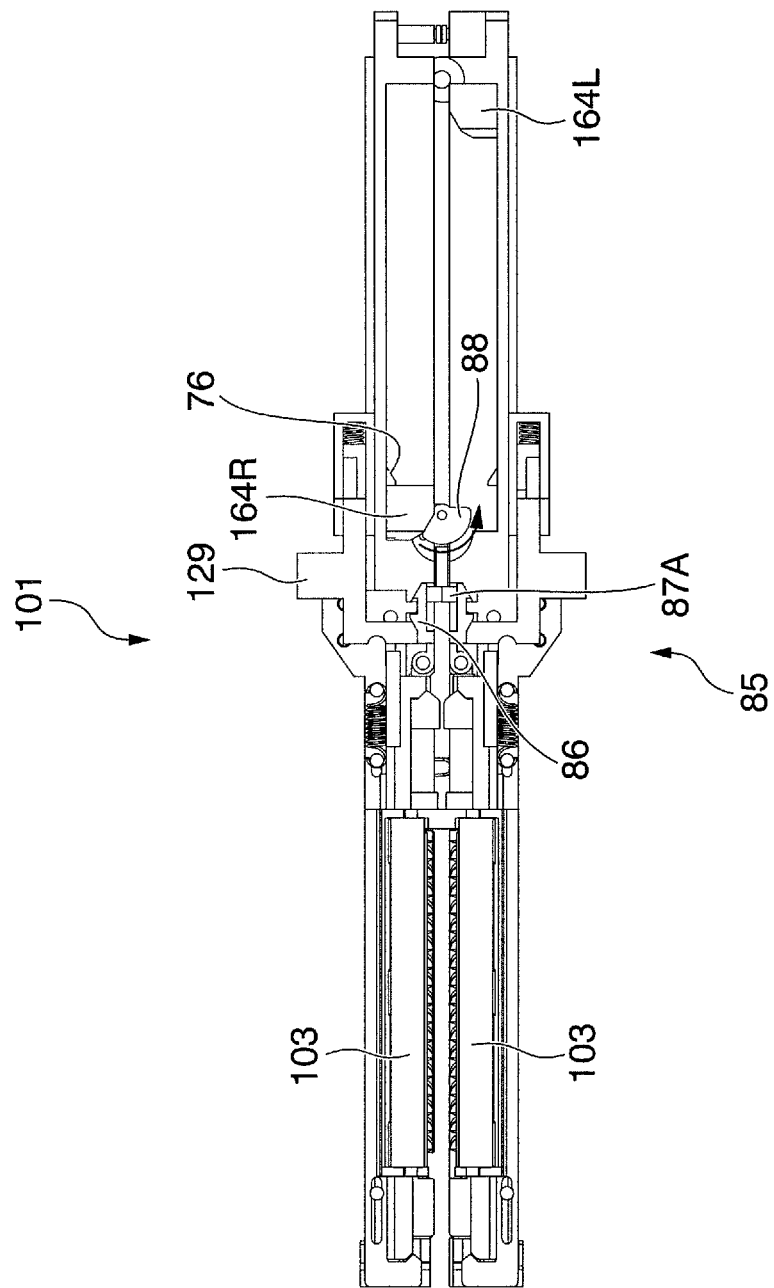
FIG. 59 is a view for explaining the action of the lock releasing mechanism in the anastomotic apparatus according to a second embodiment of the present invention, and is a planar view showing the state after action of one of the ejection knobs of the ejector.

Next, as shown in FIG. 59, when the right ejection knob 164R is operated and moves to the leading edge for example, the ejection knob 164R is constrained at the leading edge due to the ejector locking member 76. For this reason, the rocking member 88 rotates in the counter clockwise direction in FIG. 59. As a result, the transmission of the movement of the ejection knob 164R to the lock controlling member 87 is prevented.

Figure 60:
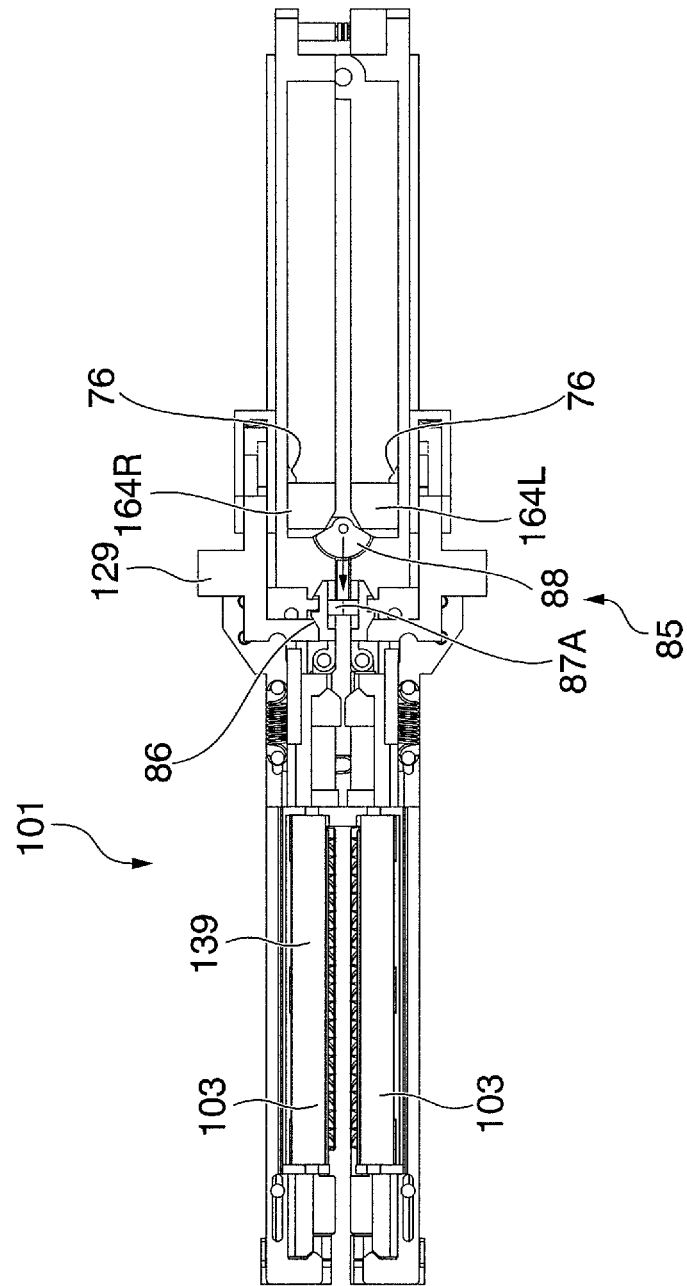
FIG. 60 is a view for explaining the action of the lock releasing mechanism in the anastomotic apparatus according to a second embodiment of the present invention, and is a planar view showing the state after action of both ejection knobs of the ejector.

Next, as shown in FIG. 60, when the left ejection knob 164L is operated and moves to the leading edge, it is constrained at the leading edge due to the ejector locking member 76. As a result, the rocking member 88 rotates in the clockwise direction in FIG. 60, and the movement of the ejection knob 164L is transmitted to the lock controlling member 87.

When the movement of the ejector knob 164L is transmitted to the lock controlling member 87, the controlling projection 87A of the lock controlling member 87 moves through the space between the right and left locking members 86, from the rear to the front end. As a result, the right and left locking members 86 become able to change position inwardly in the right and left directions, and the release knob 129 becomes able to move to the hand held side.

Figure 61:
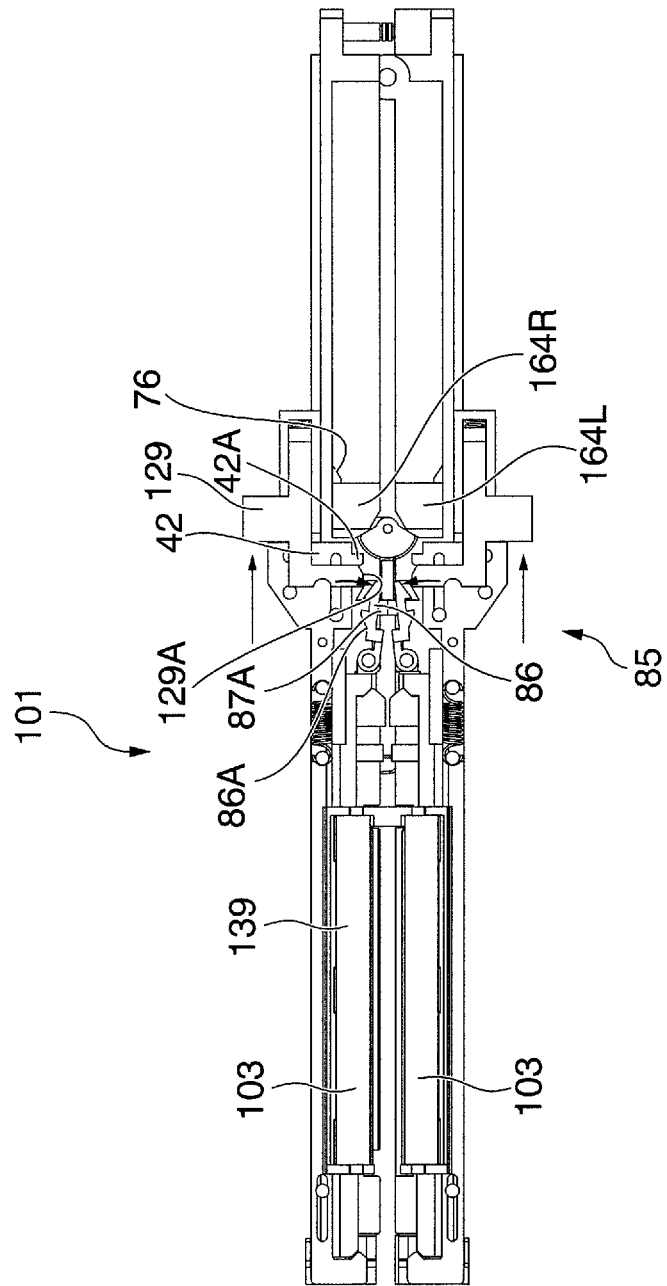
FIG. 61 is a view for explaining the action of the lock releasing mechanism in the anastomotic apparatus according to a second embodiment of the present invention, and is a planar view showing the state after action of both ejection knobs of the ejector and release by the release knob.

Next, as shown in FIG. 61, when the release knob 129 is moved to the handheld side, the locking inclined part 86A of the locking member 86 changes position inwardly in the right and left directions, and the engagement between the lock projection 42A of the operating knob 42 and the lock recess 86B is released. At the same time, the operating knob 42 is moved to the handheld side and the grip on the organ tissue P by the organ gripping mechanism 103 is released.

Using the release knob controlling mechanism 85, it is possible to release both the grip by the vertical lock and the grip by the organ gripping mechanism 103 at once using a simple manipulation of the release knob 129.

As a result, the anastomosis can be carried out safely.

By employing the everting mechanism 105 of the clamp members 121R, 121L, 125R, and 125L, it is possible to evert the organ tissue P smoothly while preventing application of a pulling force on and stretching of the gripped organ tissue P. Thus, application of unreasonable force on the organ tissue P is prevented and the stress on the organ tissue can be reduced.

The organ tissue P which is clamped by the clamp 102 is held to roughly the same thickness by the clamps 102R,102L. As a result, the stapling can be performed while stably holding the organ tissue P.

The anastomotic apparatus 101 is provided with a forward ejector locking mechanism and an ejector releasing mechanism. As a result, it is possible to stably hold the organ gripping mechanism 103, everting mechanism 105, etc., until the anastomosing operation is completed.

The anastomotic apparatus 101 is provided with a lock releasing mechanism. As a result, it is possible to prevent the anastomotic apparatus 101 from opening when the organ tissue P is being gripped by the organ gripping mechanism 103. Thus, injury to the organ tissue P can be prevented.

As disclosed above, the anastomotic apparatus 1 enables the anastomosing procedure to be carried out easily and efficiently. As a result, damage on the organ tissue P during anastomosis can be prevented.

Note that the present invention is not limited to the preceding embodiments. Rather, provided that they do not depart from the scope of the invention, a variety of suitable modifications are possible, as is a design which omits a portion of the structure disclosed in the preceding embodiments.

The case where the pointed teeth 32 and the rake teeth 36 in the organ gripping mechanism 3,103 are exposed by moving the operating knobs 41,42 from the handheld side to the distal end side was explained above. However, it is also acceptable to provide a design in which the pointed teeth 32 and the rake teeth 36 are exposed by moving the operating knobs 41,42 from the distal end side to the handheld side, i.e., to provide a design in which the distal end side of the anastomotic apparatus 1 is designated as one side and the handheld side of the anastomotic apparatus 1 is designated as the other side. Further, the decision whether or not to operate the first drive mechanism and the second drive mechanism using a common operating knob 41,42 is an option of design.

The preceding embodiments discussed the case of a design in which the opposing two clamps 2R,2L are rotated around the axis 02, and the paired clamp members 20R,20L forming these clamps 2R,2L can rotate around respective axes O1R, O1L. However, it is also acceptable for example to provide a design in which one or more of clamp pairs 121R 21R,25R, 21L, 25L forming these two clamps 2R,2L are moved apart or made to approach one another by means of a guide or the like, in place of rotation around the axes O1R, O1L (O1),O2.

Further, the first and second embodiments explained the case where the exposure of the pointed teeth 32 and the rake teeth 36 using the first drive mechanism was accomplished by moving the pointed teeth member 31 and the rake teeth member 35 with respect to the housing 39,139 in the longitudinal direction of the anastomotic apparatus 1, and relative changes of the pointed teeth 32 and the rake teeth 36 using the second drive mechanism was accomplished by moving the rake teeth member 35 with respect to the pointed teeth member 31 and the housing 39,139 in the longitudinal direction of the anastomotic apparatus 1. However, which member from among the pointed teeth member 31, rake teeth member 35, and housing 39,139 is moved to accomplish relative displacement of these elements can be optionally designed.

In the preceding embodiments, an explanation was made for the case in which the first drive mechanism and the second drive mechanism are operated using the operating knobs 41,42. However, it is also acceptable to operate the first drive mechanism and the second drive mechanism separately.

In addition, an explanation was made of the case in which the first drive mechanism and the second drive mechanism convert the movement of the operating knob 41 to a change in position of the pointed teeth 32 and the rake teeth 36 by means of the second engaging cutouts 33,37 which are formed in the pointed teeth member 31 and the rake teeth member 35. However, it is also acceptable to use another mechanism to apply changes in the position of the pointed teeth 32 and the rake 36. Further, it is also acceptable to provide a design in which a motor, actuator or the like is used to apply position changes to the pointed teeth 32 and rake teeth 36, rather than converting movement of the operating knob 41 into changes in the position of the pointed teeth 32 and the rake teeth 36.

It is also possible to provide a design in which the first drive mechanism and the second drive mechanism are driven by moving the eversion operating knobs 51,54 in the longitudinal direction of the anastomotic apparatus 1,101.

Note that in the first embodiment, an explanation was made of the case in which the eversion mechanism 105 is formed using four or more links. However, for example, it is also acceptable to provide a design using three or fewer links, or a design in which the organ gripping mechanism 103 rotates about the connecting rod 12.

In the second embodiment, an explanation was made of the case in which the everting axis O3U of the eversion mechanism 105 which is disposed to the clamp member 121R of the clamp 2R and the everting axis O3D of the eversion mechanism 105 which is disposed to the clamp member 125R are disposed to the same axis on the everting axis O3 when the clamp member 121R and the clamp member 125R are closed. However, it is also acceptable that the everting axis O3U of the clamp member 121R and the everting axis O3D of the clamp member 125R be disposed to different axis when the clamp member 121R and the clamp member 125R are closed.

Note that in the preceding embodiment, an explanation was made for the anastomotic apparatus 1,101, for the case where a firing mechanism 60,160 was disposed to clamp members 21R,121R and to clamp members 25L,125L, and an anvil member 67 was disposed to the clamp members 21L,121L and the clamp members 25R,125R. However, it is also acceptable to dispose the firing mechanism 60,160 to the clamp members 21L,121L and to the clamp members 25R,125R, and to dispose the anvil member 67 to the clamp members 21R,121R and the clamp members 25L,125L.

The provision of a floating mechanism for the stapling mechanism may be an optional design feature.

In addition, the decision of which element from among the firing mechanism 60,160, and anvil 67 to float may be optionally determined.

The first embodiment explained the case where the ejection slider 63R is advanced first, after which the ejection slider 63L is advanced. However, it is also acceptable to employ a design in which the operational sequence of the ejectors 62 is opposite that of the preceding embodiment.

Further, in the preceding explanation, the eversion mechanism 5 was formed of multilinks in the anastomotic apparatus 1, while the eversion mechanism 105 was formed of a single hinge in the anastomotic apparatus 101. However, for example, it is also acceptable to employ an eversion mechanism designed to slide in a direction that transects the fork.

The preceding embodiments explained the case where the anastomotic apparatus 1 is provided with an ejection sequence controlling mechanism, forward ejector locking mechanism, ejector lock releasing mechanism, and grip releasing mechanism. However, the provision of these elements may be optionally selected.

Further, the preceding embodiments explained the case where the clamps 2R, 2L, 102R, 102L and the clamp members corresponding thereto were employed in anastomotic apparatus 1,101. However, the aforementioned may also be employed in stapling devices for stapling organ tissues other than the intestines, stomach or other such tubular organs, or may be employed in other surgical instruments for gripping organ tissue.

In addition, the present invention is not limited to use on human organ tissue, but rather may also be suitably employed in biological gripping devices, stapling devices and anastomotic devices used for animals such as livestock or pets.

The first embodiment explained the case where the externally visible cover was formed of a lightweight plastic, while the second embodiment explained the case where an externally visible cover was not employed. In the case where an external cover is employed, the cover may be formed from a metallic material, such as titanium, or other such material which does not trigger a rejection reaction.

INDUSTRIAL APPLICABILITY

The anastomotic apparatus according to the present invention enables anastomosis of organ tissue to be carried out efficiently and stably and thus has industrial applicability.

EXPLANATION OF SYMBOLS

P organ tissue
O1 axis
O2 axis
S staple
1 anastomotic apparatus
2R, 2L clamp
3 organ gripping mechanism
5 everting mechanism
13 UB connector
13A engaging recess
20R, 20L paired clamp members
21, 25 clamp member pair
21R, 25R, 21L, 25L clamp member
31 pointed teeth member
32 pointed teeth
32A tip part
33 first engaging cutout
33A first slanted cutout
33B escape
35 rake teeth member
36 rake teeth
37 second engaging cutout
39 housing
39B cut protector
39E edge
41 operating knob
42 operating knob
43 engaging pin (first engaging member, second engaging member)
45 gripping action synchronizing mechanism
45A synchronizing projection (gripping action synchronizing mechanism)
45B synchronizing recess (gripping action synchronizing mechanism)
51 eversion operating knob
51A knob engaging projection
53, 53A, 53B, 53C, 53D link
54 eversion operating knob
J1, J2, J3, J4 support point
60 firing mechanism
61 staple housing
61A positioning pin (positioning mechanism)
62 ejector
63,63R,63L ejection slider
64S slider guide
64T slider guide
66A positioning hole (positioning mechanism)
67 anvil member
67A anvil attachment hole (floating mechanism)
67B attachment screw (floating mechanism)
68 floating mechanism
71 slider locking member
71A lock
71B releasing pin
75 slider locking recess
76 ejector locking member (forward ejector locking mechanism)
80 releasing groove
90 releasing member
93 engaging pin
95 releasing member controller
96 releasing member deforming inclined part
97 releasing member restoring step
98 inclined part
101 anastomotic apparatus
102R,102L clamp
103 organ gripping mechanism
105 everting mechanism
112 connecting plate
112A distal inclined part
120R,120L paired clamp members
121,125 clamp member pair
121R,125R,121L,125L clamp member
129 release knob
145 gripping action synchronizing mechanism
160 firing mechanism

What is claimed is:

1. A clamp member characterized in having a clamping surface that grips the organ tissue and a stapling surface on the side for stapling the organ wall, and a fork which is formed extending in the stapling direction, wherein there is provided to the fork:

an organ gripping mechanism composed so as to grip in the vicinity of a stapling site on the organ tissue, the organ gripping mechanism provided with a first gripping teeth plate member in which a plurality of pointed teeth are disposed at equal pitch in the longitudinal direction of the fork, a second gripping teeth plate member having a plurality of rake teeth which are disposed to lie along the first gripping teeth plate member corresponding with the various pointed teeth, the rake teeth being disposed with the same pitch as that of the corresponding pointed teeth and being formed so that the distal end side thereof is directed toward the corresponding pointed teeth side, wherein the tips of the rake teeth and the tips of the pointed teeth are designed to coincide as a result of movement of the second gripping teeth plate member relative to the first gripping teeth plate member, a housing for housing the first gripping teeth plate member and the second gripping teeth plate member so as to enable relative movement there between, and a gripping teeth drive which is connected to at least one of either the first gripping teeth plate member and the second gripping teeth plate member and is for relative movement of the first gripping teeth plate member and the second gripping teeth plate member by one pitch increments in the longitudinal direction;

an everting mechanism which is connected to the organ gripping mechanism and moves the organ gripping mechanism within an eversion movement range that transects the longitudinal direction of the fork and extends from a pre-eversion position at which the pointed teeth pierce the vicinity of the stapling side on the organ tissue, to a post-eversion site at which the stapling site on the organ tissue is positioned on the stapling surface; and a grip controlling mechanism which is disposed to the fork and defines the eversion movement range for the organ gripping mechanism, the grip controlling mechanism holding the organ gripping mechanism at the pre-eversion position and the post-eversion position, respectively, and controlling the first gripping teeth plate member and the second gripping teeth plate member when the organ gripping mechanism is moved to the post-eversion position side.

2. A clamp according to claim 1, wherein the organ gripping mechanism is designed so that the pointed teeth advance in the piercing direction when the first gripping teeth plate member and the second gripping teeth plate member undergo relative displacement, causing gripping of the organ tissue, and is provided with a gripping teeth protecting wall for housing the tips of the pointed teeth and the rake teeth and preventing contract between the tips of the pointed teeth and the rake teeth with the outside.

3. A clamp member according to claim 1, wherein the pointed teeth are formed extending in the piercing direction or extending in a direction which is inclined toward the rake teeth side.

4. A clamp member according to claim 1, wherein the pointed teeth are formed so that the tip side gradually displaces toward the rake teeth side.

5. A clamp member according to claim 1, wherein the organ gripping mechanism is provided with
first engaging cutouts which are formed to the first gripping teeth plate member and have a first slanted cutout which is inclined toward the side away from the pointed teeth and toward the gripping action direction in which the second gripping teeth plate member moves relative to the first gripping teeth late member when gripping the organ tissue, and an escape, which extends from the gripping action direction edge of the first slanted cutout toward the gripping action direction;
second engaging cutouts which are formed to the second gripping teeth plate member and are inclined toward the side away from the rake teeth and toward the gripping action direction; and
a gripping teeth actuating member which is formed to the gripping teeth drive and engages with the first engaging cutout and the second engaging cutout;
wherein the gripping teeth actuating member moves in the gripping action direction causing the tips of the rake teeth and the pointed teeth to advance in the piercing direction, while at the same time the rake teeth move toward the corresponding pointed teeth.

6. A clamp member according to claim 1, wherein the organ gripping mechanism has a guide formed to the stapling surface side of the housing and is able to cut and separate the organ tissue disposed to the clamping surface at a specific interval from the stapling site or from a position corresponding to the stapling site by moving a cutting blade moves through the guide.

7. A clamp member according to claim 1, wherein the everting mechanism is provided with an everting operator which is disposed to respective the forks and is connected to respective the organ gripping mechanisms, and which moves the tips of the pointed teeth and the rake teeth through a specific eversion trajectory corresponding to the eversion movement range by means of rotation, sliding and compound actions.

8. A clamp member according to claim 1, wherein the everting mechanism is capable of everting the organ gripping mechanism using remote manipulation of the everting operator, and is designed to enable holding of the organ gripping mechanism at the pre-eversion position or the post-eversion position.

9. A clamp member according to claim 1, wherein the everting mechanism is provided with a link mechanism consisting of at least four links, and is designed so that the tips of the pointed teeth and the rake teeth move along a specific eversion trajectory corresponding to the eversion movement range as a result of the link mechanism changing its arrangement at the plane which intersects with the stapling direction.

10. A clamp member according to claim 9, wherein in the organ gripping mechanism, the gripping teeth drive and the first gripping teeth plate member and the second gripping teeth plate member are connected to permit relative movement in the direction which intersects with the longitudinal direction of the fork.

11. A clamp member according to claim 1, wherein the everting mechanism is provided with an eversion rotating support for supporting the organ gripping mechanism so that the tips of the pointed teeth and the rake teeth travel on a specific eversion trajectory corresponding to the eversion movement range, by means of rotation about the everting axis formed along the stapling direction.

12. A clamp member according to claim 11, wherein the everting mechanism is provided with an everting position engaging member for selectively engaging with the organ gripping mechanism at one of either the pre-eversion position or the post-eversion position, wherein the eversion position engaging member
engages with the organ gripping mechanism at the pre-eversion position until the gripping teeth drive moves the pointed teeth and the rake teeth to the gripping position,
enables eversion of the organ gripping mechanism when the pointed teeth and the rake teeth are in the gripping state and
engages with the organ gripping mechanism at the post-eversion position after the everting manipulation has been performed.

13. A clamp member according to claim 12, wherein the eversion position engaging member is capable of moving together with the organ gripping mechanism and is provided with a pre-eversion position engaging part for engaging with the organ gripping mechanism at the pre-eversion position until the pointed teeth and the rake teeth have moved to the gripping position, and a post-eversion position engaging part for engaging with the organ gripping mechanism at the post-eversion position after the organ gripping mechanism has been everted, wherein eversion is enabled when the pointed teeth and the rake teeth are present at the gripping position, and the eversion position engaging member undergoes movement relative to the organ gripping mechanism as a result of the eversion operation, so that the engagement with the organ gripping mechanism changes between the pre-eversion position engaging part and the post-eversion position engaging part.

14. A clamp which is formed by disposing as a pair two of the clamp members according to claim 1, wherein the clamping surfaces are able to approach or move away from one another, and, when made to approach one another, the clamping surfaces face one another.

15. A clamp according to claim 14, wherein the provision of a gripping action synchronizing mechanisms for synchronizing and carrying out relative movement of the organ gripping mechanism disposed to each of the clamp members.

16. An anastomotic apparatus in which the clamps according to claim 14 are disposed as a pair so that their mutual the clamping surfaces are able to approach or move away from one another, and so that the clamping surfaces face one another when brought closer together, and in that there is formed in the clamp set a stapling mechanism which is disposed to either one of the clamp members in the two clamp member pairs, a clamp member pair being comprised of the two clamp members which face each other about the stapling surface, wherein the stapling mechanism is provided with:

a staple housing for housing the staples, in which a hole is formed on the stapling surface side through which the staples pass, an ejector for pushing out the staples from the staple housing, and an anvil member which is disposed to the other clamp member of the clamp member pair and which is formed with a profile for shaping the staples on the stapling surface side.

* * * * *